United States Patent [19]

Nakabayashi et al.

[11] Patent Number: 5,243,035
[45] Date of Patent: Sep. 7, 1993

[54] SIALIC ACID-CONTAINING GLYCOLIPID DERIVATIVES

[75] Inventors: Satoru Nakabayashi, Kawasaki; Kunio Higashi, Yachiyo; Shiro Miyoshi, Kashiwa; Hitoshi Yamauchi, Tokyo, all of Japan

[73] Assignee: Drug Delivery System Institute, Ltd., Tokyo, Japan

[21] Appl. No.: 752,604

[22] PCT Filed: Feb. 25, 1991

[86] PCT No.: PCT/JP91/00238

§ 371 Date: Aug. 15, 1991

§ 102(e) Date: Aug. 15, 1991

[87] PCT Pub. No.: WO91/13079

PCT Pub. Date: Sep. 5, 1991

[30] Foreign Application Priority Data

Feb. 27, 1990 [JP] Japan .................. 2-46602
Mar. 26, 1990 [JP] Japan .................. 2-75928
Mar. 26, 1990 [JP] Japan .................. 2-75929
Jun. 25, 1990 [JP] Japan .................. 2-166473

[51] Int. Cl.$^5$ .................. C07H 15/04; C07H 15/14; A61K 9/127
[52] U.S. Cl. .................. 536/4.1; 424/489; 424/499; 424/450; 536/124
[58] Field of Search .................. 536/4.1, 124; 424/450, 424/489, 499

[56] References Cited

FOREIGN PATENT DOCUMENTS 63-41494  2/1988  Japan .
63-264493 11/1988  Japan .
1-52794   2/1989  Japan .
1-93562   4/1989  Japan .
2-25496   1/1990  Japan .

OTHER PUBLICATIONS

*Chemical and Pharmaceutical Bulletin*, vol. 37, No. 8, pp. 2258 to 2260 (1989).

*Primary Examiner*—Ronald W. Griffin
*Attorney, Agent, or Firm*—Nixon & Vanderhye

[57] ABSTRACT

Sialic acid- containing glycolipid derivatives represented by the following general formula, their production method, and the particulate carriers that contain as a constituent the sialic acid-containing glycolipid derivative(s).

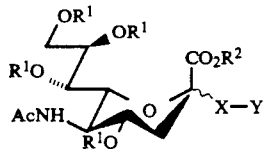

wherein $\sim$ represents the α- or the β- linkage,
$R^1$, a hydrogen atom or an acetyl group,
$R^2$, a hydrogen atom, a lower alkyl group with 1-4 carbon atoms, an alkaline metal ion, or such,
X, an oxygen or sulfur atom or a residue represented by the following formula (II) or (III), $$-O(CH_2)_m NHCO- \qquad (II)$$

where m represents an integer from 1 to 10.

$$-O(CH_2)_m CONH- \qquad (III)$$

Y, the formula (IV).

$$-(CH_2)_n-\underset{B}{\underset{|}{CH}}-(CH_2)_{n'}-A \qquad (IV)$$

where A represents a linear or branched chain acylamino group with 10–40 carbon atoms, or such
B, a hydrogen atom, a carboxyl group or such, or the formula (V), and

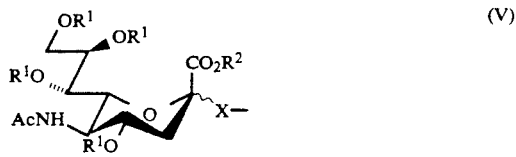

n, an integer of 0 to 3.

17 Claims, 3 Drawing Sheets

201

203a: α-glycoside
203b: β-glycoside

204a: α-glycoside
204b: β-glycoside

205a: α-glycoside
205b: β-glycoside

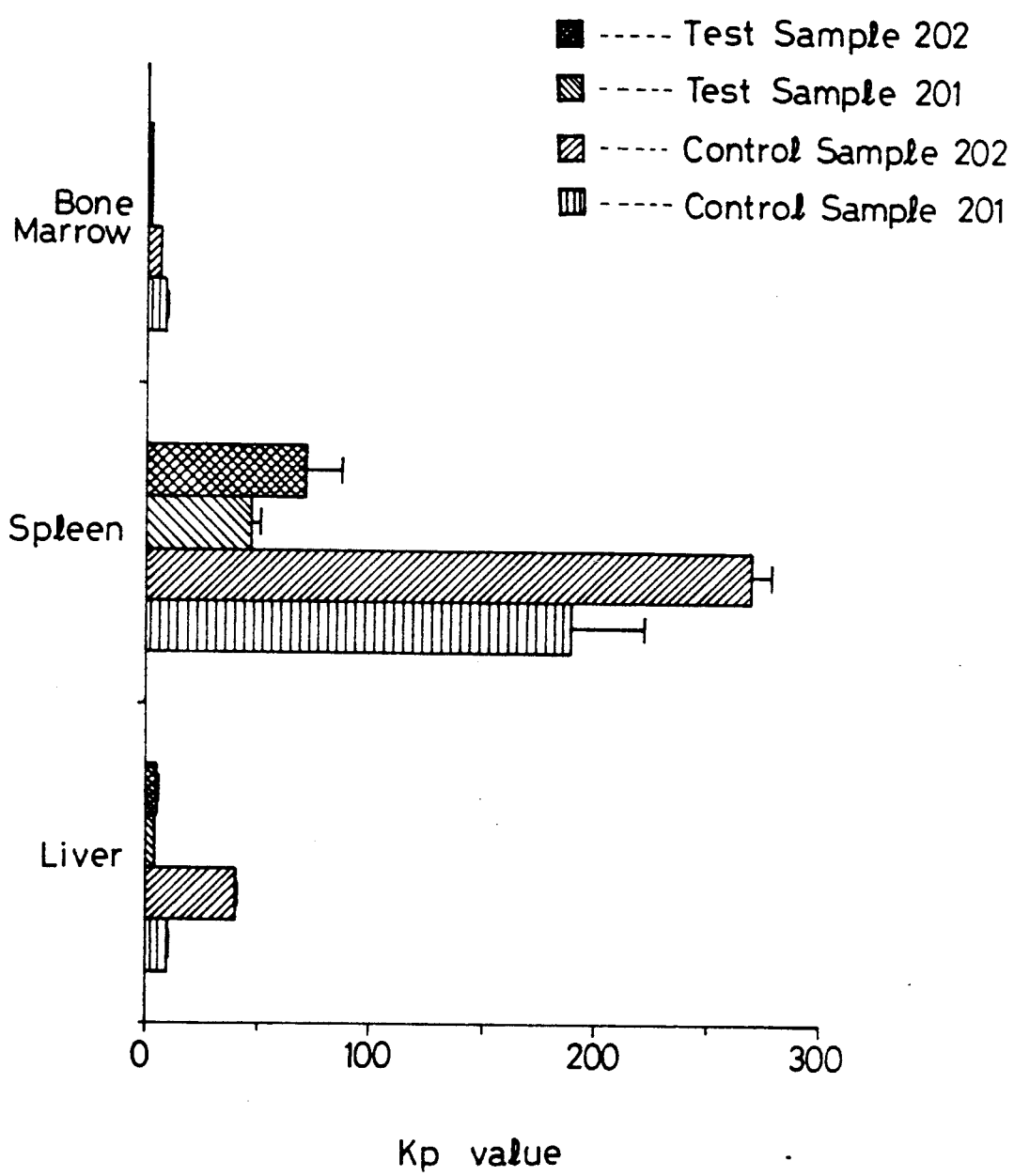

SIALIC ACID-CONTAINING GLYCOLIPID DERIVATIVES

TECHNICAL FIELD

This invention relates to sialic acid containing glycolipid derivatives which are useful as a constituent of medical preparations such as particulate drug carriers, e.g., liposome, said preparations being difficult to capture by the reticuloendothelial system represented by liver, spleen, etc., i.e., having an excellent microcirculation within the living body, and being therefore able to maintain high drug levels in blood, synthetic method of such derivatives, and particulate drug carriers with such derivative(s) as a main component.

BACKGROUND ART

A great number of studies have been made on the drug delivery system that enables effective medicinal treatment by delivering a drug administered to the living body to desired tissues in desired amounts at desired times. Many drug carriers have been reported by now, and out of them particulate carriers such as liposome and lipid microsphere are among those drug carriers that strongly attract general attention. Generally speaking, when particulate carriers like liposome are administered into a blood-vessel, it is readily captured, as is well known, by the reticuloendothelial system represented by liver and spleen. This phenomenon forms a big problem when such preparations are utilized as a release-controlling carrier that allows release of the drug in a controlled manner or as a targeting carrier that allows delivery of the drug to desired organs, e.g., in intravenous administration.

Such drug carriers as described above that, in systemical administration such as intravenous administration, are resistant to capture by the reticuloendothelial system, and show improved microcirculation activity within the living body have been studied so far. Taking as an example liposomes in respect of which their membrane components may be altered in their combination, to improve microcirculation activity, cholesterol is added (Biochem. Pharmacol., 32, 609(1983)), or a lipid having a high phase-transition temperature is used (Biochem. Biophys. Acta, 839, 1(1985)). Also there is a case where, as the size of liposomes can be relatively easily controlled, liposomes are reduced in size to improve microcirculation (J. Pharmacol. Exp. Therap., 226. 539(1983)).

In addition, recently there are communications reporting that ganglioside or a glycolipid derived from the cell membrane, or glycophorin or a glycoprotein from the red blood cell membrane is incorporated into the liposome membrane for their reorganization in order to improve microcirculation. As an example for the former, there is an article reporting that the use of ganglioside $GM_1$ gives liposomes an increased resistance to capture by the reticuloendothelial system, to ensure relatively stable microcirculation of the liposome in blood (Biochim. Biophys. Acta, 981, 27(1989), U.S. Pat. No. 4,837,028 (Jun. 6, 1989)). As an example for the latter, there is an article reporting that the use of glycophorin derived from human red blood cells brings about the same effect (Proceedings of the 9th Symposium of "Biomembrane and Drug Interaction", p. 193, Tokyo, 1986). There are other similar reports describing the reorganization into a liposome membrane of a glycolipid derived from fetuin or a blood serum protein (Chem. Pharm. Bull., 36, 4187(1988)), and the use as liposome membrane components of sialic acid bound to a polysaccharide such as pullulan or amylopectin together with cholesterol residue (Chem. Lett., pp. 1781(1988)).

As described above, a large number of studies have indeed been made on the manufacture of liposome preparations that can achieve a microcirculation in the blood circulatory system, by circumventing the capture by the reticuloendothelial system. But, the current state is far from the desired goal in that carriers with a glycolipid or glycoprotein as their component in such a manner as stated above are still inadequate in industrial productivity and practicability, taking into consideration the mass production and material cost aspect.

The present invention aims at providing novel substances that are resistant to capture by the reticuloendothelial system such as liver, spleen, etc., capable of conferring microcirculation activity in vivo to particulate carriers such as liposome, and further allow mass production of industrially reproducible quantity.

DISCLOSURE OF INVENTION

FIRST: The inventors have investigated appropriate components of particulate carriers such as liposome that can avoid uptake by the reticuloendothelial system and therefore have a property of maintaining microcirculation, and found that the sialic acid-containing glycolipid derivatives of the following general formula (I) or (VI), either in the $\alpha$ form or the $\beta$ form, or a mixture of both, when incorporated into the liposome membrane, can help solve effectively the above problems. On these findings, they have made this invention.

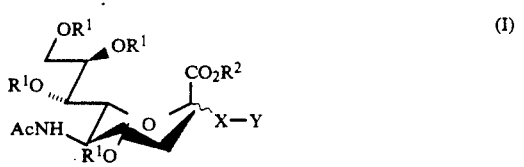
(I)

In this formula, ∼ represents the $\alpha$ or $\beta$ linkage; $R^1$, a hydrogen atom or acetyl group; $R^2$, a hydrogen atom, a lower alkyl group with 1 to 4 carbon atoms, an alkali metal ion, an alkaline earth metal ion or an ammonium ion, preferably an ammonium ion of a lower amine with 3 to 16 carbon atoms;

X is an oxygen atom, a sulfur atom, or a residue of the following formula (II) or (III); and $$—O(CH_2)_mNHCO— \quad (II)$$

in which m represents an integer from 1 to 10.

$$—O(CH_2)_mCONH— \quad (III)$$

in which m represents the same integer as in the formula (II).

Y represents the formula (IV).

(IV)

In the formula (IV), A represents a hydrogen atom, a linear chain or branched chain of an acylamino, alkyl, alkenyl, alkoxy, alkenyloxy, alkylthio, or alkenylthio group with 10 to 40 carbon atoms; and B represents a hydrogen atom, a carboxyl, carbamoyl or N-alkyl-substituted carbamoyl group, an alkyl, alkenyl, alkoxy, alkenyloxy or acylamino group with 10 to 30 carbon atoms, or the formula (v); and

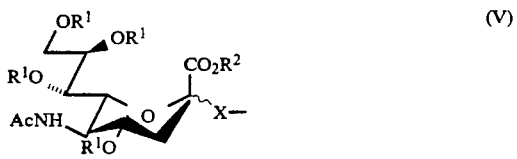
(V)

in which $R^1$, $R^2$ and X have the same meaning as described above.

n and n' are each an integer from 0 to 3.

Those compounds are, however, excluded from claim which are of the formula (I) wherein X is an oxygen or sulfur atom, and either A or B in the formula (IV) is an hydrogen atom and the other is an alkyl or alkenyl group; of the formula (I) wherein X is an oxygen or sulfur atom, and A and B in the formula (IV), which may be the same or different, an alkyl or alkenyl group; and of the formula (I) wherein X is an oxygen atom, and both A and B in the formula (IV) are an alkyloxy group.

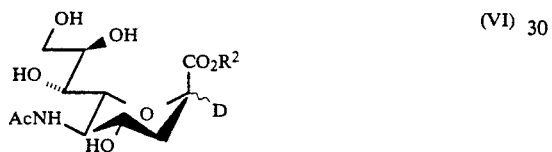
(VI)

in which ~ and $R^2$ have the same meaning as in the foregoing formula (I), and D represents a linear or branched chain of an alkyloxy or alkenyloxy group with 14 to 40 carbon atoms.

The present invention provides the sialic acid-containing glycolipid derivatives of the general formula (I) or (VI).

Next will be explained the production method of the sialic acid- containing glycolipid derivatives of the general formula (I) or (VI).

The compounds of the present invention are the sialic acid- containing glycolipid derivatives having 1 or 2 sialic acid residues at the terminal and said residue(s) bound to an aliphatic chain via a variety of linking arms. Hence, an appropriate synthetic method should be chosen according to the type of the linking arm concerned.

For example, there is a method in which sialic acid is led to a sugar donor following a routine procedure, while a sugar receptor with an aliphatic chain is prepared separately, and the two are combined for reaction. Or, there is a second method in which a linking arm is attached to a sialic acid donor, and then, another sialic acid- containing derivative or aliphatic chain is attached thereto.

In short, for preparing a sialic acid donor it is most simple and convenient to utilize 2-chloride compound (ii) derived from peracetyl sialic acid methylester (i) following the method of R. Kuhn et al. (Chem. Ber., 99, 611(1966)) and the method of H. Ogura et al. (Tetrahedron Lett., 22, 4265(1981)).

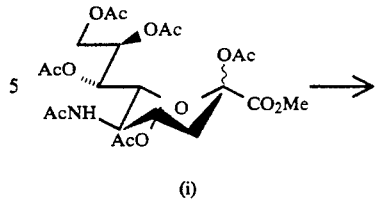
(i)

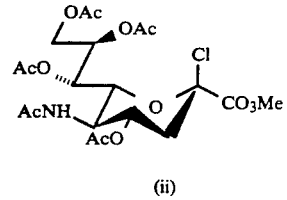
(ii)

On the other hand, preparation of a sugar receptor varies depending on the form of that compound. For obtaining a sugar receptor with an aliphatic chain, for example, a conventional acylation of the amino group of an aminoalcohol (iii) produces the corresponding compound (iv).

$$HO(CH_2)_mNH_2 \longrightarrow HO(CH_2)_mNHCOY$$
(iii)                   (iv)

In the formulas, m and Y have the same meaning as in the previous formulas (II) and (I).

Or, hydroxycarboxylic acid (v) is, after its hydroxyl group has been protected with a certain conventional protective group such as an acyl or benzyl group including an acetyl or benzoyl, converted to an activated ester, which is, using a condensing agent, allowed to react with an aliphatic amine having 10 to 40 carbon atoms in the presence of an inorganic base such as sodium hydrogencarbonate or potassium carbonate or of an organic base such as triethyl amine or pyridine, to produce the compound (vi). Further, removal of the protective group from its hydroxyl group results in production of the compound (vii).

$$HO(CH_2)_mCO_2H \longrightarrow ZO(CH_2)_mCONHA' \longrightarrow$$
(v)                   (vi)

$$HO(CH_2)_mCONHA'$$
(vii)

In the above formulas, Z represents a general protective group for a hydroxy group, and m has the same meaning as in the formula (II).

The aliphatic chains of the sugar receptors (iv) and (vii) thus produced should have a certain or more degree of liposolubility, to be incorporated into a particulate carrier. For this purpose, a linear or branched chain alkyl or alkenyl with 10 to 40, preferably 14 to 34 carbon atoms is used.

Condensing the sugar receptor (iv) and/or (vii), or a linear or branched chain alkyl or a alkenyl alcohol with a sialic acid donor (ii) results in production of a variety of sialoglycolipids. Namely, reaction with the use of a mercury salt such as mercury (II) cyanide or mercury (II) bromide, or a silver salt such as silver carbonate, silver perchlorate or silver trifluoromethanesulfonate, as catalyst in an inert solvent such as methylene chloride or tetrahydrofuran in the presence of an inorganic deoxidizer such as a molecular sieves or Drierite or of an organic deoxidizer such as N,N'-tetramethyl urea or 2,6-lutidine, produces the compounds (viii), (viiia) and (ix). The condensing reagent should be selected appropriately depending on the matter properties of sugar receptors to be used. The compounds (viii), (viiia) and (ix) are deacetylated, e.g., with methanol solution of sodium methoxide, and the resultant methylesters are hydrolyzed with an alkali solution such as sodium hydroxide solution, to produce the compounds (x), (xa) and (xi), respectively.

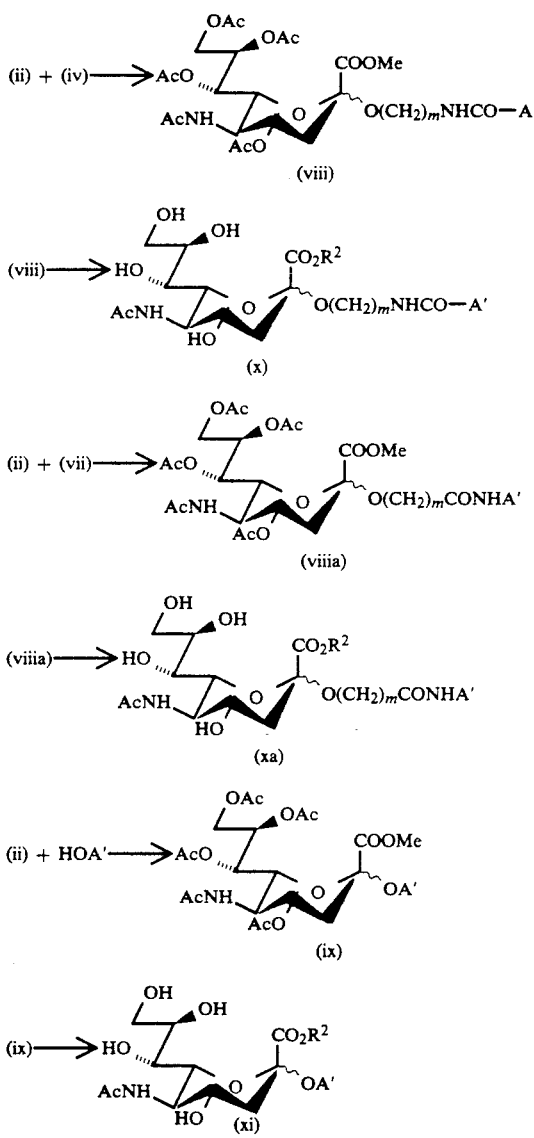

In the formulas (viii) and (viiia), m represents the same integer as in the formula (II), and in the formulas (x), (xa) and (xi), $R^2$ represents a hydrogen atom, a lower alkyl group with 1 to 4 carbon atoms, an alkaline metal ion, an alkali earth metal ion or an ammonium ion, preferably an ammonium ion of a lower amine having 3 to 16 carbon atoms, and A' has the same meaning as in the formula (vi).

The method in which sialic acid acid is initially connected with a linking arm is also effective. An amino alcohol compound (xii) with its amino group protected via a routine procedure, or an azido alcohol compound (xiii) derived, e.g., from a haloalcohol or dihydroxyalkane via a routine method is condensed with a sialic acid donor (ii) in the procedure as described above, to produce the compounds (xiv) and (xv).

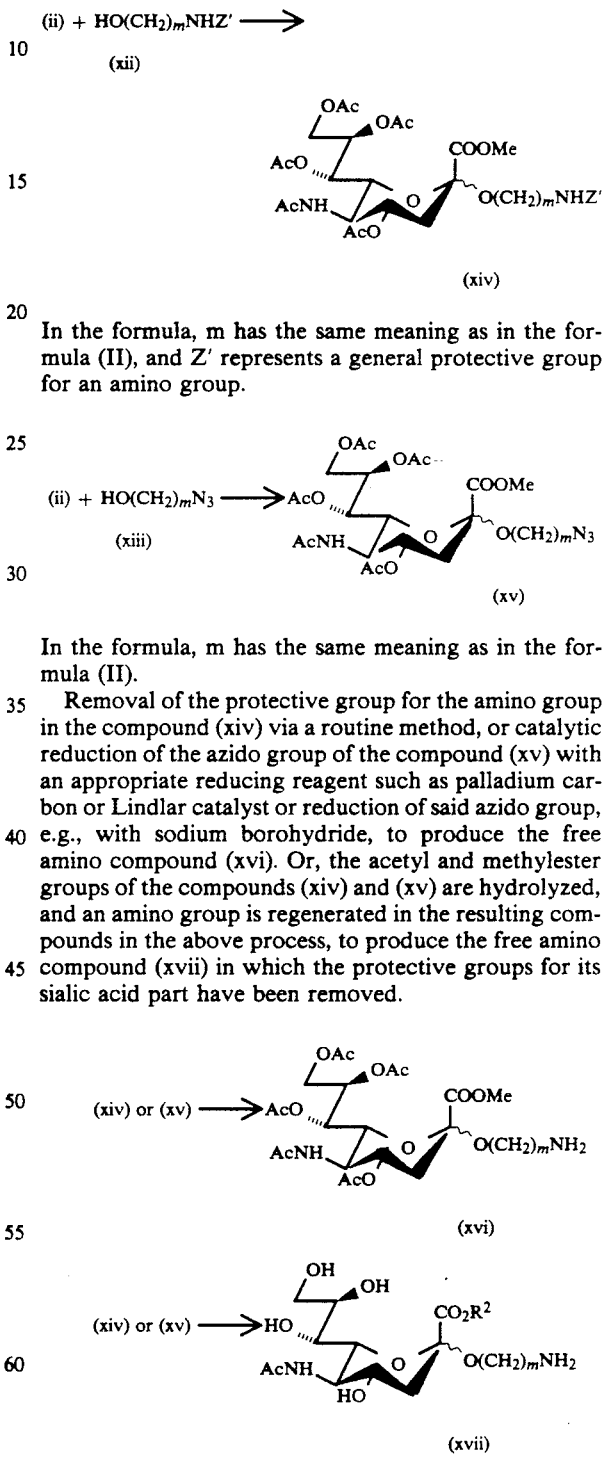

In the formula, m has the same meaning as in the formula (II), and Z' represents a general protective group for an amino group.

In the formula, m has the same meaning as in the formula (II).

Removal of the protective group for the amino group in the compound (xiv) via a routine method, or catalytic reduction of the azido group of the compound (xv) with an appropriate reducing reagent such as palladium carbon or Lindlar catalyst or reduction of said azido group, e.g., with sodium borohydride, to produce the free amino compound (xvi). Or, the acetyl and methylester groups of the compounds (xiv) and (xv) are hydrolyzed, and an amino group is regenerated in the resulting compounds in the above process, to produce the free amino compound (xvii) in which the protective groups for its sialic acid part have been removed.

In the formula (xvii), $R^2$ has the same meaning as in the formula (x).

2,3-di-O-alkylglyceric acid can be prepared, for example, via the following procedure. Glyceraldehydedialkylacetal is allowed to react with a linear or branched chain halogenated alkane or halogenated alkene with 10 to 40, preferably 14 to 34 carbon atoms in an inert solvent such as N,N-dimethylformamide in the presence of a base such as sodium hydride or barium hydroxide, to produce 2,3-di-O-alkyl or alkenyl-glyceraldehyde-dialkylacetal. The resulting compound is allowed to react with mineral acid such as hydrochloric acid or organic acid such as p-toluenesulfonic acid in a water-containing solvent for removal of acetal, and then to react with an alkali metal salt of permanganic acid, an ammonium salt such as tetraethylammonium salt or an ordinary oxidizing agent of aldehyde, to produce 2,3-di-O-alkylglyceric acid (xviii).

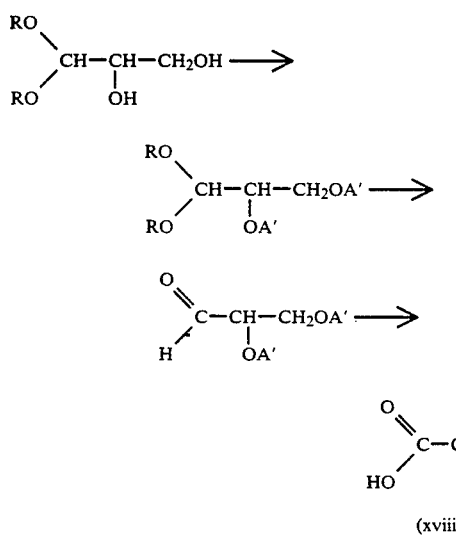

(xviii)

In the formulas, R represents a lower alkyl group with 1 to 4 carbon atoms, and A, has the same meaning as in the formula (vi).

2,3-di-O-alkylglyceric acid (xviii) (of which the number of the carbon atoms in the alkyl group should be preferably 12 to 24 from the view point of a chain length easy to handle and obtain) is converted via a routine method to an activated ester compound, which is allowed to react with the amine compound (xvi), to produce the compound (xviiia). When necessary, the resulting compound is deacetylated, and the methylester is hydrolyzed, to produce the derivative (xix) with the protective group for the sialic acid removed.

(xviii) + (xvi) ⟶

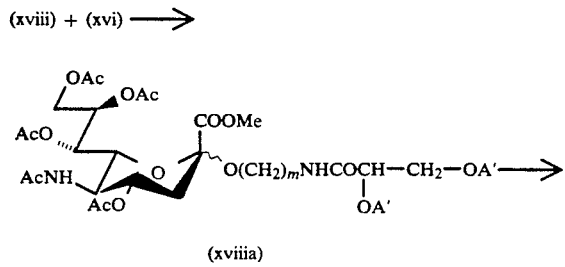

(xviiia)

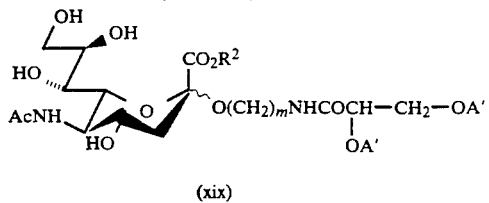

(xix)

In the formula (xviiia), m has the same meaning as in the formula (II) and A', as in the formula (vi), and in the formula (xix), $R^2$ has the same meaning as in the formula (x) and m, as in the formula (II).

Use of the amine compound (xvii) instead of the amine compound (xvi) allows production of the derivative (xix) with the protective group for the sialic acid removed directly without intervention of a deprotection reaction. 2,2-dialkylacetic acid can be prepared, for example, as follows; Malonic acid diester, preferably malonic acid dibenzylester, is allowed to react with a strong base such as sodium hydride or barium hydroxide in an inert solvent such as N,N-dimethylformamide, and is then added with an activated alkyl group such as a linear chain halogenated alkyl with 6 to 20, preferably 7 to 16 carbon atoms, to produce the compound (xx). The compound is, after the two diesters have been removed conventionally, e.g., with an alkaline solution or via catalytic reduction, decarboxylated by heating or through an acidic catalytic reaction, to produce the compound (xxi).

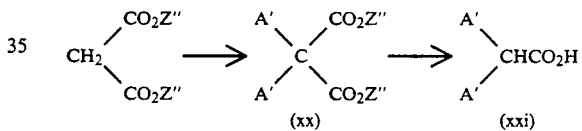

(xx)    (xxi)

In the above, A' is the same as in the formula (vi) and Z" represents a general protective group for a carboxyl group.

The compound (xxi) is, after having been converted to an activated ester or acid halide as in glyceric acid (xviii), condensed with an amine compound (xvi), to produce the compound (xxii). Also, following the procedure described above, the compound in question can be subjected to deacetylation and hydrolysis of the methylester to produce the compound (xxiii).

(xvi) + (xxi) ⟶

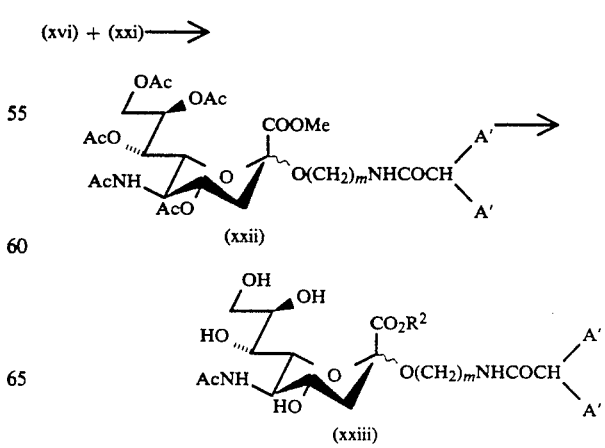

In both formulas, m is the same as in the formula (II), and A' is the same as in the formula (vi). In the formula (xxiii), $R^2$ is the same as in the formula (x).

Use of an amine compound (xvii) instead of an amine compound (xvi) allows production of the compound (xxiii) without intervention of the deprotection reaction.

A hydroxyamino acid (xxiv) such as serine or homoserine is allowed to react with an alcohol such as benzyl alcohol and an organic acid such as p-toluenesulfonic acid or a mineral acid such as sulfuric acid via a routine procedure, to produce the hydroxyamino acid ester salt (xxv). P-toluenesulfonic acid salt of serine benzyl ester is preferred. The salt thus produced (xxv) is allowed to react with a linear or branched chain saturated or unsaturated fatty acid with 10 to 40 carbon atoms, or more preferably an activated form (e.g., activated ester or acid anhydride) of said fatty acid but with 16 to 34 carbon atoms in an organic solvent or a water-containing organic solvent in the presence of an inorganic base such as sodium hydrogencarbonate or potassium carbonate, or of an organic base such as triethylamine, to produce the aliphatic chain derivative (xxvi).

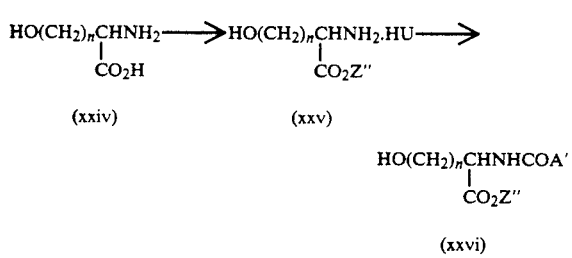

In the formulas, Z" is the same as in the formula (xx), n is the same as in the formula (IV), HU represents an acid, and A' is the same as in the formula (vi).

The compound (xxvi) is condensed with a sialic acid donor (ii) as described above, to produce the compound (xxvii).

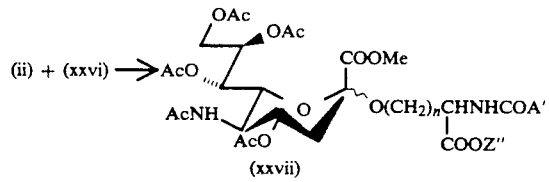

In the formula, A' is the same as in the formula (vi), Z", as in the formula (xx) and n, as in the formula (IV).

The compound (xxvii) is conventionally subjected to deacetylation and hydrolysis of the methylester to produce the compound (xxviia).

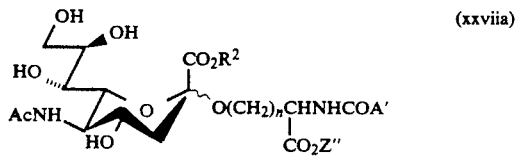

In the formula (xxviia), $R^2$ is the same as in the formula (x) and A', as in the formula (vi).

Further, the compound (xxvii) can, after removal of Z" via a routine procedure, be conventionally converted, using, e.g., N,N'-dicyclohexylcarbodiimide or N-hydroxysuccinimide, to the activated ester (xxviii). Then, the ester is allowed to react with an amine component A'-$NH_2$, where A' represents a hydrogen atom or a linear or branched chain alkyl or alkenyl group with 10 to 40 carbon atoms, in an organic solvent or water-containing organic solvent in the presence of the above-mentioned base, to produce the compound (xxix) with two or more aliphatic chains. The compound (xxix) is subjected to deacetylation and the hydrolysis of the methylester in the same manner as described above, to produce the compound (xxx).

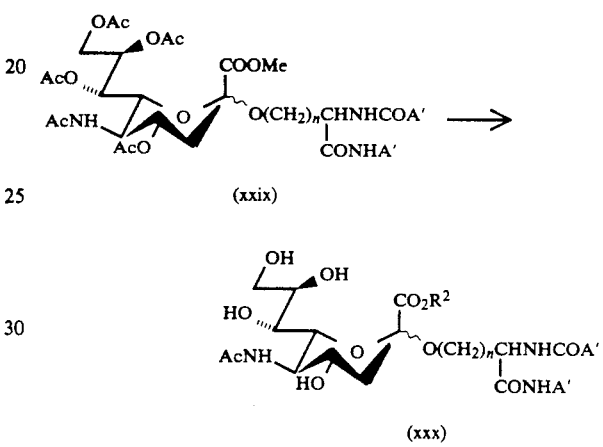

In the formula (xxix), n is the same as in the formula (IV) and A', as in the formula (vi). In the formula (xxx), $R^2$ is the same as in the formula (x), n, as in the formula (Iv) and A', as in the formula (vi).

The activated ester compound (xxviii) and the amine compound (xvi) or (xvii) are subjected to the same reaction as described above, to produce the compound (xxxi). The compound (xxxi) is similarly subjected to deacetylation and hydrolysis of the methylester, to produce the compound (xxxii).

(xxviii) + (xvi) ⟶

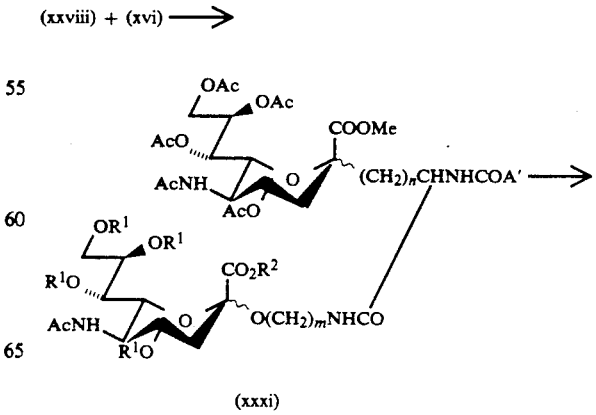

-continued

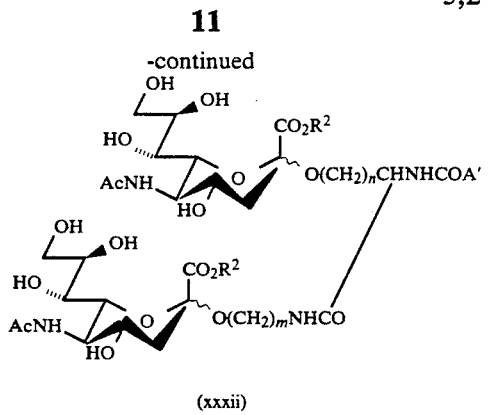

(xxxii)

In the formulas (xxxi) and (xxxii), n is the same as in the formula (IV), m, as in the formula (II), $R^1$, as in (I), $R^2$, as in the formula (x) and A', as in the formula (vi).

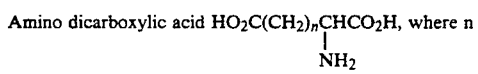

represents the same integer as in the formula (IV), is conventionally converted to a dibenzyl ester, which is made to react with a fatty acid A'CO$_2$H, where A' is the same as in the formula (vi), via a routine procedure, and is subjected to reaction for removal of the benzyl groups, to produce a fatty acid amidodicarboxylic acid derivative. Further, the derivative is allowed to react in the same manner as described above to produce an activated di-ester compound (xxxiii).

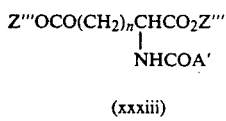

(xxxiii)

In the formula, Z''' represents an activated ester group, e.g., a succinimido group, and A' is the same as in the formula (vi).

The activated di-ester compound (xxxiii) and an amine compound (xvi) can be made to react in a conventional manner to produce the compound (xxxiv). The compound (xxxiv) can, after deacetylation and hydrolysis of the methylester in the manner as described above, be converted to the compound (xxxv). Use of an amine compound (xvii) instead of an amine compound (xvi) can produce the compound (xxxv) without the intervention of removal of the protecting groups.

(xxxiii) + (xvi) 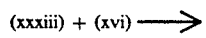

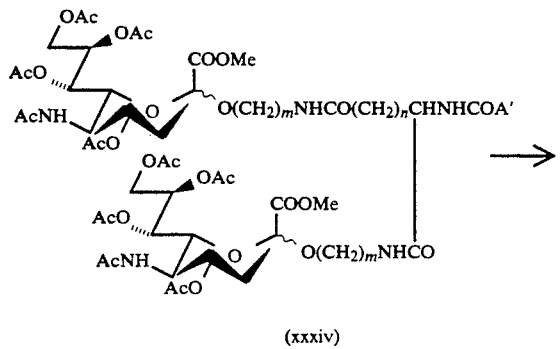

(xxxiv)

-continued

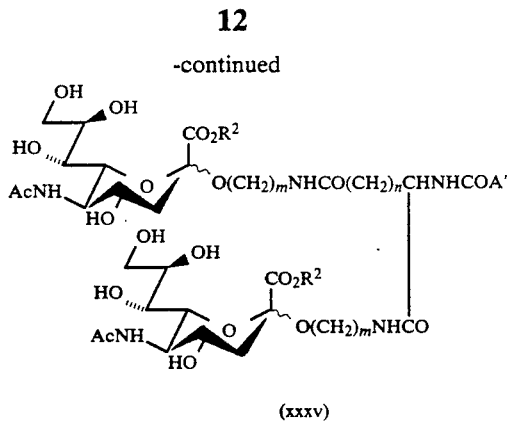

(xxxv)

In the formulas, m is the same as in the formula (II), n, as in the formula (IV), $R^2$, as in the formula (x) and A', as in the formula (vi).

SECOND: The present invention also relates to (a) compounds represented by the following general formula (XIII), (c) compounds represented by the following general formula (XIIIa), and (b) their production method.

(a); (XIII)

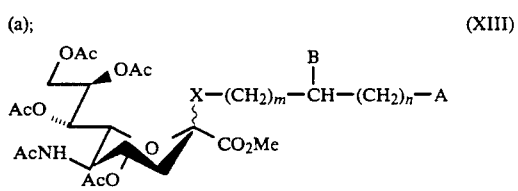

In the formula, X represents an oxygen atom or a sulfur atom, m and n, an integer of from 0 to 10, A, a hydrogen atom, a linear or branched chain acylamino, alkyl, alkenyl, alkoxy, alkenyloxy or azido group with 10 to 40 carbon atoms, or an amino group protected with a protective group, and B, a hydrogen atom, a linear or branched chain alkyl, alkenyl, alkoxy or alkenyloxy group with 1 to 30 carbon atoms, a lower alkoxycarbonyl group with 2 to 3 total carbon atoms, or a substituted or non-substituted benzyloxycarbonyl group. Examples of the protective groups for protecting the amino group in A include a benzyloxycarbonyl group and a phthaloyl group.

Those compounds are, however, excluded from claim which are of the formula (XIII) wherein X is an oxygen atom, m=1 and n=0, A is a benzyloxycarbonylamino group and B is a hydrogen atom, and in the α form; of the general formula (XIII) wherein X is an oxygen atom, and A and B are both hydrogen atoms, or alkyl, alkenyl, alkoxy or alkenyl groups; and of the formula (XIII) wherein X is a sulfur atom, and A and B are both hydrogen atoms, or alkyl or alkenyl groups.

(b); A method of producing sialic acid derivatives represented by the general formula (XIII) which comprises allowing the 2-acetyl derivative of sialic acid represented by the formula (XI) to react with an alcohol represented by the general formula (XII) in an inert solvent in the presence of a Lewis acid acting as a catalyst.

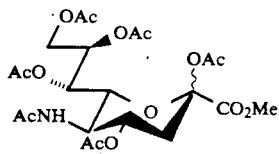 (XI)

wherein ～ represents the α or β linkage.

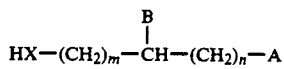 (XII)

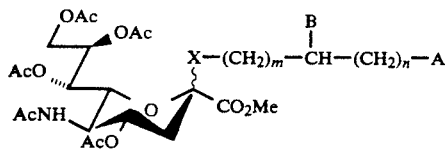 (XIII)

(c); (XIIIa)

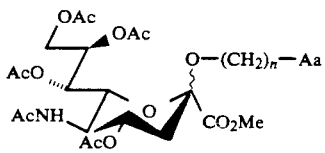

where ～ represents the α or β linkage, n, an integer of from 1 to 20, and Aa, an axido group or an amino group protected with a protective group. Those compounds are, however, excluded from claim which are of the formula (XIIIa) wherein n=2, and Aa is a benzyloxycarbonylamino group and in the α form.

The present invention relates to a method of producing sialic acid β-glycosides cheaply, massively and with high yields and with no problem in safety, and to new sialic acid derivatives.

According to the method of the present invention, it is possible to produce new-substance sialic acid containing glycolipid derivatives represented by the general formulas (I) or (VI), or their intermediates cheaply, massively and with high yields.

As a synthetic method of sialic acid glycosides represented by the formula (XV), 2-chlorosialic acid represented by the formula (XIV) has been generally used as a starting material to be reacted with an alcohol in the presence of a heavy metal salt, e.g., salts of silver, mercury, etc.

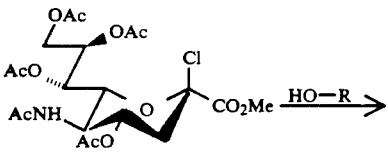

(XIV)

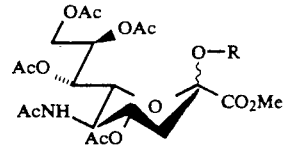

(XV)

wherein ～ represents α or β linkage.

Few studies are present that report any reaction using 2-acetyl sialic acid, i.e., the compound represented by the formula (XI), as a starting material. To mention a few as examples, one study relates to the reaction with a nucleic acid derivative where the compound is made to react with a nucleic acid nitrogen atom using SnCl$_4$ (Chem. Pharm. Bull., 34(4),1479 (1986)), and another relates to the reaction with a thioalcohol using BF$_3$·Et$_2$O (Carbohydr. Res., 187,35 (1989)). As examples of the reaction with alcohols, there is a reaction with cholesterol using trimethylsilyltriflate (TMSOTf) (Chem. Pharm. Bull., 35(10),4043 (1987)), but this reaction allows only a 5% yield of the β compound. In addition, there is an article reporting the reaction with a glycerol derivative using the same TMSOTf (Int. J. Devl. Neuroscience, 6(4), 319 (1988)), but it lacks description of yields etc. As is obvious from the foregoing, although there have been a few studies that try to make the compound react with alcohols, their yield was too low to be applied in practice.

The procedure that produces sialic acid derivatives using 2-chlorosialic acid represented by the above formula (XIV) is, though being widely used previously, problematic in cost and safety because of its involvement of a metallic salt, and is not adapted therefore to industrial mass production of sialic acid derivatives. In addition, the compound represented by the formula (XIV) is problematic in stability so that it is very difficult to store stably for a long period.

The inventors have endeavored strenuously to find a method of synthesizing the sialic acid derivatives represented by the above formula (XIII) cheaply, massively and with high yields using, as a starting material, 2-acetyl sialic acid represented by the formula (XI) which is stable and can be produced with high yields, and have achieved the present invention.

Namely, this invention relates to a method of producing sialic acid derivatives represented by the formula (XIII) which comprises allowing the 2-acetyl derivative of sialic acid represented by the formula (XI) to react with an alcohol represented by the general formula (XII) in an inert solvent in the presence of a Lewis acid acting as a catalyst.

The method of the present invention will be detailed below.

The 2-acetyl form of sialic acid represented by the formula (XI) to be used as a starting material in the synthetic method of the present invention can be easily synthesized, for example, utilizing the procedure by P. Sinay et al. (Carbohydr. Res., 190, 317 (1989)). This compound can be used as a starting material for the synthetic method of the present invention either in the α form or in the β form, or as a mixture thereof.

Alcohols represented by the formula (XII), which is the other starting material to be used for the present invention, can be produced via a conventional method, and are used at a ratio of 1 to 10 mol relative to 1 mol of the compound represented by the formula (XI), or more preferably at a ratio of 3 to 5 mol.

As the solvent, an inert solvent that has no nucleophilic property and does not react with a Lewis acid, such as methylene chloride, chloroform, acetonytrile, ether or tetrahydrofuran, is preferably used.

As the catalyst for glycosylation, Lewis acids are generally used, and of such substances, tin tetrachloride, boron trichloride ether complex salt ($BF_3 \cdot Et_2O$), etc. are preferably used. The Lewis acid is used at a ratio of 0.5 to 10 mol with respect to 1 mol of the compound represented by the formula (XI), or more preferably at a ratio of 1 to 5 mol.

The reaction in the method of the present invention can proceed without addition of a dehydrating agent, but addition of a dehydrating agent improves yields. As the dehydrating agent, an inorganic dehydrating agent such as molecular sieves (3A, 4A, AW300 and such) or calcium sulfate is preferably used.

The reaction is allowed to proceed at a temperature between $-20°$ C. and the boiling point of the solvent, or more preferably between the water freezing point and room temperature. At a temperature maintained at the above level, the reaction is ordinarily completed in 2 to 150 hours. The 2-acetyl form of sialic acid represented by the formula (XI) to be used as a starting material is stable as stated already, so that even when it is maintained at room temperature for a long time the reaction for the synthesis of this invention can proceed stably, which forms one of the merits the present invention provides.

After completion of the reaction, the product compound of interest can be isolated by a conventional method, e.g., columchromatography.

This invention also relates to the sialic acid derivatives represented by the above general formula (XIIIa). The compounds represented by the general formula (XIIIa) form a part of the compounds represented by the above formula (XIII).

THIRD: Further, the present invention relates to the sialic acid derivatives represented by the formula (XXI) and their salts,

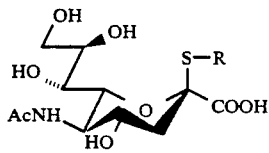

(XXI)

in which R represents a linear or branched chain alkyl or alkenyl group, and to the sialic acid derivatives represented by the above formula (XXI) in which R is, in particular, $(CH_2)_nCH_3$ wherein n represents an integer of from 13 to 29, and their salts.

R of the compounds of the present invention is necessary for stably incorporating them into particulate carriers, and for achieving this function it is only necessary that R be an aliphatic chain, and a linear or branched chain alkyl or alkenyl group accordingly. R should be preferably $(CH_2)_nCH_3$ wherein n represents an integer of from 13 to 29, because with it the synthesis proceeds smoothly, and the cost is low.

In the compounds of the present invention, the bonding type of S to the sugar residue is limited to the $\beta$ linkage. And, the salts can be, for example, the sodium salts.

In this connection, for S-neuraminic acid derivatives, description was given in Japanese Patent Application Kokai No 282390/86 and J. Carbohydrate Chemistry, 5(1), 11–19(1986), but they both treated the $\alpha$ linkage form and included no description suggestive of the utility of the compounds of the present invention.

The compounds of the present invention can be produced by any conventional method, but, e.g., the diagram shown in FIG. 1 represents the most preferred production process, according to which process the reaction proceeds easily in the presence of a Lewis acid as a catalyst, thereby ensuring safety in the synthesis and cheap production of the compounds of the present invention. When instead of the starting material in the diagram, i.e., Compound 201, the acetyl form, i.e., Compound 201 but with its chlorine atom replaced with an acetoxy group is allowed to react with a thioalcohol in the presence of $BF_3 \cdot ET_2O$ following the method by P. Sina et al. (Carbohydr. Res., 187(1989), 35–42), the compounds of the present invention can be produced as well. For separating the $\beta$-form from the final product in the diagram, if necessary, it is possible to utilize any conventional method, e.g., silica-gel chromatography. In the diagram of FIG. 1 is demonstrated the compound of the present invention whose R is $(CH_2)_{15}CH_3$, but naturally it can be exchanged for some other appropriate substituent.

FOURTH: The present invention relates to a method of producing compounds represented by the formula (XXXIII) which comprises allowing a compound represented by the general formula (XXXI) to react with an alcohol represented by the general formula (XXXII) in an inert solvent in the presence of a catalyst consisting of a Lewis acid alone or a combination of a Lewis acid and a tritylhalogenide.

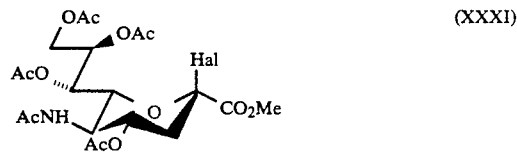

(XXXI)

wherein Hal represents a halogen atom.

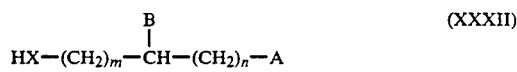

(XXXII)

wherein m and n each represent an integer of from 0 to 10, X, an oxygen or sulfur atom, A, a hydrogen atom, a linear or branched chain acylamino, alkyl, alkenyl, alkoxy, alkenyloxy or azido group with 10 to 40 carbon atoms, or an amino group protected with some protective group, and B, a hydrogen atom, m a linear or branched chain alkyl, alkenyl, alkoxy or alkenyloxy group with 10 to 30 carbon atoms, a lower alkoxycarbonyl group with 2 to 3 total carbon atoms, or a benzyloxycarbonyl group.

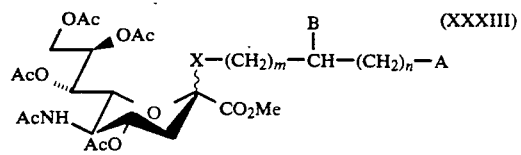

(XXXIII)

It should be noted that the formula (XXXIII) is the same as the above formula (XIII).

The present invention relates to a method enabling to produce sialic acid glycosides, which are rich in useful physiological activities, utilizing a safe and cheap catalyst.

Previously, as the catalyst for glycosylation of sialic acid derivatives, toxic mercury salts such as mercury (II) cyanide or mercury (II) bromide, or silver salts costly and problematic in handling such as silver perchlorate or silver trifluoromethanesulfonate have been used. In addition to the above metallic salts, there is an article that reports the use of zinc chloride as a metallic salt for glycosylation (E. Kirchner et al., J. Carbohydr. Chem., 7, 453 (1988)). In the article, however, glycosyl receptors are limited to strongly nucleophillic special reagents such as thiophenol, and no application is made to alcohols in general.

Accordingly, it has been generally desired to develop a glycosyl reaction of sialic acid in which a catalyst is used which is safe, cheap and industrially applicable.

An object of this invention lies in providing a production method of sialic acid glycosides by means of a catalyst safe in operation and low in cost.

In this production method, it is possible to use a variety of alcohols represented by the formula (XXXIV) instead of the alcohols represented by the formula (XXXII) for the reaction.

HO—A    (XXXIV)

In this formula, HO—A represents allyl alcohol, trimethylsilylethyl alcohol, cholesterol, a glycerol derivative represented by the formula (XXXV), a nucleoside derivative represented by the formula (XXXVI), a ceramide derivative represented by the formula (XXXVII), a pyranose derivative with its 6th hydroxyl group being unprotected represented by the formula (XXXVIII), and a pyranose derivative with its 3rd hydroxyl group being unprotected represented by the formula (XXXIX).

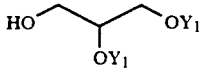   (XXXV)

in which $Y_1$ represents a linear or branched chain alkyl or alkenyl group with 12 to 40 carbon atoms, or a linear or branched chain acyl group with 12 to 40 carbon atoms which may have multiple bond(s).

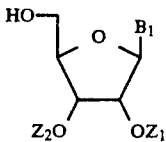   (XXXVI)

in which $Z_1$ and $Z_2$ represent protective groups for the hydroxyl group and $B_1$, a nucleic acid base.

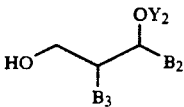   (XXXVII)

in which $Y_2$ represents a protective group for the hydroxyl group, $B_2$, an alkyl or alkenyl group with 10 to 20 carbon atoms, and $B_3$, an azido group, an amino group with protective group(s) or an acylamido group with 20 to 30 carbon atoms which may have multiple bond(s).

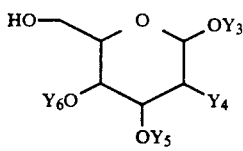   (XXXVIII)

in which $Y_3$ represents a protective group for the hydroxyl group or a sugar residue, $Y_4$, an axido group or a hydroxyl group either protected or unprotected, $Y_5$, a protective group for the hydroxyl group, and $Y_6$, a hydrogen atom or a protective group for the hydroxyl group.

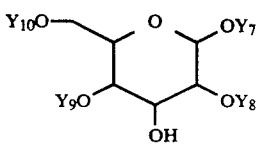   (XXXIX)

in which $Y_7$ represents a protective group for the hydroxyl group or a sugar residue, $Y_8$, a protective group for the hydroxyl group, $Y_9$, a hydrogen atom or a protective group for the hydroxyl group, and $Y_{10}$, a protective group for the hydroxyl group.

The halogen atom represented as Hal in the general formula (XXXI) can be a chlorine or bromine atom.

In the general formula (XXXVI), the nucleic acid base represented as $B_1$ can be adenine, guanine, cytosine, thymine etc. that may be substituted with fluorine atom(s). The protective groups for the hydroxyl group represented as $Z_1$ and $Z_2$ can be a lower acyl with 1 to 3 carbon atoms, a benzoyl, a benzyl, an isopropylidene, a benzylidene and such.

In the formula (XXXVII), the protective group for the hydroxyl group represented by $Y_2$ can be a benzyl, a benzoyl and such. The protective group for the amino group represented by $B_3$ can be a benzyloxycarbonyl, a trichloroethoxycarbonyl and such.

In the formula (XXXVIII), the protective group for the hydroxyl group represented by $Y_3$ can be a lower alkyl with 1 to 3 carbon atoms, an allyl, a benzyl, a trimethylsilylethyl and such, and the sugar residue can be a galactose, glucose, mannose, fucose, N-acetylglucosamine and such with the hydroxyl group protected by a lower acyl with 1 to 3 carbon atoms, a benzoyl, a benzyl, a trichloroethoxycarbonyl, a benzylidene, an isopropylidene and such. The protective groups for the hydroxyl group represented by $Y_4$, $Y_5$ and $Y_6$ can be a lower acyl with 1 to 3 carbon atoms, a benzoyl, a benzyl, a trichloroethoxycarbonyl, a benzylidene, an isopropylidene, and such.

In the formula (XXXIX), the protective group for the hydroxyl group represented by $Y_7$ can be a lower alkyl with 1 to 3 carbon atoms, an allyl, a benzyl, a trimethylsilylethyl and such, and the sugar residue can be a galactose, a glucose, a mannose, a fucose, an N-acetylglucosamine and such with the hydroxyl group protected by a lower acyl with 1 to 3 carbon atoms, a benzoyl, a benzyl, a trichloroethoxycarbonyl, a benzylidene, an isopropylidene and such. The protective groups for the hydroxyl group represented by $Y_8$, $Y_9$ and $Y_{10}$ can be a lower acyl with 1 to 3 carbon atoms, a benzoyl, a benzyl, a trichloroethoxycarbonyl, a benzylidene, an isopropylidene, and such.

Then explanation will be given of the production method of the starting materials for producing the sialic acid glycosides of the present invention.

First, regarding the production method of the sialic acid donors represented by the general formula (XXXI), those donors which have been most widely used can be easily prepared by a conventional method as in, e.g., R. Kuhn et al., Chem. Ber., 99, 611 (1966); H. Paulsen et al., Angew. Chem., Int. Ed. Engl., 21, 927 (1982); H. Paulsen et al., Carbohydr. Res., 125, 47 (1984); C. Shimizu et al., Chem. Pharm. Bull., 36, 1772 (1988); and H. Kunz et al., J. Chem. Soc., Chem. Commun., 638 (1985).

Then, the production method of the sialic acid receptors will be given.

Synthesis of the glycerol derivatives represented by the general formula (XXXV) can be easily achieved by a conventional method as in, e.g., M. Kates et al., Biochemistry, 2, 394 (1963); T. Ogawa et al., Agric. Biol. Chem., 46, 255 (1982); J. C. Sowden et al., J. Am. Chem. Soc., 63, 3244 (1941); and R. J. Howe et al., J. Chem. Soc., 2663 (1951).

The nucleoside derivatives represented by the general formula (XXXVI) can be produced by a conventional method as in, e.g., Ninth Symposium on Nucleic Acids Chemistry, Tokyo, Japan, October, 1981; Glycoconjugates, ed. by T. Yamakawa, T. Ogawa and S. Handa, Japan Scientific Societies Press, Tokyo, p. 481 (1981); and I. Kijima et al., Chem. Pharm. Bull., 30, 3278 (1982).

The ceramide derivatives represented by the general formula (XXXVII) can be synthesized by a conventional method as in, e.g., M. Kiso et al., J. Carbohydr. Chem., 5, 335 (1986); M. Kiso et al., Carbohydr. Res., 157, 101 (1986); K. Koike et al., Carbohydr. Res., 158, 113 (1986); and M. Kiso et al., J. Carbohydr. Chem., 6, 411 (1987).

The pyranose derivatives represented by the general formula (XXXVIII) can be synthesized by a conventional method as in, e.g., Y. Tsuda et al., Chem. Pharm. Bull., 31, 1612 (1983).

The pyranose derivatives represented by the general formula (XXXIX) can be synthesized by a conventional method as in, e.g., T. Ogawa et al., Carbohydr. Res., 135, C5 (1985).

Then, explanation will be given of the reaction conditions under which the production method of the sialic acid glycosides is carried out according to the present invention.

First, explanation will be given of the production method of the sialic acid derivatives represented by the general formula (XXXIII) which comprises reacting a sialic acid donor represented by the general formula (XXXI) with a sialic acid receptor represented by the general formula (XXXII) in an inert solvent in the presence of a Lewis acid alone as the catalyst.

The Lewis acid can be tin dichloride, tin dibromide, tin trifluoromethanesulfonate, zinc chloride, zinc bromide, zinc iodide, zinc trifluoromethanesulfonate, copper (II) chloride, copper (II) trifluoromethanesulfonate and such. Ordinarily, these Lewis acids are used at a ratio of 1 to 3 mol per 1 mol of a compound represented by the formula (XXXI).

A compound of the formula (XXXII) is used ordinarily at a ratio of 1 to 10 mol or preferably 1 to 2 mol with respect to 1 mol of a compound of the formula (XXXI).

As the dehydrating agent, Molecular sieves 4A, Molecular sieves AW300, Drierite and such can be used.

As the reaction solvent, those which are inert to Lewis acids, such as methylene chloride, ethylene dichloride, chloroform, acetonitrile, diethyl ether, benzene, toluene, and tetrahydrofuran, and preferably methylene dichloride and acetonitrile, should be used.

The reaction is usually carried out by maintaining the reaction mixture at a temperature between the water freezing point and the boiling point of the solvent for several hours to several days.

After completion of the reaction, the object product can be isolated by usual after-treatments such column chromatography for isolation.

Then, explanation will be given of the production method of the sialic acid derivatives represented by the general formula (XXXIII) which comprises reacting a sialic acid donor represented by the general formula (XXXI) with a sialic acid receptor represented by the general formula (XXXII) in an inert solvent in the presence of a Lewis acid combined with a tritylhalogenide as the catalyst.

The Lewis acid can be tin dichloride, tin dibromide, tin trifluoromethanesulfonate, zinc chloride, zinc bromide, zinc iodide, zinc trifluoromethanesulfonate, and such which generate trityl cations upon reacting with a trityl halogenide in the reaction system. These Lewis acids are used usually at a ratio of 1 to 3 mol or preferably 1 to 2 mol per 1 mol of a compound represented by the formula (XXXI). The trityl halogenide can be trityl chloride, trityl bromide or such, and these compounds are used usually at a ratio of 1 to 3 mol or preferably 1.5 to 2 mol with respect to 1 mol of a compound of the formula (XXXI).

A compound of the formula (XXXII) is used ordinarily at a ratio of 1 to 10 mol or preferably 1 to 2 mol with respect to 1 mol of a compound of the formula (XXXI).

As the dehydrating agent, Molecular sieves 4A, Molecular sieves AW300, Drierite or such can be used.

For the reaction, a solvent inert to Lewis acids should be used such as methylene chloride, ethylene dichloride, chloroform, acetonitrile, diethyl ether, benzene, toluene, tetrahydrofuran, and preferably methylene dichloride and acetonitrile.

The reaction is usually carried out by maintaining the reaction mixture at a temperature between the water freezing point and the boiling point of the solvent for several hours to several days.

After completion of the reaction, the object product can be isolated by usual after-treatments such as column chromatography.

The sialic acid glycosides obtained as described above and represented by the general formula (XXXIII) can be readily converted to compounds which have useful physiological activities to induce cell differentiation, regulate immunological response, inhibit tumorgrowth, inhibit tumor metastasis, produce anti-sialic acid monoclonal antibodies, and inhibit blood platelets aggregation, by methods described as in literature such as H. Ogura et al., Chem. Pharm. Bull., 35, 4043 (1987); T. Ogawa et al., Carbohydr. Res., 128, C1 (1984); A. Hasegawa et al., J. Carbohydr. Chem., 6, 411 (1987); H. Ogura et al., Chem. Pharm. Bull., 30, 3278 (1982); and H. Ogura et al., Chem. Pharm. Bull., 36, 914 (1988). Moreover, the compounds in question are useful as intermediates for producing a membrane constituent of a liposome which is difficult to capture by the reticuloendothelial system.

FIFTH: The present invention also relates to particulate carriers that comprise as their constituents at least one compound selected from the group of the sialic acid derivatives represented by the above general formulas (I), (VI), (XIII) or (XIIIa), or the following general formula (XXIa) and their salts.

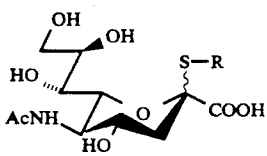
(XXIa)

in which R represents a linear or branched chain alkyl or alkenyl group.

R of the compounds is necessary for stably incorporating them into particulate carriers, and for achieving this function it is only necessary that R be an aliphatic chain, and a linear or branched chain alkyl or alkenyl group accordingly. R should be preferably $(CH_2)_nCH_3$ wherein n represents an integer of from 13 to 29, because with it the synthesis proceeds smoothly, and the cost is low.

In the formula (XXIa), ~ represents the α or β linkage. And, the salts can be, for example, the sodium salts.

The particulate carrier of this invention which comprises as a constituent at least one compound selected from the group consisting of the sialic acid derivatives represented by the formulas (I), (VI), (XIII), (XIIIa) or (XXIa), and their salts can be specifically be liposome, lipidmicrosphere, micelle, emulsion, or such.

For preparing these carriers, any appropriate conventional method can be employed, and this, in principle, consists of mixing compound(s) of the present invention with other membrane constituents, i.e., amphiphatic substance(s) through dissolution or dispersion.

Take the liposome as an example. A membrane constituent substance such as a phospholipid including phosphatidylcholine, sphingomyelin and phosphatidylethanolamine or a dialkyl type synthetic surfactant and a compound of this invention are first mixed, and the mixture is then subjected to a conventional method (for example, Ann. Rev. Biophys. Bioeng., 9, 467(1980)) to produce a liposome dispersion in water. Such liposome can contain, as a membrane stabilizing agent, a sterol such as cholesterol or a charged substance such as a dialkyl phosphate or stearylamine, and an anti-oxidant such as a tocopherol.

In the case of the lipidmicrosphere, phosphatidylcholine and a compound of this invention are first mixed, and the mixture is, after added with soybean oil, subjected to a conventional production method for lipidmicrosphere, whereby the object lipidmicrosphere is obtained.

In the case of the micelle, a surfactant such as a polyoxysorbitan fatty ester, a fatty acid sodium salt or polyoxyethylene-hardened castor oil and a compound of this invention are first mixed, and the mixture is then treated according to a conventional production for micelle, whereby the object micelle is obtained.

In the case of the emulsion, a surfactant such as a polyoxysorbitan fatty acid ester, a fatty acid sodium salt or polyoxyethylene-hardened castor oil and a compound of this invention are first mixed, and the mixture is, after added with fat(s) and/or oil(s) such as soybean oil, treated according to a conventional production method for emulsion, whereby the object emulsion is obtained.

For the particulate carrier of this invention prepared as above to have a property that allows itself to avoid capture by the reticuloendothelial system and to have a microcirculation in blood, a compound of this invention should usually be incorporated at a molar ratio of about 1/40 or more, or preferably about 1/20 or more with respect to all the lipid membrane constituents in the process of production.

Drugs such particulate carriers can retain vary depending upon the type of the carrier. For example, liposome can retain any drug without notable limitation, and it can retain lipid-soluble drugs as well as water-soluble ones. Lipid-soluble drugs are retainable by the lipidmicrosphere, micelle and emulsion.

More specifically, the drugs appropriate for the present purpose include anti-tumor agents represented by cytosine arabinoside and methotrexate, antibiotics represented by penicillin G, and physiologically active substances represented by insulin, interferon and tissue plasminogen activator (TPA).

BEST MODE FOR CARRYING OUT THE INVENTION

Figure 1:
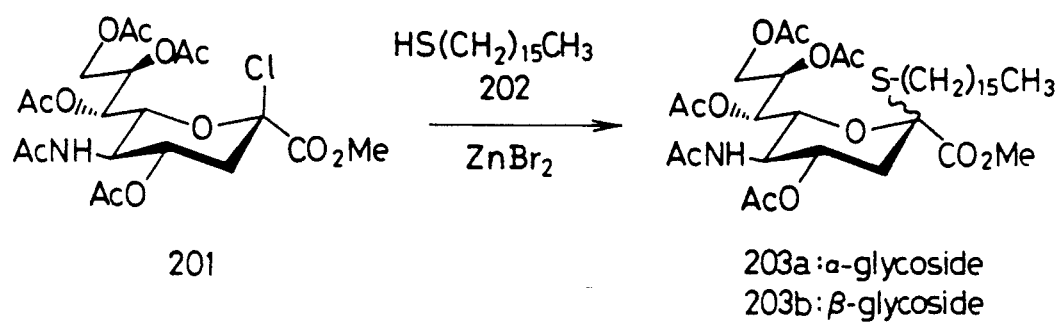
FIG. 1 shows a diagram of a synthesis process of the compounds of this invention represented by the general formula (XXI)
Figure 1:
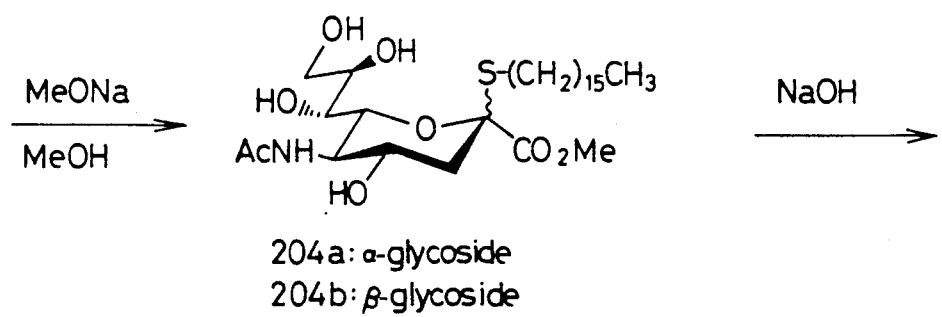
Figure 1:
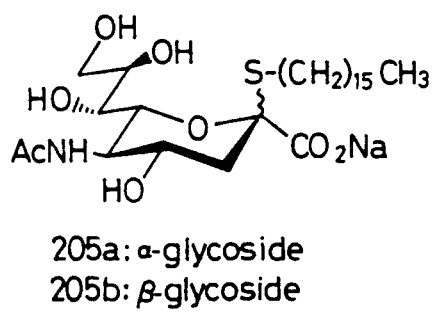

Example 1 Synthesis of 8-azido-1-octanol (Compound 1)

14.65 g of 1,8-octanediol was dissolved in 80 g of pyridine, and cooled to 10° C. A solution of 19 g p-toluenesulfonyl chloride in 70 ml anhydrous methylene chloride was added dropwise thereto, and the mixture was heated gradually overnight for reaction. After water washing, the solvent was removed by distillation, to produce an oily residue. The residue was dissolved in dimethylformamide to a 200 ml solution, to which was added 20 g of sodium azide, and the resultant mixture was maintained at 80° C. for 2 hours for reaction. The mixture was, after added with ethyl acetate, was washed with water 4 times and the solvent was removed by distillation. The object compound was isolated by silica-gel column-chromatography ($CHCl_3$-AcOEt 5:1-1:1) The yield was 6.07 g.

$^1H$-NMR($CDCl_3$)δ:3.64(t,2H), 3.26(t,2H), 1.6(m,4H), 1.35(m,8H).

Example 2
Methyl[2-(8-azido-1-octyl)-5-acetamido-4,7,8,9-tetra-0-acetyl-3,5-dideoxy-D-glycero-α-and-β-D-galacto-2-nonulopyranosid]onate (Compounds 2 and 3)

1.027 g of Compound 1 for the spacer group and 8 g of mercury (II) bromide, mercury (II) cyanide and powdered Molecular sieves 4A were mixed together with anhydrous methylene chloride, and stirred at 5° C. for 30 minutes. Then, a solution of 4 mmol methyl 5-acetamido-4,7,8,9-tetra-0-acetyl-2-chloro-2,3,5-trideoxy-D-glycero-β-D-galacto-2-nonulopyranosonate (Compound ii) dissolved in anhydrous methylene chloride was added dropwise at the same temperature, and the mixture was stirred at room temperature for 48 hours. The insoluble matter was celite-filtered out, and the filtrate and washings were concentrated under reduced pressure. Separation by silica-gel column-chromatography ((1) $CHCl_3$-MeOH 80:1, (2) $CHCl_3$-MeOH 70:1) was carried out, to isolate the glycoside compounds (Compounds 2 and 3).

Compound 2: $R_F=0.34$ ($CHCl_3$-MeOH 25:1).
$^1$H-NMR($CDCl_3$)δ:4.83(m, 1H), 4.32(dd, 1H), 2.58(dd, 1H).
MS(FD) m/z:645(M+1).
Compound 3: $R_F=0.41$ ($CHCl_3$-MeOH 25:1).
$^1$H-NMR($CDCl_3$)δ:2.46(dd, 1H).
MS(FD) m/z:645(M+1).

Example 3
Sodium[2-(8-palmitoylamido-1-octyl)-5-acetamido-3,5-dideoxy-D-glycero-α-D-galacto-2-nonulopyranosidonate (Compound 6)

149 mg of Compound 2 was dissolved in 3 ml of methanol. To the solution was added sodium methoxide (equivalent to 12 mg of sodium) dissolved in methanol, and the mixture was left overnight for reaction. Then, to the mixture was added 0.4 ml of 1N aqueous sodium hydroxide solution, and the mixture was stirred at room temperature overnight. The solution was neutralized with Amberlyst-15, to produce a compound with its ester group having been hydrolyzed (Compound 4). 96 mg. $R_F=0.39$ (n-BuOH-AcOH-$H_2O$ 2:1:1).

50 mg of Compound 4 was dissolved in 2 ml of methanol. To the solution was added 100 mg of a Lindlar catalyst. The mixture was left under 3 atm pressure for 6 hours for catalytic reduction, to produce an amine compound (Compound 5). $R_F=0.39$ (n-BuOH-AcOH-$H_2O$ 2:1:1).

45 mg of Compound 5 was dissolved in 1 ml of methanol. To the solution were added 55 mg of palmitic acid anhydride and 2 ml of tetrahydrofuran, and the mixture was left at room temperature overnight for reaction. To the mixture was, after having removed the methanol by distillation, added diethyl ether, the resultant mass was stirred thoroughly, and the solvent was removed by decantation. Then, purification by gel-column chromatography (LH 20, MeOH) was carried out, to produce a palmitoyl compound (Compound 6).

$R_F=0.69$ (n-BuOH-AcOH-$H_2O$ 2:1:1).
$[α]_D+2.9°$ (c 0.26, MeOH).
$^1$H-NMR($CD_3OD$)δ:2.83(dd, 1H), 2.51(t, 3H), 2.01(s, 3H), 0.90(t, 3H).
MS(SIMS) m/z:719(M+Na), 733(M+2Na).

Example 4 Sodium
[2-(8-palmitoylamido-1-octyl)-5-acetamido-3,5-dideoxy-D-glycero-β-D-galacto-2-nonulopyrnosid]onate (Compound 9)

The synthesis was performed completely in the same manner as in Example 3, except that Compound 2 was replaced with Compound 3.

Compound 7: $R_F=0.66$ (n-BuOH-AcOH-$H_2O$ 2:1:1).
Compound 8: $R_F=0.34$ (n-BuOH-AcOH-$H_2O$ 2:1:1).
Compound 9: $R_F=0.70$ (n-BuOH-AcOH-$H_2O$ 2:1:1),
$[α]_D -20°$ (c 0.35, MeOH).
$^1$H-NMR($CD_3OD$)δ:2.38(dd, 1H), 2.15(t, 3H), 1.98(s, 3H), 0.89(t, 3H).
MS(SIMS) m/z:719(M+Na).

Example 5 2,3-di-0-cetyl-D,L-glyceric acid (Compound 10)

8.2 g of DL-glyceraldehydediethylacetal was dissolved in 500 ml of dimethylformamide. To the solution was added 4.4 g of sodium hydride under ice cooling, and the mixture was stirred at room temperature for 30 minutes. To the resultant solution was added 30.5 g of cetyl bromide, and the mixture was left at room temperature overnight for reaction ($R_F=0.37$($PhCH_3$)). To the reaction solution consisting of two layers was added ethyl acetate and water, and the ethyl acetate layer was water-washed four times. After having removed the ethyl acetate by distillation, 500 ml of acetone and 9.8 g of p-toluenesulfonic acid were added to the residue, which was, then, subjected to reflux under heating for 2 hours ($R_F=0.40$($PhCH_3$)). After having removed about half amount of the acetone by distillation, ethyl acetate was added to the residue, and the mixture was water-washed twice. The ethyl acetate was removed by distillation, to produce 38.4 g of an oily residue.

38 g of the oil was dissolved in 450 ml of chloroform. To the solution was added 40 g of tetra-n-butylammonium permanganate, and the mixture was stirred at room temperature for 40 minutes. After having removed the precipitate formed by adding hexane, the solvent was replaced with ethyl acetate, and the resultant mass was washed with water. During washing, the solution is maintained at pH 2.0. Then, separation by silica-gel chromatography ($CHCl_3$-MeOH 100:1, 40:1) was carried out to isolate 14.5 g of a dl form compound (Compound 10). The yield was 52%. $R_F=0.32$($CHCl_3$-MeOH 10:1).

$^1$H-NMR($CDCl_3$)δ:3.48(m, 2H), 3.64(m, 2H), 3.71(dd, 1H), 3.80(dd, 1H), 4.04(dd, 1H).

Example 6 Sodium
[2-{2-(2,3-di-0-cetyl-DL-glyceroylamido)-1-ethtyl}-5-acetamido-3,5-dideoxy-D-glycero-β-D-galacto-2-nonulopyranosid]onate (Compound 12)

The compound 10 was conventionally converted to N-hydroxysuccinimide ester (Compound 11) and reacted with the amine compound (Compound 8) overnight in a mixed solvent of tetrahydrofuran and methanol (1:1). After having removed the solvent by distillation, hexane was added to the residue and the formed insoluble matter was removed. Separation by silica-gel column chromatography ($CHCl_3$-MeOH 20:1-5:1) was carried out to isolate the compound of interest. A minute presence of the N-hydroxy succinimide in the compound was removed by washing the compound dissolved in chloroform with water. The solution was solidified by addition of a small amount of methanol, to produce Compound 12.

$R_F=0.60$ ($CHCl_3$-MeOH-$H_2O$ 65:35:4).
$[α]_D -16.7°$ (c 0.3, $CHCl_3$).
$^1$H-NMR($CDCl_3$)δ:0.89(t, 6H), 2.07(s, 3H), 2.40(dd, 1H).
MS(Fab) m/z:996(M+Na), 1012(M+K).

Example 7
1,4-Di-[8-{sodium(5-acetamido-3,5-dideoxy-D-glycero-α-D-galacto-2-nonulopyranosyl)onate}oxy-1-octylcarbamoyl]-N-palmitoyl-2-s-butylamine (Compound 13)

1.0 g of L-glutamic acid α,γ-dibenzylester tosylate and N-(palmitoyloxy)succinimide was mixed and stirred in tetrahydrofuran at room temperature in the presence of triethylamine overnight for reaction. After concentration, the concentrate was submitted to silica-gel chromatography (PhCH$_3$-AcOEt 8:1), to produce 1.23 of an oily product. Then, after the benzyl moiety had been removed conventionally, N,N'-dicyclohexylcarbodiimide and N-hydroxy succucinimide were added thereto for reaction overnight in tetrahydrofuran. The tetrahydrofuran was removed by distillation, and the residue was dissolved in ethyl acetate. The solution was washed with water to produce an activated ester devoid of free N-hydroxysuccinimide.

0.06 mmol of the amine (Compound 5) and 0.03 mmol of the activated ester was mixed and stirred overnight in tetrahydrofuran at room temperature for reaction, to produce an oil. Separation with LH-20 (MeOH), followed by preparative chromatography (CHCl$_3$-MeOH-H$_2$O 65:30:4), to produce the sialic acid- containing glycolipid with two sialosugars (Compound 13).

R$_F$=0.14 (CHCl$_3$—MeOH—H$_2$O 65:30:4).
[α]$_D$+0.83° (c 0.6, CHCl$_3$—MeOH 1:1).
$^1$H-NMR(CDCl$_3$-CD$_3$OD 1:1)δ:0.89(t, 6H), 1.27(m), 2.05(s, 6H), 2.81(2xdd, 2H).

Example 8 2-Palmitoylamidoethanol (Compound 15)

2-Aminoethanol (Compound 14) (13.76 g, 225.3 mmol) was dissolved in chloroform (750 ml). To the solution was added dropwise palmitoyl chloride (15.48 g, 56.3 mmol), with stirring under ice cooling. After the dropwise addition, the mixture was stirred at room temperature for 19 hours. The reaction solution was washed with 10% aqueous citric acid, and the insoluble matter was removed by filtration. The separated organic layer was washed with water, dried with magnesium sulfate and concentrated under reduced pressure. The crystals thus obtained were washed with isopropyl ether, to produce the compound (Compound 15) as colorless crystals (13.50 g, 80%). mp, 98°-99° C.

$^1$H-NMR(CDCl$_3$)δ:0.88(t, 3H), 1.2-1.4(m, 24H), 1.64(quintet, 2H), 2.21(t, 2H), 3.43(q, 2H), 3.74(t, 2H), 5.96(br, s, 1H).

Example 9
2-Benzyloxycarbonyl-2-palmitoylamidoethanol (Compound 17)

The benzyl ester obtained conventionally from L-serine as a starting material (Compound 16) (15.69 g, 42.7 mmol) was dissolved in methylene chloride (250 ml). To the solution were added dropwise triethyl amine (8.64 g, 85.4 mmol) and palmitoyl chloride (10.56 g, 38.4 mmol) with stirring under ice cooling. After the dropwise addition, the mixture was stirred at room temperature for 5 hours. After completion of the reaction, the reaction solution was water washed, dried with magnesium sulfate, and concentrated under reduced pressure. The crystals thus obtained were washed with isopropyl ether, to produce the compound (Compound 17) as colorless crystals (8.76 g, 53%). mp, 84°-85° C.

[α]$_D$+7.9° (c 1.07, CHCl$_3$).
$^1$H-NMR(CDCl$_3$)δ:0.88(t, 3H), 1.2-1.4(m, 24H), 1.64(quintet, 2H), 2.26(t, 2H), 3.94(dd, 1H), 4.00(dd, 1H), 4.73(ddd, 1H), 5.22 and 5.23(ABq, 2H), 6.38(d, 1H), 7.3-7.4(m, 5H).

Example 10 Methyl
[2-(2-palmitoylamido-1-ethyl)-5-acetamido-4,7,8,9-tetra-O-acetyl-3,5-dideoxy-D-glycero-α-and-β-D-galacto-2-nonulopyranosidonate (Compounds 18 and 19)

A mixture of the alcohol compound (Compound 15) (632 mg, 2.11 mmol), silver carbonate (550 mg, 1.99 mmol), silver perchlorate (18 mg, 0.09 mmol) and powdered Molecular sieves 4A (315 mg) in methylene chloride (18 ml) was stirred at room temperature for 4.5 hours. On the other hand, a mixture of methyl 5-acetamido-4,7,8,9-tetra-O-acetyl-2-chloro-2,3,5-trideoxy-D-glycero-β-D-galacto-2-nonulopyranosonate (Compound ii) (500 mg, 0.98 mmol) and Molecular sieves 4A (260 mg) in methylene chloride (3 ml) was stirred at room temperature for 4 hours, and the resultant solution was added dropwise to the above mixture. Then, the mixture was stirred at room temperature for 19 hours. The insoluble matter was removed by filtration, and the filtrate and washings were concentrated under reduced pressure.

The residue was submitted to silica-gel column-chromatography (CHCl$_3$-MeOH 100:1) for separation. The chromatography treatment was repeated several times to isolate the α-isomer (Compound 18) (238 mg, 31%) and the β-isomer (Compound 19) (115 mg, 15%) in their pure state in the descending order of R$_F$.

Compound 18 (α-isomer):
$^1$H-NMR(CDCl$_3$)δ:0.88(t, 3H), 1.2-1.4(m, 24H), 1.6(m, 2H), 1.89, 2.04, 2.05, 2.14, 2.15(5s, 15H), 1.97(dd, 1H), 2.18(t, 2H), 2.58(dd, 1H), 3.4-3.5(m, 3H), 3.78(m, 1H), 3.81(s, 3H), 4.06(dd, 1H), 4.08(ddd, 1H), 4.15(dd, 1H), 4.31(dd, 1H), 4.86(ddd, 1H), 5.14(d, 1H), 5.33(dd, 1H), 5.38(ddd, 1H), 5.93(m, 1H).

Compound 19 (β-isomer):
$^1$H-NMR(CDCl$_3$)δ:0.88(t, 3H), 1.2-1.4(m, 24H), 1.6-1.7(m, 2H), 1.85(dd, 1H), 1.91, 2.02, 2.04, 2.07, 2.16(5s, 15H), 2.24(t, 2H), 2.45(dd, 1H), 3.4-3.5(m, 3H), 3.55-3.60(m, 1H), 3.81(s, 3H), 3.90(ddd, 1H), 4.08(dd, 1H), 4.13(dd, 1H), 4.73(dd, 1H), 5.19(ddd, 1H), 5.39(ddd, 1H), 5.39(dd, 1H), 5.61(d, 1H), 6.34(brs, 1H).

Example 11
[2-(2-palmitoylamido-1-ethyl)-5-acetamido-3,5-dideoxy-D-glycero-α-D-galacto-2-nonulopyranosidonate (Compound 20)

The acetoxy compound (Compound 18, 95 mg, 0.12 mmol) was dissolved in methanol (1 ml). To the solution was added 28% sodium methoxide (10 μl, 0.05 mmol) under ice cooling, and the mixture was stirred at the same temperature for 3 hours. To the resultant reaction solution was added acetic acid (7 mg, 0.12 mmol), and the mixture was concentrated under reduced pressure. To the residue was added ethyl acetate and water, and the separated organic layer was, after dried with magnesium sulfate, concentrated under reduced pressure. The residue was submitted to silica-gel column-chromatography (CHCl$_3$-MeOH 15:1) for purification, to produce the compound (Compound 20) as colorless crystals (40 mg, 53%).

mp 141°-142° C., [α]$_D$ −11.9° (c 0.80, MeOH).
$^1$H-NMR(CD$_3$OD)δ:0.88(t, 3H), 1.2-1.4(m, 24H), 1.57(m, 2H), 1.73(dd, 1H), 1.98(s, 3H), 2.17(t, 2H), 2.66(dd, 1H), 3.47(m, 1H), 3.48(dd, 1H), 3.56(dd, 1H), 3.60-3.66(m, 2H), 3.75(t, 1H), 3.80(s, 3H), 3.78-3.84(m, 3H).

Example 12 Sodium
[2-(2-palmitoylamido-1-ethyl)-5-acetamido-3,5-dideoxy-D-glycero-α-D-galacto-2-nonulopyranosidonate (Compound 21)

The methyl ester (Compound 20, 35 mg, 0.059 mmol) was dissolved in methanol (3 ml). To the solution was added 0.1N aqueous sodium hydroxide solution (585 μl ), and the mixture was stirred at room temperature for 48 hours. The resultant reaction solution was concentrated under reduced pressure, and the crystals thus obtained were washed with diethyl ether, to produce the compound (Compound 48) as colorless powder (36 mg, quant.).

$[\alpha]_D$ −2.6° (c 0.54, MeOH).

1H-NMR(CD$_3$OD)δ:0.89(t, 3H), 1.2–1.4(m, 24H), 1.6–1.7(m, 3H), 2.00(s, 3H), 2.19(t, 2H), 2.82(dd, 1H), 3.49(dd, 1H), 3.53(m, 1H), 3.57–3.62(m, 2H), 3.63–3.71(m, 2H), 3.77–3.88 (m, 3H).

MS(Fab) m/z:635(m+Na).

Example 13 Methyl [2-(2-palmitoylamido-1-ethyl)-5-acetamido-3,5-dideoxy-D-glycero-β-D-galacto-2-nonuluopyranosid]onate (Compound 22)

The acetoxy compound (Compound 19, 110 mg, 0.14 mmol) was dissolved in methanol (2 ml). To the solution was added 28% sodium methoxide (10 μl, 0.05 mmol) with stirring under ice cooling, and the mixture was further stirred at the same temperature for 2 hours. To the resultant reaction solution was added acetic acid (8 mg, 0.14 mmol), and the mixture was concentrated under reduced pressure. The residue was partitioned between the ethyl acetate layer and the aqueous layer. The organic layer was dried with magnesium sulfate and concentrated under reduced pressure. The residue was purified by silica-gel column chromatography (CHCl$_3$-MeOH 15:1), to produce the compound (Compound 22) as colorless crystals (39 mg, 45%).

mp 104°–106° C., $[\alpha]_D$ −8.8° (c 0.77, MeOH).

1H-NMR(CD$_3$OD)δ:0.88(t, 3H), 1.2–1.4(m, 24H), 1.58(m, 2H), 1.63(dd, 1H), 1.99(s, 3H), 2.17(t, 2H), 2.35(dd, 1H), 3.47(dd, 1H), 3.61(dd, 1H), 3.76(s, 3H), 3.84(dd, 1H), 4.01(ddd, 1H).

Example 14 Sodium [2-(2-palmitoylamido-1-ethyl)-5-acetamido-3,5-dideoxy-D-glycero-β-D-galacto-2-nonulopyranosid]onate (Compound 23)

The methyl ester (Compound 22, 37 mg, 0.062 mmol) was dissolved in methanol (3 ml). To the solution was added 0.1N aqueous sodium hydroxide solution (617 μl), and the mixture was stirred at room temperature for 48 hours. The resultant reaction solution was concentrated under reduced pressure, and the crystals thus obtained were washed with diethyl ether, to produce the compound (Compound 23) as colorless crystals (38 mg, quant.).

$[\alpha]_D$ −23.9° (c 0.70, MeOH).

1H-NMR(CD$_3$OD)δ:0.88(t, 3H), 1.2∼1.4(m, 24H), 1.5∼1.6(m, 3H), 1.96(s, 3H), 2.19(t, 2H), 2.36(dd, 1H), 3.40(d, 1H), 3.61(dd, 1H), 3.73(ddd, 1H), 3.79(dd, 1H), 3.84(d, 1H), 3.92(dd, 1H), 3.96(ddd, 1H).

MS(Fab) m/z:635(M+Na).

Example 15 Methyl [2-(2-benzyloxycarbonyl-2-palmitoylamido-1-ethyl)-5-acetamido-4,7,8,9-tetra-0-acetyl-3,5-dideoxy-D-glycero-α-and-β-D-galacto-2-nonulopyranosid]onate (Compounds 24 and 25)

A mixture of the alcohol (Compound 17, 850 mg, 1.96 mmol), silver carbonate (550 mg, 1.99 mmol), silver perchlorate (38 mg, 0.18 mmol) and powdered Molecular sieves 4A (315 mg) was stirred in methylene chloride (15 ml) at room temperature for 3 hours. On the other hand, a mixture of methyl 5-acetamido-4,7,8,9-tetra-0-acetyl-2-chloro-2,3,5-trideoxy-D-glycero-β-D-galacto-2-nonulopyranosonate (Compound ii, 500 mg, 0.98 mmol) and Molecular sieves 4A (260 mg) (6 ml) was stirred in methylene chloride at room temperature for 3 hours. The resultant solution was added dropwise to the above mixture. Then, the mixture was continuously stirred at room temperature for 3 days. The insoluble matter was filtered out using celite, and the filtrate and washings were concentrated under reduced pressure.

The residue was purified by silica-gel chromatography (CHCl$_3$-EtOH 200:1). The chromatography treatment was repeated several times to produce Compound 25 (β-isomer, 145 mg, 16%) and Compound 24 (α-isomer, 399 mg, 45%) in their pure state in the descending order of $R_F$.

Compound 24 (α-isomer):
1H-NMR(CDCl$_3$)δ:0.88(t, 3H), 1.2–1.4(m, 24H), 1.6–1.7(m, 2H), 1.89, 2.03, 2.04, 2.13, 2.14(5s, 15H), 1.90(m, 1H), 2.27(m, 2H), 2.52(dd, 1H), 3.71(s, 3H), 3.84(dd, 1H), 4.01(dd, 1H), 4.08(dd, 1H), 4.09(ddd, 1H), 4.11(dd, 1H), 4.25(dd, 1H), 4.79(ddd, 1H), 4.86(ddd, 1H), 5.12(d, 1H), 5.18 and 5.19(ABq, 2H), 5.33(dd, 1H), 5.36(ddd, 1H), 6.26(d, 1H), 7.3–7.4(m, 5H). Compound 25 (β-isomer):

mp 85°–87° C., $[\alpha]_D$ −17.8° (c 0.96, CHCl$_3$).

1H-NMR(CDCl$_3$)δ:0.88(t, 3H), 1.2–1.4(m, 24H), 1.6–1.7(m, 2H), 1.84(dd, 1H), 1.84, 1.99, 2.04, 2.10, 2.12 (5s, 15H), 2.27(t, 2H), 2.36(dd, 1H), 3.56(dd, 1H), 3.65(dd, 1H), 3.79(s, 3H), 3.99(dd, 1H), 4.03(ddd, 1H), 4.03(dd, 1H), 4.72(dd, 1H), 4.77(d, 1H), 4.86(ddd, 1H), 4.87(ddd, 1H), 5.16(d, 1H), 5.18(ddd, 1H), 5.24(dd, 1H), 5.46(d, 1H), 6.57(d, 1H), 7.3–7.5(m, 5H).

Example 16 Methyl[2-(2-palmitoylamido-2-tetradecylcarbamoyl-1-ethyl)-5-acetamido-4,7,8,9-tetra-0-acetyl-3,5-dideoxy-D-glycero-α-D-galacto-2-nenulopyranosid]onate (Compound 26)

The benzyl ester (Compound 24, 624 mg, 0.69 mmol) was dissolved in methanol (25 ml), and subjected to catalytic reduction in the presence of 10% Pd-C (155 mg) at room temperature under 3 atm. for 6.5 hours. After removing the catalyst by filtration, the filtrate and washings were concentrated under reduced pressure. The resultant carboxylic acid was dissolved in methylene chloride (50 ml). To the solution were added N-hydroxy succucinimide (79 mg, 0.69 mmol) and N,N'-dicyclohexylcarbodiimide (142 mg, 0.69 mmol), and the mixture was stirred at room temperature for 17.5 hours. To the reaction solution was added tetradecylamine (147 mg, 0.69 mmol), and the mixture was stirred for 23.5 hours. The insoluble matter was filtered out, and the filtrate and washings were combined and washed with water and dried with magnesium sulfate. Then, the solvent was removed by distillation under reduced pressure.

The residue was purified by silica-gel column-chromatography (CHCl$_3$-MeOH 100:1) to produce the compound (Compound 26) (516 mg, 74%).

$[\alpha]_D$ −5.9° (c 1.44, CHCl$_3$).

1H-NMR(CDCl$_3$)δ:0.86(2t, 6H), 1.2–1.4(m, 44H), 1.48(m, 2H), 1.62(m, 2H), 1.87, 2.01, 2.02, 2.11, 2.12(5s, 15H), 1.93(t, 1H), 2.22(m, 2H), 2.56(dd, 1H), 3.23(m, 2H), 3.76(d, 2H), 3.82(s, 3H), 4.05(ddd, 1H), 4.06(dd, 1H), 4.12(dd, 1H), 4.28(dd, 1H), 4.46(dt, 1H), 4.87(ddd, 1H), 5.13(d, 1H), 5.32(dd, 1H), 5.34(ddd, 1H), 6.32(d, 1H), 6.35(t, 1H).

Example 17 Methyl [2-(2-palmitoylamido-2-tetradecylcarbamoyl-1-ethyl)-5-acetamido-3,5-dideoxy-D-glycero-α-D-galacto-2-nonulopyranosid]onate (Compound 27)

The acetoxy compound (Compound 26, 486 mg, 0.48 mmol) was dissolved in methanol (5 ml). To the solution was added 28% sodium methoxide (23 µl, 0.12 mmol) with stirring under ice cooling. The mixture was stirred at the same temperature for 1 hour and further stirred at room temperature for 2 hours. To the resultant reaction solution was added acetic acid (29 mg, 0.47 mmol), and the mixture was concentrated under reduced pressure.

The residue was purified by silica-gel column-chromatography ($CHCl_3$-MeOH 20:1), to produce the compound (Compound 27) as colorless powder (248 mg, 61%).

mp 103°–104° C., $[\alpha]_D$ −13.5° (c 0.92, MeOH).

$^1$H-NMR($CD_3$ OD)δ:0.90(2t, 6H), 1.2–1.4(m, 46H), 1.49(m, 2H), 1.61(m, 2H), 1.74(dd, 1H), 2.00(s, 3H), 2.31(t, 2H), 2.64(dd, 1H), 3.19(m, 2H), 3.51(dd, 1H), 3.63(dd, 1H), 3.62–3.67(m, 2H), 3.75(dd, 1H), 3.78–3.83(m, 3H), 3.83(s, 3H), 4.01(dd, 1H), 4.40(dd, 1H).

Example 18 Sodium [2-(2-palmitoylamido-2-tetradecylcarbamoyl-1-ethyl)-5-acetamido-3,5-dideoxy-D-glycero-α-D-galacto-2-nonulopyranosidonate (Compound 28)

The methyl ester (Compound 27, 173 mg, 0.205 mmol) was dissolved in methanol (17 ml). To the solution was added 0.1N sodium hydroxide (2.05 ml), and the mixture was stirred at room temperature for 10 days. The resultant reaction solution was concentrated under reduced pressure, and the crystals thus obtained were washed with diethyl ether, to produce the compound (Compound 28) (169 mg, 97%).

$[\alpha]_D$ −9.4° (c 1.16, MeOH).

$^1$H-NMR($CD_3$ OD)δ:0.89(2t, 6H), 1.2–1 4(m, 46H), 1.48(m, 2H), 1.60(t, 1H), 1 57–1.64(m, 2H), 2.01(s, 3H), 2.32(t, 2H), 2.82(dd, 1H), 3.17(m, 2H), 3.51(dd, 1H), 3.60–3.65(m, 2H), 3.66–3.72(m, 2H), 3.75(dd, 1H), 3.80–3.86(m, 2H), 4.03(dd, 1H), 4.31(dd, 1H).

MS(Fab) m/z:852(M).

Example 1 Methyl [2-(2-palmitoylamido-2-tetradecylcarhamoyl-1-ethyl)-5-acetamido-4,7,8,9-tetra-0-acetyl-3,5 dideoxy-D-glycero-β-D-galacto-2-nonulopyranosid]onate (Compound 29)

The benzyl ester (Compound 25, 428 mg, 0.47 mmol) was dissolved in methanol (20 ml), and subjected to catalytic reduction in the presence of 10% Pd-C (110 mg) at room temperature under 3 atm. for 5 hours. After removing the catalyst by filtration, the filtrate and washings were concentrated under reduced pressure. The resultant carboxylic acid was dissolved in methylene chloride (20 ml). To the solution were added N-hydroxy succucinimide (54 mg, 0.47 mmol) and N,N'-dicyclohexylcarbodiimide (97 mg, 0.47 mmol), and the mixture was stirred at room temperature for 24 hours. To this reaction solution was added tetradecylamine (100 mg, 0.47 mmol), and the mixture was stirred for 24 hours. The insoluble matter was filtered out, and the filtrate and washings were combined and washed with water and dried with magnesium sulfate. Then, the solvent was removed by distillation under reduced pressure.

The residue was purified by silica-gel column-chromatography ($CHCl_3$-MeOH 100:1) to produce the compound (Compound 29) (329 mg, 69%).

$[\alpha]_D$ −10.5° (c 1.29, $CHCl_3$).

$^1$H-NMR($CDCl_3$)δ:0.88(2t, 6H), 1.2–1.4(m, 44H), 1.51(m, 2H), 1.66(m, 2H), 1.87(dd, 1H), 1.90, 2.00, 2.02, 2.08, 2.15(5s, 15H), 2.30(m, 2H), 2.38(dd, 1H), 3.25(dt, 2H), 3.36(dd, 1H), 3.81(s, 3H), 4.03(dd, 1H), 4.12(ddd, 1H), 4.21(dd, 1H), 4.55(dd, 1H), 4.75(dd, 1H), 5.15(ddd, 1H), 5.26(ddd, 1H), 5.45(dd, 1H), 6.32(d, 1H), 6.61(t, 1H), 6.68(d, 1H).

Example 20 Methyl [2-(2-palmitoylamido-2-tetradecylcarbamoyl-1-ethyl)-5-acetamido-3,5-dideoxy-D-glycero-β-D-galacto-2-nonulopyranosid]onate (Compound 30)

The acetoxy compound (Compound 29, 320 mg, 0.32 mmol) was dissolved in methanol (3 ml). To the solution was added 28% sodium methoxide (15 µl, 0.08 mmol) with stirring under ice cooling. The mixture was further stirred at the same temperature for 3 hours. To the resultant reaction solution was added acetic acid (21 mg, 0.35 mmol), and the mixture was concentrated under reduced pressure.

The residue was purified by silica-gel column-chromatography ($CHCl_3$-MeOH 20:1), to produce the compound (Compound 30) as colorless powder (184 mg, 69%). mp 130°–131° C.

$[\alpha]_D$ −15.2° (c 0.73, MeOH).

$^1$H-NMR($CD_3$ OD)δ: 0.90(2t, 6H), 1.2–1.4(m, 46H), 1.50(m, 2H), 1.61(m, 2H), 1.67(dd, 1H), 2.01(s, 3H), 2.28(t, 2H), 2.37(dd, 1H), 3.19(t, 2H), 3.49; (dd, 1H), 3.49(dd, 1H), 3.62(dd, 1H), 3.77(t, 1H), 3.79(s, 3H), 3.80–3.84(m, 2H), 3.83(dd, 1H), 3.98(dd, 1H), 3.98(ddd, 1H), 4.46(t, 1H).

Example 21 Sodium [2-(2-palmitoylamido-2-tetradecylcarbamoyl-1-ethyl)-5-acetamido-3,5-dideoxy-D-glycero-β-D-galacto-2-nonulopyranosid]onate (Compound 31)

The methyl ester (Compound 30, 168 mg, 0.199 mmol) was dissolved in methanol (6 ml). To the solution was added 0.1N aqueous sodium hydroxide solution (1.99 ml), and the mixture was stirred at room temperature for 3 days. The resultant reaction solution was concentrated under reduced pressure, and the crystals thus obtained were washed with diethyl ether, to produce the compound (Compound 31) (156 mg, 92%).

$[\alpha]_D$ −4.0° (c 0.73, MeOH).

$^1$H-NMR($CD_3$ OD)δ:0.90(2t, 6H), 1.2~1.4(m, 46H), 1.51(m, 2H), 1.62(dd, 1H), 1.58~1.66(m, 2H), 1.98(s, 3H), 2.32(m, 2H), 2.36(dd, 1H), 3.15(m, 1H), 3.25(m, 1H), 3.41(d, 1H), 3.46(dd, 1H), 3.62(dd, 1H), 3.75(ddd, 1H), 3.76(d, 1H), 3.82(dd, 1H), 3.83(ddd, 1H), 3.94(t, 1H), 4.02(dd, 1H), 4.23(t, 1H).

MS(Fab) m/z:852(M).

Example 22 2-Benzyloxycarbonylamidoethanol (Compound 32)

2-Aminoethanol (Compound 14, 6.74 g, 110.3 mmol) and triethylamine (11.17 g, 110.3 mmol) were dissolved in methylene chloride (400 ml). To the solution was added N-carbobenzoxyoxysuccinimide (25.00 g, 100.3 mmol) under ice cooling. Then, the mixture was stirred at room temperature for 3 hours. The reaction solution was washed with water, 5% aqueous sodium hydrogen carbonate solution, water, 10% aqueous citric acid solution, and water in that order, and dried with magnesium

Example 23 Methyl [2-(2-benzyloxycarbonylamido-1-ethyl)-5-acetamido-4,7,8,9-tetra-O-acetyl-3,5-dideoxy-D-glycero-α-and-β-D-galacto-2-nonulopyranosid]onate (Compounds 33 and 34)

A mixture of the alcohol (Compound 32, 383 mg, 1.96 mmol), silver carbonate (550 mg, 1.99 mmol), silver perchlorate (18 mg, 0.09 mmol) and powdered Molecular sieves 4A (315 mg) was stirred in methylene chloride (10 ml) at room temperature for 4.5 hours. On the other hand, a mixture of methyl 5-acetamido 4,7,8,9-tetra-O-acetyl-2-chloro-2,3,5-trideoxy-D-glycero-β-D-galacto-2 -nonulopyranosonate (Compound ii, 500 mg, 0.98 mmol) and Molecular sieves 4A (260 mg) was stirred in methylene chloride (5 ml) at room temperature for 4 hours, and the resultant solution was added dropwise to the above mixture. Then, the resultant mixture was stirred at room temperature for 3 days. The insoluble matter was removed by celite filtration, and the filtrate and washings were concentrated under reduced pressure.

The residue was purified by silica-gel column-chromatography (CHCl$_3$-(CH$_3$)$_2$CO-AcOEt 5:1:1), and further purified by silica-gel column-chromatography ((CH$_3$)$_2$CO-nC$_6$H$_{12}$ 1:2), to produce a mixture of the α- and β-isomers (281 mg, 43%).

Compound 33 (α-isomer):
$^1$H-NMR(CDCl$_3$)δ:1.87, 2.01, 2.02, 2.05, 2.12(5s, 15H), 1.92(dd, 1H), 2.54(dd, 1H), 3.4-3.5(m, 3H), 3.75(s, 3H), 3.78(m, 1H), 4.02(ddd, 1H), 4.04(dd, 1H), 4.14(dd, 1H), 4.26(dd, 1H), 4.84(ddd, 1H), 5.09(br s, 2H), 5.14(d, 1H), 5.19(br s, 1H), 5.28(dd, 1H), 5.38(ddd, 1H), 7.3-7.4(m, 5H).

Example 24 Methyl [2-(2-benzyloxycarbonylamido-1-ethyl)-5-acetamido-3,5-dideoxy-D-glycero-α-D-galacto 2-nonulopyranosid]onate (Compound 35)

The acetoxy compound (Compound 33:Compound 34=10:1, 241 mg, 0.36 mmol) was dissolved in methanol (3 ml). To the solution was added 28% sodium methoxide (15 μl, 0.08 mmol) with stirring under ice cooling. The mixture was further stirred at the same temperature for 3 hours. To the resultant reaction solution was added acetic acid (22 mg, 0.36 mmol), and the mixture was concentrated under reduced pressure.

The residue was purified by silica-gel column-chromatography (CHCl$_3$-MeOH 15:1), to produce the compound (Compound 35) as colorless powder (96 mg, 53%).

mp 136°-137° C., [α]$_D$ −10.6° (c 0.63, MeOH).
$^1$H-NMR(CD$_3$ OD)δ:1.74(dd, 1H), 1.99(s, 3H), 2.67(dd, 1H), 3.27(t, 2H), 3.49(m, 1H), 3.50(dd, 1H), 3.58(dd, 1H), 3.60-3.63(m, 2H), 3.77(dd, 1H), 3.79(s, 3H), 3.78-3.84(m, 2H), 3.82(dd, 1H), 5.06 and 5.07(ABq, 2H), 7.2-7.4(m, 5H).

Example 25 Methyl [2-aminoethyl-5-acetamido-4,7,8,9-tetra-O-acetyl-3,5-dideoxy-D-glycero-α-D-galacto-2-nonulopyranosid]onate hydrochloride (Compound 36)

The Z-compound (Compound 35, 77 mg, 0.15 mmol) was dissolved in methanol (20 ml). To the solution was added 0.1N hydrochloric acid (2 ml, 0.20 mmol), and the mixture was subjected to catalytic reduction in the presence of 10% Pd-C (22 mg) at room temperature under 3 atm. for 4 hours. After removing the catalyst by filtration, the filtrate and washings were concentrated under reduced pressure, to produce the compound (Compound 36) (62 mg, quant.)

Example 26 1-0-(Methyl 5-acetamido-4,7,8,9-tetra-O-acetyl-3,5-dideoxy-D-glycero-α-D-galacto-2-nonulopyranosylonate)-2-[2-(methyl 5-acetamido-3,5-dideoxy-D-glycero-α-D-galacto-2-nonulopyranosylonate)oxy-1-ethylcarbamoyl]-2-(palmitoylamido)ethanol (Compound 37)

The benzyl ester compound (Compound 24, 140 mg, 0.15 mmol) was dissolved in methanol (6 ml), and subjected to catalytic reduction in the presence of 10% Pd-C (40 mg) at room temperature under 3 atm. for 6.5 hours. After removing the catalyst by filtration, the filtrate and washings were concentrated under reduced pressure. The resultant carboxylic acid was dissolved in methylene chloride (15 ml). To the solution were added N-hydroxysuccucinimide (19 mg, 0.17 mmol) and N,N'-dicyclohexylcarbodiimide (32 mg, 0.16 mmol), and the mixture was stirred at room temperature for 24 hours. This reaction solution and triethylamine (16 mg, 0.15 mmol) were added to the amine (Compound 36, 62 mg, 0.15 mmol), and the mixture was stirred at room temperature for 5 days. The insoluble matter was filtered out, and the filtrate and washings were combined and concentrated under reduced pressure.

The residue was purified by silica-gel column-chromatography (CHCl$_3$-MeOH 25:1, 15:1) to produce the compound (Compound 37) (57 mg, 32%).

[α]$_D$ −10.2° (c 1.22, MeOH).
$^1$H-NMR(CD$_3$ OD)δ:0.90(t, 3H), 1.2-1.4(m, 24H), 1.64(m, 2H), 1.75(dd, 1H), 1.83, 1.98, 1.99, 2.00, 2.09, 2.14(6s, 18H), 1.89(dd, 1H), 2.31(t, 2H), 2.63(dd, 1H), 2.69(dd, 1H), 3.84(2s, 6H), 3.95(dd, 1H), 3.97(t, 1H), 4.09(dd, 1H), 4.14(dd, 1H), 4.27(dd, 1H), 4.53(t, 1H), 4.81(m, 1H), 5.34(dd, 1H), 5.41(ddd, 1H).

Example 27 1-0-(Methyl 5-acetamido-3,5-dideoxy-D-glycero-α-D-galacto-2-nonulopyranosylonate)-2-]2-(methyl 5-acetamido-3 5-dideoxy-D-glycero-α-D-galacto-2-nonulopyranosylonate)-oxy-1-ethylcarbamoyl]-2-(palmitoylamido) ethanol (Compound 38)

The acetoxy compound (Compound 37, 48 mg, 0.04 mmol) was dissolved in methanol (4 ml. To the solution was added 28% sodium methoxide (2 μl ) with stirring under ice cooling. The mixture was further stirred at the same temperature for 2.5 hours. To the resultant reaction solution was added acetic acid (40 μl ), and the mixture was concentrated under reduced pressure.

The residue was purified by silica-gel column-chromatography (CHCl$_3$-MeOH 5:1, 3:1), to produce the compound (Compound 38) (36 mg, 88%).

[α]$_D$ −12.7° (c 0.88, MeOH).

Example 28 1-0-(Sodium 5-acetamido-3,5-dideoxy-D-glycero-α-D-galacto-2-nonulopyranosylonate)-2-[2-(sodium 5-acetamido-3,5-dideoxy-D-glycero-α-D-galacto-2-nonulopyranosylonate)oxy-1-ethylcarbamoyl]-2-(palmitoylamido) ethanol (Compound 39)

The methyl ester (Compound 38, 31 mg, 0.03 mmol) was dissolved in methanol (4 ml). To the solution was added 0.1N aqueous sodium hydroxide solution (0.62 ml), and the mixture was stirred at room temperature for 18 days. The resultant reaction solution was concentrated under reduced pressure, and the crystals thus obtained were washed with diethyl ether, to produce the compound (Compound 39) (28 mg, 90%).

$^1$H-NMR(CD$_3$ OD)δ:0.89(t, 3H), 1.2–1.4(m, 24H), 1.5~1.7(m, 4H), 2.01(2s, 6H), 2.3–2.4(m, 2H), 2.85(m, 2H).

Ms(Fab) m/z:1035(M+Na).

(Example 29 Synthesis of 2-palmitoleoylamido-ethanol (Compound 40)

498 mg of N-hydroxysuccinimide and 892 mg of dicyclohexylcarbodiimide were added to palmitoleic acid dissolved in methylene chloride (16 ml), and the mixture was stirred at room temperature for 4 hours. The dicyclohexyl urea crystallized was filtered. After adding with 0.6 ml of ethanolamine, the mixture was stirred overnight at room temperature. After water washing and drying, the solvent was removed by distillation. The residue was purified by silica-gel column chromatography (CHCl$_3$-MeOH 20:1), to produce the side chain alcohol (Compound 40) approximately quantitatively.

$R_F$=0.33 (CHCl$_3$-MeOH 10:1).

$^1$H-NMR(CDC13)δ:0.86(t, 3H), 1.19–1.36(m, 16H), 1.58~1.66(m, 2H), 1.96–2.02(m, 4H), 2.19(t, 2H), 2.52(bs, 1H), 3.41(q, 2H), 3.71(t, 2H), 5.27–5.38(m, 2H), 5.85(bs, 1H).

Example 30 Methyl [2-(2-palmitoleoylamido-1-ethyl)-5-acetamido-4,7,8,9-tetra-0-acetyl-3,5-dideoxy-D-glycero-α-and-β-D-galacto-2-nonulopyranosid]onate (Compounds 41 and 42)

To 1 g of Molecular sieves 4A (dried by heating overnight under reduced pressure) dissolved in methylene chloride (15 ml) were added 1.74 g of silver carbonate, 38 mg of silver perchlorate and 827 mg of the alcohol (Compound 40), and the mixture was stirred under an argon atmosphere at room temperature for 6 hours, to which was added a solution of 1.5 g of the 2-chloro derivative of sialic acid (Compound ii) and 0.7 g of the molecular sieves dissolved in methylene chloride (10 ml), which solution had been stirred at room temperature for 4 hours. The resultant mixture was stirred at room temperature for 18 hours. After completion of the reaction, the reaction mixture was filtered with celite, and the solvent was removed by distillation under reduced pressure. The residue was subjected to silica-gel column-chromatography (CHCl$_3$-MeOH 100:1) for purification, to produce Compound 41 (α form) and Compound 42 (β form) in amounts of 724 mg and 484 mg, respectively. The yields were 34% and 23%, respectively. Compound 41 (α form):

$R_F$=0.20 (CHCl$_3$-MeOH 25:1).

$[\alpha]_D$ −15.9° (c 0.82, CHCl$_3$).

$^1$H-NMR(CDCl$_3$)δ:0.88(t, 3H), 1.23–1.37(m, 16H), 1.58–1.66(m, 2H), 1.92(dd, 1H), 2.01(s, 3H), 2.03(s, 3H), 2.04(s, 3H), 2.14(s, 6H), 1.97–2.21(m, 6H), 2.57(dd, 1H), 3.37–3.51(m, 3H), 3.72–3.79(m, 1H), 3.80(s, 3H), 4.03(dd, 1H), 4.05(ddd, 1H), 4.15(dd, 1H), 4.31(dd, 1H), 4.86(ddd, 1H), 5.17(d, 1H), 5.30–5.40(m, 3H), 5.34(ddd, 1H), 5.91(m, 1H).

Compound 42 (β form):

$R_F$=0.18 (CHCl$_3$-MeOH 25:1).

$[\alpha]_D$ −6.1° (c 1.41, CHCl$_3$).

$^1$H-NMR(CDCl$_3$)δ:0.88(t, 3H), 1.20–1.37(m, 16H9), 1.55–1.68(m, 2H), 1.84(dd, 1H), 1.91(s, 3H), 1.96–2.07(m, 4H), 2.02(s, 3H), 2.04(s, 3H), 2.07(s, 3H), 2.16(s, 3H), 2.23(t, 2H), 2.45(dd, 1H), 3.40–3.60(m, 4H), 3.81(s, 3H), 3.91(ddd, 1H), 4.08(dd, 1H), 4.13(dd, 1H), 4.74(dd, 1H), 5.18(ddd, 1H), 5.28–5.41(m, 4H), 5.72(d, 1H), 6.24–6.31(m, 1H).

Example 31 Methyl [2-(2-palmitoleoylamido-1-ethyl)-5-acetamido-3,5-dideoxy-D-glycero-α-D-galacto-2-nonulopyranosid]onate (Compound 43)

To a solution of 382 mg of Compound 41 (α form) dissolved in methanol (5 ml) was added 50 μl of sodium methoxide (28% NaOMe in MeOH), and the mixture was stirred at room temperature for 1 hour. The solution was concentrated under reduced pressure and the residue was purified by silica-gel column-chromatography (CHCl$_3$-MeOH 10:1), to produce 234 mg of the deacetylated compound (Compound 43). The yield was 78%.

$R_F$=0.48 (CHCl$_3$-MeOH 5:1).

$[\alpha]_D$ −22.4° (c 0.83, CHCl$_3$).

$^1$H-NMR(CDCl$_3$+1 drop CD$_3$ OD):0.90(t, 3H), 1.20–1.38(m, 16H), 1.55–1.64(m, 2H), 1.88(dd, 1H), 1.97–2.05(m, 4H), 2.07(s, 3H), 2.20(t, 2H), 2.78(dd, 1H), 3.38–3.44(m, 2H), 3.46–3.53(m, 2H), 3.57(d, 1H), 3.65(ddd, 1H), 3.75(dd, 1H), 3.85(s, 3H), 3.78–3.93(m, 4H), 5.30–5.40(m, 2H).

Example 32 Methyl [2-(2-palmitoleoylamido-1-ethyl)-5-acetamido-3,5-dideoxy-D-glycero-β-D-galacto-2-nonulopyranosid]onate (Compound 44)

To a solution of 346 mg of Compound 42 (β form) dissolved in methanol (4 ml) was added 40 μl of sodium methoxide (28% NaOMe in MeOH), and the mixture was stirred at room temperature for 5 hours. The solution was concentrated under reduced pressure and the residue was purified by silica-gel column-chromatography (CHCl$_3$-MeOH 20:1), to produce 169 mg of the deacetylated compound (Compound 44). The yield was 63%.

$R_F$=0.49 (CHCl$_3$-MeOH 5:1).

$[\alpha]_D$ −22.7° (c 0.78, CHCl$_3$).

$^1$H-NMR(CDCl$_3$+1 drop CD$_3$ OD):0.87(t, 3H), 1.20–1.37(m, 16H), 1.54–1.64(m, 2H), 1.69(dd, 1H), 1.95–2.03(m, 4H), 2.03(s, 3H), 2.17(t, 2H), 2.38(dd, 1H), 3.29–3.50(m, 4H), 3.68–3.85(m, 6H), 3.79(m, 3H), 3.94–4.03(m, 1H), 5.29–5.38(m, 2H).

Example 33 Sodium [2-(2-palmitoleoylamido-1-ethyl)-5-acetamido-3,5-dideoxy-D-glycero-α-D-galacto-2-nonulopyranosid]onate (Compound 45)

To 92 mg of the methyl ester (Compound 43) dissolved in methanol (4 ml) was added an equivalent thereto of 0.1N aqueous sodium hydroxide solution, and the mixture was stirred at room temperature for 43 hours. The solvent was removed by distillation under reduced pressure, to produce Compound 45 as white powder in a stoichiometric amount.

$R_F$=0.33 (BuOH-AcOH-H$_2$O 2:1:1).
$[\alpha]_D$ −3.2° (c 10.6, MeOH).
$^1$H-NMR(CD$_3$ OD)δ:0.90(t, 3H), 1.23–1.40(m, 16H), 1.55–1.65(m, 2H), 1.60(dd, 1H), 1.98–2.08(m, 4H), 2.01(s, 3H), 2.20(t, 2H), 2.38(dd, 1H), 3.25–3.37(m, 2H), 3.50(dd, 1H), 3.51–3.57(m, 1H), 3.60(dd, 1H), 3.61(ddd, 1H), 3.80–3.88(m, 3H), 5.32–5.37(m, 2H).
MS(Fab) m/z:611(M+1), 633(M+Na)

Example 34 Sodium [2-(2-palmitoleoylamido-1-ethyl)-5-acetamido-3,5-dideoxy-D-glycero-β-D-galacto-2-nonulopyranosidonate (Compound 46)

To the methyl ester (Compound 44) (115 mg) dissolved in methanol (4 ml) was added an equivalent thereto of 0.1N aqueous sodium hydroxide solution, and the mixture was stirred at room temperature for 43 hours. The solvent was removed by distillation under reduced pressure, to produce Compound 46 in a stoichiometric amount.

$R_F$=0.30 (BuOH-AcOH-H$_2$O 2:1:1).
$[\alpha]_D$ −24.0° (c 0.86, MeOH).
$^1$H-NMR(CD$_3$ OD)δ:0.90(t, 3H), 1.23–1.40(m, 16H), 1.56–1.66(m, 2H), 1.62(dd, 1H), 1.98(s, 3H), 1.99–2.08(m, 4H), 2.21(t, 2H), 2.38(dd, 1H), 3.21–3.28(m, 1H), 3.33–3.41(m, 2H), 3.43(d, 1H), 3.64(dd, 1H), 3.70–3.76(m, 2H), 3.80(dd, 1H), 3.84(d, 1H), 3.90(dd, 1H), 3.98(ddd, 1H), 5.30–5.38(m, 2H).
MS(Fab) m/z:611(M+1), 633(M+Na).

Example 35 Dibenzyl dicetylmalonate (Compound 47)

To a solution of 1.55 g of sodium hydride (60%, NaH) dissolved in dimethylformamide (20 ml) were added 11.83 g of 1-bromohexadecane and 5.00 g of the dibenzyl ester of malonic acid, and the mixture was stirred at room temperature for 42 hours. To the resultant reaction solution were added water and ethyl acetate for extraction, and the organic layer was dried. The solvent was removed form the organic layer by distillation under reduced pressure. The residue was purified by silica-gel column-chromatography (n-C$_6$H$_{12}$-AcOEt 100:1), to produce 2.23 g of the dialkyl compound (Compound 47). The yield was 17%.

$R_F$=0.45 (C$_6$H$_{12}$-AcOEt 10:1).
$^1$H-NMR(CDCl$_3$)δ:0.88(t, 6H), 1.13–1.35(m, 56H), 1.83–1.92(m, 4H), 5.10(s, 4H), 7.24–7.34(m, 10H).

Example 36 2-Cetyl-octadecanoic acid (Compound 48)

To a solution of 1.14 g of the dialkyl compound (Compound 47) dissolved in 31 ml of a mixed solvent of ethanol and toluene (30:1) was added 100 mg of 10% Pd-C, and the mixture was subjected to catalytic reduction at room temperature for 2.5 hours (H$_2$, 1 atm.). After having removed the catalyst by filtration, the filtrate was concentrated under reduced pressure to produce 770 mg of a dicarboxylic acid ($R_f$=0.73, CHCl$_3$-MeOH 3:1), and the heating of the dicarboxylic acid at 150° C. for 50 minutes produced 700 mg of a monocarboxylic acid compound (Compound 48). The yield was 88%.

$R_F$=0.77 (CHCl$_3$-MeOH 20:1, CHCl$_3$-C$_6$H$_{12}$ 2:1).
$^1$H-NMR(CDCl$_3$)δ:0.88(t, 3H), 1.06–1.35(m, 56H), 1.42–1.51(m, 2H), 1.57–1.67(m, 2H), 2.31–2.41(m, 1H).

Example 37 Sodium [8-(2-cetyl-octadecanamido)octyl-5-acetamido-3,5-dideoxy-D-glycero-α-D-galacto-2-nonulopyranosidonate (Compound 49)

Compound 48 and N-hydroxysuccinimide were conventionally allowed to react to produce an activated ester. 70 mg of the activated ester and 50 mg of Compound 5 were allowed to react in a mixed solvent of toluene and methanol (1:1) in the presence of sodium hydrogencarbonate overnight at room temperature.

After having removed the solvent by distillation, the residue was purified by gel column-chromatography (LH-20, MeOH), to produce 65 mg of Compound 49.

$R_F$=0.89 ($^n$BuOH-AcOH-H$_2$O 2:1:1).
MS(Fab) m/z:949(M+1), 971(M+Na).
$^1$H-NMR(CDCl$_3$:CD$_3$OD=1:1):0.90(m, 6H), 2.05(s, 3H), 2.73(dd, 1H).

Example 38 Sodium [8-(2-cetyl-octadecanamido)octyl-5-acetamido-3,5-dideoxy-D-glycero-β-D-galacto-2-nonulopyranosid]onate (Compound 50)

Compound 48 and N-hydroxysuccinimide were conventionally allowed to react to produce an activated ester. 70 mg of the activated ester and 50 mg of Compound 8 were allowed to react in a mixed solvent of toluene and methanol (1:1) in the presence of sodium hydrogencarbonate overnight at room temperature.

After having removed the solvent by distillation, the residue was purified by gel column-chromatography (LH-20, MeOH) to produce 60 mg of Compound 50.

$R_F$=0.89 ($^n$BuOH-AcOH-H$_2$O 2:1:1).
MS(Fab) m/z:949(M+1), 971(M+Na).
$^1$H-NMR(CDCl$_3$ CD$_3$OD=1:1):0.89(m, 6H), 2.03(s, 3H), 2.45(dd, 1H).

Example 39 Disodium [2-(2-carboxylato-2-palmitoylamido-1-ethyl)-5-acetamido-3,5-dideoxy-D-glycero-α-D-galacto-2-nonulopyranosid]onate (Compound 51)

The diester (Compound 24, 91 mg, 0.1 mmol) was dissolved in methanol (5 ml). To the solution was added 0.1N sodium hydroxide (6 ml), and the mixture was stirred at room temperature for 10 days. The resultant reaction solution was concentrated under reduced pressure and the residue was purified by separation with LH-20 (methanol), to produce the compound (Compound 51) (60 mg, 88%).

$R_F$=0.30 (CHCl$_3$-MeOH-H$_2$O 65:30:4).
1H-NMR(CD$_3$ OD)δ:0.89(t, 3H), 2.00(s, 3H), 2.80(dd, 1H).

Example 40 Disodium [2-(2-carboxylato-2-palmitoylamido-1-ethyl)-5-acetamido-3,5-dideoxy-D-glycero-β-D-galacto 2-nonulopyranosidonate (Compound 52)

The diester (Compound 25, 91 mg, 0.1 mmol) was treated in the same manner as in Example 39 to produce the compound (Compound 52) (61 mg, 90%).

$R_F$=0.35 (CHCl$_3$-MeOH-H$_2$O 65:30:4).

$^1$H-NMR(CD$_3$OD)δ:0.90(t, 3H), 1.99(s, 3H), 2.37(dd, 1H).

Example 41 Methyl (2-cetyl-5-acetamido-4,7,8,9-tetra-O-acetyl-3,5-dideoxy-D-glycero-α-and-β-D-galacto-2-nonulopyranosid)onate (Compounds 53 and 54)

To 1.5 g of a molecular sieves (MS 4A) (dried by heating overnight under reduced pressure) suspended in dichloromethane (50 ml) were added 1.08 g of silver carbonate, 27 mg of silver perchlorate and 950 mg of cetyl alcohol, and the mixture was stirred under an argon atmosphere at room temperature for 4 hours, to which was added a solution of 1.0 g of the 2-chloro derivative of sialic acid (Compound ii) and 0.7 g of MS in dichloromethane (10 ml), which solution had been stirred at room temperature for 3 hours. The resultant mixture was stirred at room temperature for 20 hours. After completion of the reaction, the reaction mixture was filtered with celite, and the solvent was removed by distillation under reduced pressure. The residue was subjected to silica-gel column-chromatography (CHCl$_3$-MeOH 100:1) for purification, to produce the α form (Compound 53) and the β form (Compound 54) in amounts of 225 mg and 75 mg, respectively. The yields were 16% and 5%, respectively.

α form (Compound 53):
R$_F$=0.44 (CHCl$_3$-MeOH 25:1).
[α]$_D$ −14.6° (c 0.81, CHCl$_3$).
$^1$H-NMR(CDCl$_3$)δ:0.88(t, 3H), 1.16-1.37(m, 26H), 1.48-1.57(m, 2H), 1.88(s, 3H), 1.95(dd, 1H), 2.03(s, 3H), 2.04(s, 3H), 2.14(s, 3H), 2.15(s, 3H), 2.58(dd, 1H), 3.20(dt, 1H), 3.75(dt, 1H), 3.79(s, 3H), 4.03-4.14(m, 3H), 4.31(dd, 1H), 4.83(ddd, 1H), 5.16(d, 1H), 5.33(dd, 1H), 5.39(ddd, 1H).

β form (Compound 54):
R$_F$=0.41 (CHCl$_3$-MeOH 25:1).
[α]$_D$ −11.6° (c 0.88, CHCl$_3$).
$^1$H-NMR(CDCl$_3$)δ:0.88(t, 3H), 1.30-1.37(m, 26H), 1.53-1.60(m, 2H), 1.86(dd, 1H), 1.89(s, 3H), 2.02(s, 3H), 2.03(s, 3H), 2.07(s, 3H), 2.15(s, 3H), 2.46(dd, 1H), 3.30(dt, 1H), 3.45(dt, 3H), 3.80(s, 3H), 3.92(dd, 1H), 4.12(ddd, 1H), 4.13(dd, 1H), 4.79(dd, 1H), 5.18(ddd, 1H), 5.23(d, 1H), 5.25(ddd, 1H), 5.40(dd, 1H).

Example 42 Methyl (2-cetyl-5-acetamido-3,5-dideoxy-D-glycero-α-D-galacto-2-nonulopyranosid)onate (Compound 55)

To 55 mg of the α form (Compound 53) dissolved in methanol (1 ml) was added 10 μl of sodium methoxide (28% NaOMe in MeOH), and the mixture was stirred at room temperature for 1 hour. The resultant mixture was concentrated under reduced pressure and the residue was purified by silica-gel column-chromatography (CHCl$_3$-MeOH 10:1), to produce 35 mg of the deacetylated compound (Compound 55). The yield was 83%.
R$_F$=0.49 (CHCl$_3$-MeOH 5:1).
[α]$_D$ −3.3° (c 1.03, MeOH$_3$).
$^1$H-NMR(CD$_3$OD)δ:0.89(t, 3H), 1.25-1.36(m, 26H), 1.48-1.55(m, 2H), 1.72(dd, 1H), 1.99(s, 3H), 2.67(dd, 1H), 3.32(dt, 2H), 3.50(dd, 1H), 3.54(dd, 1H), 3.61(ddd, 1H), 3.63(dd, 1H), 3.74(dd, 1H), 3.76(dt, 1H), 3.83(s, 3H), 3.80-3.87(m, 2H).

Example 43 Methyl (2-cetyl-5-acetamido-3,5-dideoxy-D-glycero-β-D-galacto-2-nonulopyranosid)onate (Compound 56)

To 181 mg of the β form (Compound 54) dissolved in methanol (2 ml) was added 20 μl of sodium methoxide (28% NaOMe in MeOH), and the mixture was stirred at room temperature for 1 hour. The mixture was concentrated under reduced pressure and the residue was purified by silica-gel column-chromatography (CHCl$_3$-MeOH 20:1), to produce 93 mg of the deacetylated compound (Compound 56). The yield was 67%.
R$_F$=0.47 (CHCl$_3$-MeOH 5:1).
[α]$_D$ −20.2° (c 1.11, MeOH).
$^1$H-NMR(CD$_3$OD)δ:0.89(t, 3H), 1.22-1.41(m, 26H), 1.49-1.57(m, 2H), 1.61(dd, 1H), 2.00(s, 3H), 2.37(dd, 1H), 3.17(dt, 1H), 3.49(dd, 1H), 3.65(dd, 1H), 3.73(dt, 1H), 3.78(s, 3H), 3.77-3.85(m, 4H), 4.01(ddd, 1H).

Example 44 Sodium (2-cetyl-5-acetamido-3,5-dideoxy-D-glycero-α-D-galacto-2-nonulopyranosid)onate (Compound 57)

To 29.5 mg of the methyl ester (Compound 55) dissolved in methanol (2 ml) was added an equivalent thereto of 0.1N NaOH, and the mixture was stirred at room temperature for 109 hours. The solvent was removed by distillation under reduced pressure, to produce a white powder (Compound 57) in a stoichiometric amount.
R$_F$=0.16 (BuOH-AcOH-H$_2$O 2:1:1).
$^1$H-NMR(CD$_3$OD)δ:0.90(t, 3H), 1.21-1.38(m, 26H), 1.47-1.56(m, 2H), 1.56(dd, 1H), 2.01(s, 3H), 2.82(dd, 1H), 3.45(dt, 1H), 3.50(dd, 1H), 3.56(dd, 1H), 3.62(dd, 1H), 3.65(dd, 1H), 3.69(ddd, 1H), 3.75(dt, 1H), 3.82(dd, 1H), 3.86(ddd, 1H).

Example 45 Sodium (2-cetyl-5-acetamido-3,5-dideoxy-D-glycero-β-D-galacto-2-nonulopyranosid)onate (Compound 58)

To 80 mg of the methyl ester (Compound 56) dissolved in methanol (5 ml) was added an equivalent thereto of 0.1N NaOH, and the mixture was stirred at room temperature for 109 hours. The solvent was removed by distillation under reduced pressure, to produce a white powder (Compound 58) in a stoichiometric amount.
R$_F$=0.14 (BuOH-AcOH-H$_2$O 2:1:1).
[α]$_D$ −25.6° (C 0.50, MeOH).
$^1$H-NMR(CD$_3$OD)δ:0.90(t, 3H), 1.22-1.37(m, 26H), 1.53-1.61(m, 2H), 1.56(dd, 1H), 1.98(s, 3H), 2.39(dd, 1H), 3.30(dt, 1H), 3.43(d, 1H), 3.54(dt, 1H), 3.65(dd, 1H), 3.76(ddd, 1H), 3.79(dd, 1H), 3.81(dd, 1H), 8.91(dd, 1H), 3.97(ddd, 1H).

It should be noted here that all the optical rotations when referred to in this specification were measured at 25° C. unless otherwise indicated with a Perkin-Elmer Model 241 MC polarimeter. For silica-gel chromatography was used silica-gel 60 provided by Nacalai Tesque. The TLC plate was Silica-Gel F$_{254}$ (Merck, Darmstadt) 0.25 mm, 0.5 mm. For $^1$H-NMR was used a VXR-500S, and for mass spectrometric analysis, a Hitachi M-80A or JEOL JMS-HX110.

Then, preparation examples of particulate carriers will be given using the compounds provided by this invention.

Control Example 1

70 μmol of L-α-dipalmitoylphosphatidyl choline, 70 μmol of cholesterol and 3.5 μmol of dicetyl phosphate were dissolved in a mixture of chloroform and methanol (2:1 volume ratio). Then, lipid film was generated on the glass wall of a centrifuge tube by removing the organic solvent in nitrogen flow. To the tube was poured 7 ml of 1 mM inulin solution dissolved in phosphate buffer saline (pH 7.4, hereinafter referred to as PBS), said inulin containing 140 μCi of $^3$H-inulin, and the tube was shaken. The mass was subjected lightly to ultrasonic treatment, to produce a liposome suspension. The suspension was heated to 45°-60° C., and passed through a polycarbonate membrane filter with the pore size being 0.08 μm, to produce a liposome suspension having a particle size of about 0.08 μm. The suspension was subjected to ultracentrifugation (100,000×g, 1 hour and three times). Rejection of the supernatant effected removal of the inulin not bound to the liposomes. To the residue was added PBS, to produce 5 ml in total of liposome suspension for which the inulin was retained only in the aqueous phase of the liposomes.

When assayed by an enzyme method using as the marker the choline group of L-α-dipalmitoylphosphatidyl choline, the suspension obtained above contained 9.1 μmol of the phospholipid per 1 ml.

Control Example 2

Using the same prescription as in Control Example 1 except the use of 7 μmol of ganglioside $GM_1$ instead of dicetyl phosphate produced 5 ml in total of liposome suspension.

The suspension thus obtained contained 10.0 μmol of the phospholipid per 1 ml.

Preparation Example 1

Using the same prescription as in Control Example 1 except the use of 7 μmol of Compound 21 instead of dicetyl phosphate produced 5 ml in total of liposome suspension.

The suspension thus obtained contained 14.0 μmol of the phospholipid per 1 ml.

Preparation Example 2

Using the same prescription as in Control Example 1 except the use of 7 μmol of Compound 23 instead of dicetyl phosphate produced 5 ml in total of liposome suspension.

The suspension thus obtained contained 17.3 μmol of the phospholipid per 1 ml.

Preparation Example 3

Using the same perscription as in Control Example 1 except the use of 7 μmol of Compound 45 instead of dicetyl phosphate produced 5 mil in total of liposome suspension.

The suspension thus obtained contained 9.3 μmol of the phospholipid per 1 ml.

Preparation Example 4

Using the same prescription as in Control Example 1 except the use of 7 μmol of Compound 45 instead of dicetyl phosphate produced 5 ml in total of liposome suspension.

The suspension thus obtained contained 8.5 μmol of the phospholipid per 1 ml.

Preparation Example 5

Using the same prescription as in Control Example 1 except the use of 7 μmol of Compound 6 instead of dicetyl phosphate produced 5 ml in total of liposome suspension.

The suspension thus obtained contained 8.4 μmol of the phospholipid per 1 ml.

Preparation Example 6

Using the same prescription as in Control Example 1 except the use of 7 μmol of Compound 9 instead of dicetyl phosphate produced 5 ml in total of liposome suspension.

The suspension thus obtained contained 8.4 μmol of the phospholipid per 1 ml.

Preparation Example 7

Using the same prescription as in Control Example 1 except the use of 7 μmol of Compound 58 instead of dicetyl phosphate produced 5 ml in total of liposome suspension.

The suspension thus obtained contains 8.1 μmol of the phospholipid per 1 ml.

Finally, application examples (test examples) of the particulate carriers of this invention will be described.

Test Example 1

Each of liposome suspensions prepared as in Control Examples 1 and 2, and Preparation Examples 1 to 7 was injected via a cannula that had been cannulated into the jugular vein of an SD strain male rat (weighing 240–300 g) at a dose of 2.5 μmol in terms of L-α-dipalmitoylphosphatidyl choline per 100 g body weight.

At each of 30 minutes, 1 hour, 2 hours, 4 hours, 6 hours and 24 hours after the injection, about 0.2 ml of blood was sampled through the cannula, and centrifuged to separate the plasma. About 100 μl of the plasma was placed on a sheet of filter paper, dried and burnt with a burner. The radioactivity of the residue was assayed by the liquid scintillation method, and the inulin concentration in blood was calculated according to the following formula;

Concentration in blood (%)={inulin content/ml (plasma)}/(inulin dosage per one rat)×100.

In addition, 24 hours after the injection the rat was killed, and its liver and spleen were each taken out by about 400 mg, and the bone marrow, by about 50 mg. They were each dried and burnt with a burner, and their radioactivity was assayed by the liquid scintillation method. The partition coefficient ($K_p$) between tissue and plasma was calculated according to the following formula;

Tissue/plasma partition coefficient ($K_p$) =

{inulin concentration (% of dose) per 1 g of tissue}/

{inulin concentration (% of dose) per 1 ml of plasma}

The test results are listed in Tables 1 and 2.

As is evident from Table 1, the liposome containing a compound of this invention had a higher blood concentration than the control liposome or the $GM_1$ containing liposome, thus suggesting improved microcirculation in blood. Also as is evident from Table 2, the liposome containing a compound of this invention had Kp's significantly lower than the control liposome and GM₁ containing liposome, for liver, spleen and bone marrow, thus suggesting its being more resistant to capture by the reticuloendothelial system.

From the above results it was confirmed that the sialic acid containing glycolipid derivatives, i.e., the compounds of this invention are useful as a constituent of particulate carriers represented by liposome.

TABLE 1

TRANSITION OF THE PLASMA CONCENTRATION OF INULIN AS THE AQUEOUS PHASE MARKER OF LIPOSOME
(% of dose/ml, average ±SE, repeated three times)

| | Compound | 30 min. | 1 hr. | 2 hrs. |
|---|---|---|---|---|
| Cont. Ex. 1 | Control | 3.90 ± 0.49 | 2.45 ± 0.26 | 1.80 ± 0.30 |
| Cont. Ex. 2 | Ganglioside GM₁ | 4.14 ± 0.98 | 2.36 ± 0.15 | 0.91 ± 0.33 |
| Prep. Ex. 1 | 21 | 5.28 ± 0.26 | 5.79 ± 0.70 | 5.18 ± 0.07 |
| Prep. Ex. 2 | 23 | 7.34 ± 0.11 | 7.96 ± 0.38 | 7.22 ± 0.14 |
| Prep. Ex. 3 | 45 | 5.59 ± 0.19 | 5.39 ± 0.26 | 4.78 ± 0.25 |
| Prep. Ex. 4 | 46 | 5.04 ± 0.46 | 5.02 ± 0.40 | 4.58 ± 0.26 |
| Prep. Ex. 5 | 6 | 4.03 ± 0.03 | 3.69 ± 0.23 | 3.47 ± 0.18 |
| Prep. Ex. 6 | 9 | 5.87 ± 0.33 | 4.33 ± 0.57 | 4.05 ± 0.32 |
| Prep. Ex. 7 | 58 | 5.52 ± 0.53 | 4.73 ± 0.14 | 4.75 ± 0.17 |
| | Compound | 4 hrs. | 6 hrs. | 24 hrs. |
| Cont. Ex. 1 | Control | 1.63 ± 0.08 | 1.28 ± 0.10 | 0.32 ± 0.04 |
| Cont. Ex. 2 | Ganglioside GM₁ | 0.46 ± 0.08 | 0.16 ± 0.04 | 0.09 ± 0.001 |
| Prep. Ex. 1 | 21 | 4.23 ± 0.20 | 3.67 ± 0.15 | 0.74 ± 0.22 |
| Prep. Ex. 2 | 23 | 5.89 ± 0.41 | 5.03 ± 0.34 | 0.96 ± 0.17 |
| Prep. Ex. 3 | 45 | 4.17 ± 0.32 | 3.47 ± 0.25 | 0.81 ± 0.05 |
| Prep. Ex. 4 | 46 | 3.89 ± 0.17 | 3.35 ± 0.12 | 1.22 ± 0.09 |
| Prep. Ex. 5 | 6 | 3.04 ± 0.05 | 2.64 ± 0.09 | 0.87 ± 0.03 |
| Prep. Ex. 6 | 9 | 3.85 ± 0.31 | 3.46 ± 0.13 | 1.03 ± 0.07 |
| Prep. Ex. 7 | 58 | 3.75 ± 0.07 | 3.33 ± 0.06 | 0.98 ± 0.33 |

TABLE 2

PARTITION COEFFICIENT (Kp) BETWEEN TISSUE AND PLASMA 24 HOURS AFTER LIPOSOME INJECTION
(average ±SE, repeated three times)

| | Compound | Liver | Spleen | Bone marrow |
|---|---|---|---|---|
| Cont. Ex. 1 | Control | 10.33 ± 0.36 | 188.54 ± 40.91 | 8.51 ± 1.22 |
| Cont. Ex. 2 | Ganglioside GM₁ | 52.53 ± 4.55 | 405.27 ± 60.12 | 23.95 ± 3.81 |
| Prep. Ex. 1 | 21 | 4.58 ± 0.87 | 55.35 ± 20.08 | 3.16 ± 1.03 |
| Prep. Ex. 2 | 23 | 3.29 ± 0.83 | 29.76 ± 6.67 | 2.49 ± 0.35 |
| Prep. Ex. 3 | 45 | 2.69 ± 0.24 | 32.75 ± 1.99 | 2.42 ± 0.35 |
| Prep. Ex. 4 | 46 | 1.28 ± 0.20 | 17.44 ± 1.37 | 1.31 ± 0.11 |
| Prep. Ex. 5 | 6 | 2.16 ± 0.16 | 38.05 ± 2.46 | 1.27 ± 0.13 |
| Prep. Ex. 6 | 9 | 1.64 ± 0.15 | 42.50 ± 3.63 | 0.91 ± 0.02 |
| Prep. Ex. 7 | 58 | 3.63 ± 1.07 | 46.90 ± 9.65 | 1.69 ± 0.20 |

Example 101 Synthesis of methyl [2-(8-azidooctyl)-5-acetamido-1,7,8,9-tetra-0-acetyl-3,5-dideoxy-D-glycero-β-D-galacto-2-nonulopyranosidonate (Compound 101)

To a mixture of 0.5 g of a molecular sieves (AW-300, ex Gas-chro Industry Co.), 8-azidooctanol (193 mg), the β-acetyl derivative (202 mg) and methylene chloride (10 ml), said β-acetyl derivative being represented by the formula (XI) where the OAc at the 2nd position has the β-linkage, was added tin tetrachloride (56 μl, 0.479 mmol), and the mixture was stirred at room temperature for 33 hours. After completion of the reaction, the mixture was diluted with methylene chloride, and celite-filtered to remove the AW-400. The filtrate was neutralized with an equivalent amount of aqueous sodium hydrogencarbonate solution, and the insoluble matter was removed by celite filtration. After separating the aqueous layer, the organic layer was dried and the solvent was removed by distillation under reduced pressure.

The residue was purified by silica-gel column-chromatography ($CHCl_3$-MeOH 100:1), to produce 196.9 mg of the β isomer (Compound 101). The yield was 81%.

$R_F$=0.41 ($CHCl_3$-MeOH 25:1).

$[α]_D$ −11.5° (c 1.01, $CHCl_3$).

$^1$H-NMR($CDCl_3$)δ(ppm) in 500 MHz:1.26–1.42(m, 8H), 1.51–1.65(m, 4H), 1.86(dd, 1H), 1.88(s, 3H), 2.02(s, 3H), 2.03(s, 3H), 2.07(s, 3H), 2.14(s, 3H), 2 46(dd, 1H), 3.27(t, 2H), 3.31(dt, 1H), 3.47(dt, 1H), 3.80(s, 3H), 3.92(dd, 1H), 4.11(ddd, 1H), 4.12(dd, 1H), 4.80(dd, 1H), 5.19(ddd, 1H), 5.23(d, 1H), 5.25(ddd, 1H), 5.39(dd, 1H).

IR(KBr)cm$^{-1}$: 2100, 1747, 1685, 1663, 1373, 1230, 1038.

MS(FD) (m/Z):645(M+1).

Incidentally, the α isomer gives the following measurements;

$R_F$=0.34 ($CHCl_3$-MeOH 25:1).

$[α]_D$ −15.1° (c 0.81, $CHCl_3$).

$^1$H-NMR($CDCl_3$)δ(ppm) in 500 MHz:27–1.40(m, 8H), 1.50–1.64(m, 4H), 1.88(s, 3H), 1.95(dd, 1H), 2.03(s, 3H), 2.05(s, 3H), 2.14(s, 3H), 2.15(s, 3H), 2.58(dd, 1H), 3.21(dt, 1H), 3.26(t, 2H), 3.75(dt, 1H), 3.80(s, 3H), 4.06(ddd, 1H), 4.08(dd, 1H), 4.10(dd, 1H), 4.31(dd, 1H), 4.84(ddd, 1H), 5.11(d, 1H), 5.33(dd, 1H), 5.40(ddd, 1H).

IR(KBr)cm$^{-1}$: 2100, 1747, 1688, 1663, 1373, 1231, 1038.

MS(FD) (m/Z):645(M+1).

EXAMPLES 102–108

The same reaction as in Example 101 was repeated several times under the reaction conditions as indicated in Table 101, and the results are also listed in Table 101.

TABLE 101

| Example | Linkage of OAc at the 2nd position | Lewis acid catalyst | Amount of catalyst used per 1 mol of the starting 2-acetyl sialic acid (mol) | Dehydrating agent |
|---|---|---|---|---|
| 102 | β | $SnCl_4$ | 4.5 | Molecular sieves AW-300 |
| 103 | α | $SnCl_4$ | 4.7 | Molecular sieves AW-300 |
| 104 | β | $SnCl_4$ | 4.6 | Anhydrous $CaSO_4$ |
| 105 | β | $SnCl_4$ | 1.3 | None |
| 106 | β | $SnCl_4$ | 4.5 | Molecular sieves AW-300 |
| 107 | β | $SnCl_4$ | 4.6 | Molecular sieves AW-300 |
| 108 | β | $BF_3 \cdot Et_2O$ | 4.3 | Molecular sieves 4A |

| Example | Reaction solvent | Reaction time (hr.) | Yield (%) | Ratio of α isomer vs. β isomer in target product |
|---|---|---|---|---|
| 102 | $CH_2Cl_2$ | 4 | 59 | 0:100 |
| 103 | $CH_2Cl_2$ | 2.5 | 51 | 0:100 |
| 104 | $CH_2Cl_2$ | 2.5 | 43 | 0:100 |
| 105 | $CH_2Cl_2$ | 6 | 71 | 4:96 |

TABLE 101-continued

| 106 | CH$_3$CN | 3.5 | 65 | 18:82 |
| 107 | Et$_2$O | 24 | 15 | 15:85 |
| 108 | CH$_2$Cl$_2$ | 144 | 57 | 0:100 |

Example 109 Synthesis of methyl [2-cetyl-5-acetamido-4,7,8,9-tetra-0-acetyl-3,5-dideoxy-D-glycero-β-D-galacto-2-nonulopyranosid]onate (Compound 102)

To a mixture of 0.5 g of a molecular sieves (AW-300), cetyl alcohol (273 mg), the β-acetyl derivative (200 mg) and methylene chloride (10 ml) was added tin tetrachloride (56 μl, 0.479 mmol), and the mixture was stirred at room temperature for 30 hours. After completion of the reaction, the mixture was diluted with methylene chloride, and celite-filtered to remove the AW-400. The filtrate was neutralized with an equivalent amount of aqueous sodium hydrogencarbonate solution, and the insoluble matter was removed by celite filtration. After separating the aqueous layer, the organic layer was dried and the solvent was removed by distillation under reduced pressure.

The residue was purified by silica-gel column-chromatography (CHCl$_3$-MeOH 100:1), to produce 179.9 mg of the β isomer (Compound 102). The yield was 67%.

R$_F$=0.41 (CHCl$_3$-MeOH 25:1).

[α]$_D$ −11.6° (c 0.88, CHCl$_3$).

$^1$H-NMR(CDCl$_3$)δ(ppm) in 500 MHz:0.88(t, 3H), 1.30–1.37(m, 26H), 1.53–1.60(m, 2H), 1.86(dd, 1H), 1.89(s, 3H), 2.02(s, 3H), 2.07(s, 3H), 2.15(s, 3H), 2.46(dd, 1H), 3.30(dt, 1H), 3.45(dt, 3H), 3.80(s, 3H), 3.92(dd, 1H), 4.12(ddd, 1H), 4.13(dd, 1H), 4.79(dd, 1H), 5.18(ddd, 1H), 5.23(d, 1H), 5.25(ddd, 1H), 5.40(dd, 1H).

IR(Neat)cm$^{-1}$:1747, 1661, 1371, 1224.

Example 110 Synthesis of methyl [2-(2-palmitoylamido)ethyl-5-acetamido-4,7,8,9-tetra-0-acetyl-3,5-dideoxy-D-glycero-β-D-galacto-2-nonulopyranosid]onate (Compound 103.

To a mixture of 0.25 g of a molecular sieves (4A, made by Nacalai Tesque Co.), 2-palmitoylamido ethanol (168 mg), the β-acetyl derivative (100 mg) and methylene chloride (20 ml) was added boron trifluoride ether complex salt (208 μl ), and the mixture was stirred at room temperature for 14 days. After completion of the reaction, the mixture was diluted with methylene chloride, and the molecular sieves (4A) was removed by celite filtration. The solvent was removed by distillation under reduced pressure.

The residue was purified by silica-gel column-chromatography (CHCl$_3$-EtOH 60:1), to produce 58.6 mg of the β isomer (Compound 103). The yield was 40%.

R$_F$=0.10 (CHCl$_3$-Me$_2$CO-AcOEt 5:5:1).

$^1$H-NMR(CDCl$_3$)δ(ppm) in 500 MHz:0.88(t, 3H), 1.2–1.4(m, 24H), 1.6–1.7(m, 2H), 1.85(dd, 1H), 1.91(s, 3H), 2.02(s, 3H), 2.04(s, 3H), 2.07(s, 3H), 2.16(s, 3H), 2.24(t, 2H), 2.45(dd, 1H), 3.40–3.50(m, 3H), 3.55–3.60(m, 1H), 3.81(s, 3H), 3.90(ddd, 1H), 4.08(dd, 1H), 4.13(dd, 1H), 4.73(dd, 1H), 5.19(ddd, 1H), 5.39(ddd, 1H), 5.39(dd, 1H), 5.61(dd, 1H), 6.34(br s, 1H).

Example 111 Synthesis of methyl [2-(2-benzyloxycarhonyl-2-palmitoylamido)ethyl-5-acetamido-4,7,8,9-tetra-0-acetyl-3,5-dideoxy-D-glycero-β-D-galacto-2-nonulopyranosid]onate (Compound 104)

To a mixture of 2-benzyloxycarbonyl-2-palmitoylamidoethanol (244 mg), the β-acetyl derivative (100 mg) and methylene chloride (10 ml) was added boron trifluoride ether complex salt (230 μl ), and the mixture was stirred at room temperature for 41 hours. After completion of the reaction, the mixture was neutralized with aqueous sodium hydrogencarbonate solution. After separating the aqueous layer, the organic layer was dried, and the solvent was removed by distillation under reduced pressure.

The residue was purified by silica-gel column chromatography (CHCl$_3$-EtOH 200:1), to produce 59 mg of the β isomer (Compound 104). The yield was 35%.

R$_F$=0.56 (CHCl$_3$-MeOH 25:1).

[α]$_D$ −17.8° (c 0.96, CHCl$_3$).

$^1$H-NMR(CDCl$_3$)δ(ppm) in 500 MHz:0.88(t, 3H), 1.2–1.4(m, 24H), 1.6–1.7(m, 2H), 1.84(dd, 1H), 1.84(s, 3H), 1.99(s, 6H), 2.04(s, 3H), 2.10(s, 3H), 2.12(s, 3H), 2.27(t, 2H), 2.36(dd, 1H), 3.56(dd, 1H), 3.65(dd, 1H), 3.79(s, 3H), 3.99(dd, 1H), 4.03(ddd, 1H), 4.03(dd, 1H), 4.72(dd, 1H), 4.77(d, 1H), 4.86(ddd, 1H), 4.87(ddd, 1H), 5.16(d, 1H), 5.18(ddd, 1H), 5.24(dd, 1H), 5.46(d, 1H), 6.57(d, 1H), 7.3–7.5(m, 5H).

IR(KBr)cm$^{-1}$:2932, 1748, 1650, 1538, 1374, 1228, 1122.

Example 112 Synthesis of methyl [2-(2-benzyloxycarbonylamino)ethyl-5-acetamido-4,7,8,9-tetra-0-acetyl-3,5-dideoxy-D-glycero-β-D-galacto 2-nonulopyranosid]onate (Compound 105)

To a mixture of 2-benzyloxycarbonylaminoethanol (110 mg), the β-acetyl derivative (100 mg) and methylene chloride (5 ml) was added boron trifluoride ether complex salt (115 μl ), and the mixture was stirred at room temperature for 20 hours. After completion of the reaction, the mixture was neutralized with aqueous sodium hydrogencarbonate solution. After separating the aqueous layer, the organic layer was dried, and the solvent was removed by distillation under reduced pressure.

The residue was purified by silica-gel column chromatography (CHCl$_3$-EtOH 150:1), produce 65 mg of the β isomer (Compound 105). The yield was 52%.

R$_F$=0.43 (CHCl$_3$-MeOH 25:1).

$^1$H-NMR(CDCl$_3$)δ(ppm) in 500 MHz:1.82(dd, 1H), 1.72(s, 3H), 2.00(s, 3H), 2.04(s, 3H), 2.06(s, 3H), 2.16(s, 3H), 2.42(dd, 1H), 3.3–3.5(m, 3H), 3.57–3.62(m, 1H), 3.77(s, 3H), 4.03(dd, 1H), 4.03(ddd, 1H), 4.07(dd, 1H), 4.73(dd, 1H), 5.13(br.s, 2H), 5.15–5.25(m, 3H), 5.35(dd, 1H), 5.46(ddd, 1H), 7.3–7.4(m, 5H).

EXAMPLE 201

(1) Synthesis of methyl (n-hexdecyl-5-acetamido-4,7,8,9-tetra-0-acetyl-3,5-dideoxy-2-thio-D-glycero-α-and-β-D-galacto-2-nonulopyranosid)onate (Compounds 203a and 203b)

A mixture of powdered Molecular sieves 4A (400 mg) and zinc bromide (290 mg, 1.29 mmol) was stirred in methylene chloride (4 ml) at room temperature for 2.5 hours. On the other hand, a mixture of methyl 5-acetamido-4,7,8,9-tetra-0-acetyl-2-chloro-2,3,5- trideoxy-D-glycero-β-D-galacto-2-nonulopyranosonate (Compound 201, 250 mg, 0.49 mmol), hexadecyl mercaptan (Compound 202, 380 mg, 1.08 mmol) and Molecular sieves 4A (150 mg) was stirred in methylene chloride (5 ml) at room temperature for 2.5 hours. The solution was poured dropwise to the first mentioned mixture solution, and the resultant mixture was stirred at room temperature for 3 days.

To the resultant reaction mixture was added aqueous solution of $NaHCO_3$ under ice cooling, and the insoluble matter was filtered out by celite filtration. The organic layer was separated, washed with water and dried (with $MgSO_4$), and the solvent was removed by distillation under reduced pressure. The residue was subjected to column-chromatography with silica-gel (50 g) where elution with $CHCl_3$ and then $CHCl_3$-EtOH (100:1) was carried out, to produce separately the β-glycoside (Compound 203b, 126 mg, 35%) and the α-glycoside (Compound 203a, 93 mg, 26%) in the descending order of $R_F$.

Compound 203a (α-isomer):
$^1$H-NMR($CDCl_3$)δ:0.88(3H, t, J=6.8 H), 1.2–1.4(26H, m), 1.4–1.6(2H, m), 1.88, 2.03, 2.04, 2.14, 2.16(15H, 5s), 2.50–2.56(1H, m), 2.72(1H, dd, J=4.6, 12.7 Hz), 2.70–2.77(1H, m), 3.80(3H, s), 3.82(1H, dd, J=2.0, 10.5 Hz), 4.05(1H, ddd, J=10.0, 10.5, 10.5 Hz), 4.12(1H, dd, J=4.9 Hz, 12.5 Hz), 4.31(1H, dd, J=2.4, 12.5 Hz), 4.86(1H, ddd, J=4.6, 10.5, 11.7 Hz), 5.10(1H, d, J=10.0 Hz), 5.33(1H, dd, J=2.2, 8.3 Hz), 5.35–5.38(1H, m).
$[α]_D$ +22.4° (c 0.82, $CHCl_3$).

Compound 203b (β-isomer):
$^1$H-NMR($CDCl_3$)δ:0.88(3H, t, J=6.8 H), 1.2–1.4(26H, m), 1.45–1.61(2H, m), 1.89, 2.02, 2.04, 2.08, 2.14(15H, 5s), 2.45–2.59(3H, m, $SCH_2$), 3.81(3H, s), 4.08(1H, ddd, J=10.3, 10.5 Hz), 4.81(1H, dd, J=8.1 Hz, 12.2 Hz), 4.33(1H, dd, J=2.2, 10.5 Hz), 4.81(1H, dd, J=2.2, 12.2 Hz), 5.11 (1H, ddd, J=2.2, 2.7, 8.1 Hz), 5.24–5.29(2H, m, H- 4), 5.43(1H, dd, J=2.2, 2.7 Hz).
$[α]_D$ −57.2° (c 0.99, $CHCl_3$).

(2) Synthesis of methyl (n-hexadecyl-5-acetamido-3,5-dideoxy-2-thio-D-glycero-α-galacto-2-nonulopyranosid)onate (Compound 204a)

The acetoxy derivative (Compound 203a, 79 mg, 0.11 mmol) was dissolved in MeOH (3 ml). To the solution was added 28% MeONa (15 μl) with stirring under ice cooling, and the mixture was stirred at the same temperature for 1 hour and then at room temperature for 2 hours.

To the resultant reaction solution was added acetic acid, and the mixture was concentrated under reduced pressure. The residue was subjected to column-chromatography with silica-gel (10 g). Eluting with $CHCl_3$-MeOH (25:1) gave the compound (Compound 204a, 53 mg, 87%).

$^1$H-NMR($CDCl_3$)δ:0.90(3H, t, J=6.8 H), 1.3–1.4(26H, m), 1.78(1H, dd, J=11.5, 12.9 Hz), 1.99(3H, s), 2.57–2.63(1H, m), 2.74(1H, dd, J=11.5, 12.9 Hz), 1.99(3H, s), 2.57–2.63(1H, m), 2.74(1H, dd, J=4.6, 12.9 Hz), 2.72–2.79(1H, m), 3.40 (1H, dd, J=1.7, 10.5 Hz), 3.50(1H, dd, J=1.7, 9.0 Hz), 3.60–3.65(2H, m).
$[α]_D$ +36.8° (c 0.87, MeOH).

(3) Synthesis of sodium (n-hexadecyl-5-acetamido-3,5-dideoxy-2-thio-D-glycero-α-galacto-2-nonulopyranosid)onate (Compound 205a)

The methyl ester derivative (Compound 204a, 43 mg, 0.076 mmol) was dissolved in MeOH (8 ml). To the solution was added 0.1N aqueous NaOH solution (2.3 ml), and the mixture was stirred at room temperature for 30 days.

The resultant solution was neutralized under ice cooling by addition of weakly acidic resin ("Amberlite IRC-50"), and after the insoluble matter had been removed by filtration, the residue was concentrated under reduced pressure. The crystals thus obtained were washed with $Et_2O$, to produce the compound (Compound 205a) as colorless powder (37 mg, 85%).

$^1$H-NMR($CD_3$ OD)δ:0.90(3H, t, J=6.8 H), 1.2–1.4(26H, m), 1.2–1.4(26H, m), 1.5–1.6(2H, m), 1.62(1H, dd, J=10.7, 12.5 Hz), 2.00(3H, s), 2.6–2.7(1H, m), 2 80–2.84(1H, m), 2.86 (1H, dd, J=4.2, 12.5 Hz).
$[α]_D$ +19.6° (c 0.89, MeOH).

EXAMPLE 202

(1) Methyl (n-hexadecyl-5-acetamido-3,5-dideoxy-2-thio-D-glycero-β-D-galacto-2-nonulopyranosid)onate (Compound 204b)

The acetoxy derivative obtained in Example 201(1) (Compound 203b, 109 mg, 0.15 mmol) was dissolved in MeOH (2 ml). To the solution was added 28% MeONa (10 μl) with stirring under ice cooling, and the mixture was stirred at the same temperature for 5 hours, followed by stirring at room temperature for 1 hour.

To the resulting reaction solution was added acetic acid, and the mixture was concentrated under reduced pressure. The residue was subjected to column-chromatography with silica-gel (10 g). Eluting with $CHCl_3$-MeOH (15:1) gave the above compound (Compound 204b, 54 mg, 64%).

$^1$H-NMR($CD_3$ OD)δ:0.90(3H, t, J=6.8 Hz), 1.2–1.4(26H, m), 1.45–1.55(2H, m), 1.91(1H, dd, J=11.5, 13.9 Hz), 2.00(3H, s), 2.44(1H, dd, J=4.9, 13.9 Hz), 2.5–2.6(1H, m), 2.6–2.8(1H, m), 3.52 (1H, dd, J=1.2, 9.0 Hz), 3.66(1H, dd, J=5.6, 11.7 Hz), 3.77(3H, s), 3.77–3.83(3H, m), 4.08(1H, ddd, 4.9, 11.5, 13.9), 4.14(1H, dd, J=1.2, 10.8 Hz).
$[α]_D$ −91.3° (c 0.84, MeOH).

(2) Sodium(n-hexadecyl-5-acetamido-3,5-dideoxy-2-thio-D-glycero-β-D-galacto-2-nonulopyranosid)onate (Compound 205b)

The methyl ester derivative (Compound 204b, 45 mg, 0.080 mmol) was dissolved in MeOH (5 ml). To the solution was added 0.1N aqueous NaOH solution (2.0 ml), and the mixture was stirred at room temperature for 30 days, followed by stirring at 65° C. for 10 days.

The resultant reaction solution was neutralized by addition of weakly acidic resin Amberlite IRC-50 under ice cooling, and, after the insoluble matter had been filtered out, the filtrate was concentrated under reduced pressure. The crystals thus obtained were washed with $Et_2O$, to produce the compound (Compound 205b) as colorless powder (41 mg, 89%).

$^1$H-NMR($CD_3$ OD)δ:0.90(3H, t, J=6.8 Hz), 1.2–1.4(26H, m), 1.5–1.6(2H, m), 1.98(3H, s), 2.53(1H, dd, J=4.6, 13.7 Hz), 2.58(2H, m), 3.66(1H, dd, J=5.4, 11.5 Hz), 3.74–3.80(2H, m), 3.88–3.96(2H, m), 4.20(1H, d, J=10.3 Hz).

$[\alpha]_D$ −74.3° (c 0.98, MeOH).

EXAMPLE 203

70 μmol of L-α-dipalmitoylphosphatidyl choline, 70 μmol of cholesterol and 7 μmol of Compound 205a obtained in Example 201(3) were dissolved in a mixture of chloroform and methanol (2:1 volume ratio). Then, the organic solvent was removed in nitrogen flow to generate lipid film on the glass wall of a centrifuge tube.

To the tube was added 7 ml of 1 mM inulin solution dissolved in phosphate buffer saline (hereinafter referred to as PBS, pH 7.4) and previously warmed to about 45° C., and the tube was shaken. The mass was subjected lightly to ultrasonic treatment to produce a liposome suspension. The suspension was heated to 45°–60° C. and passed through a membrane filter of 0.08 μm in pore size and made of polycarbonate, to produce a liposome suspension having a particle size of about 0.08 μm. Then, the suspension was subjected to ultracentrifugation ($10^5 \times$ g, 1 hour, three times), and the supernatant was discarded, whereby the inulin not bound to the liposomes was removed. To the residue was added PBS to produce 5 ml in total of liposome suspension (object suspension).

EXAMPLE 204

Repetition of the same procedure as in Example 203 except the use of Compound 205b obtained in Example 202(2) instead of Compound 205a obtained in Example 201(3) produced 5 ml in total of liposome suspension (object suspension).

EXAMPLE 205

500 mg of soybean oil, 60 mg of yolk lecithin and 125 mg of glycerin were weighed out, added together to 5 ml of distilled water for injection and coarsely emulsified with a homogenizer. To this mixture was added 2.9 mg of Compound 205a obtained in Example 201(3), and the mass was further emulsified by ultrasonic treatment, to produce 5 ml of the object lipid microsphere.

Test Example 201

(a) Sample

Repetition of the same procedure as in Examples 203 and 204 except the use of 1 mM inulin containing 140 μCi of $^3$H-inulin instead of 1 mM inulin in Examples 203 and 204 produced two kinds of liposome suspensions (object suspensions) each totalling 5 ml, which are referred to as Test Samples 201 and 202, respectively. When assayed by an enzymatic method where the choline group of L-α-dipalmitoylphosphatidyl choline is used as the marker, the test samples 201 and 202 each contained 10.1 μmol of the phospholipid per 1 ml.

And, repetition of the same procedure as in Example 203 except the use of 3.5 μmol of dicetyl phosphate instead of 7 μmol of Compound 205a obtained in Example 201(3), and 1 mM inulin containing 140 μCi of $^3$H-inulin instead of 1 mM inulin in Example 203 produced 5 ml in total of liposome suspension, which is referred to as Control Sample 201 (control liposome). Likewise, repetition of the same procedure as in Example 203 except the use of 7 μmol of ganglioside GM$_1$ instead of 7 μmol of Compound 205a obtained in Example 201(3), and 1 mM inulin containing 140 μCi of $^3$H-inulin instead of 1 mM inulin in Example 203 produced 5 ml in total of liposome suspension, which is referred to as Control Sample 202 (GM$_1$-containing liposome). When assayed by an enzymatic method where the choline group of L-α-dipalmitoylphosphatidyl choline is utilized as the marker, Control Samples 201 and 202 had 11.9 μmol and 10.0 μmol of the phospholipid per 1 ml, respectively.

(b) Assay method

Applying the same method as in Test Example 1 to the four samples, the concentration in blood (%) and the tissue/plasma partition coefficient (Kp values) were calculated.

(c) Results

Figure 2:
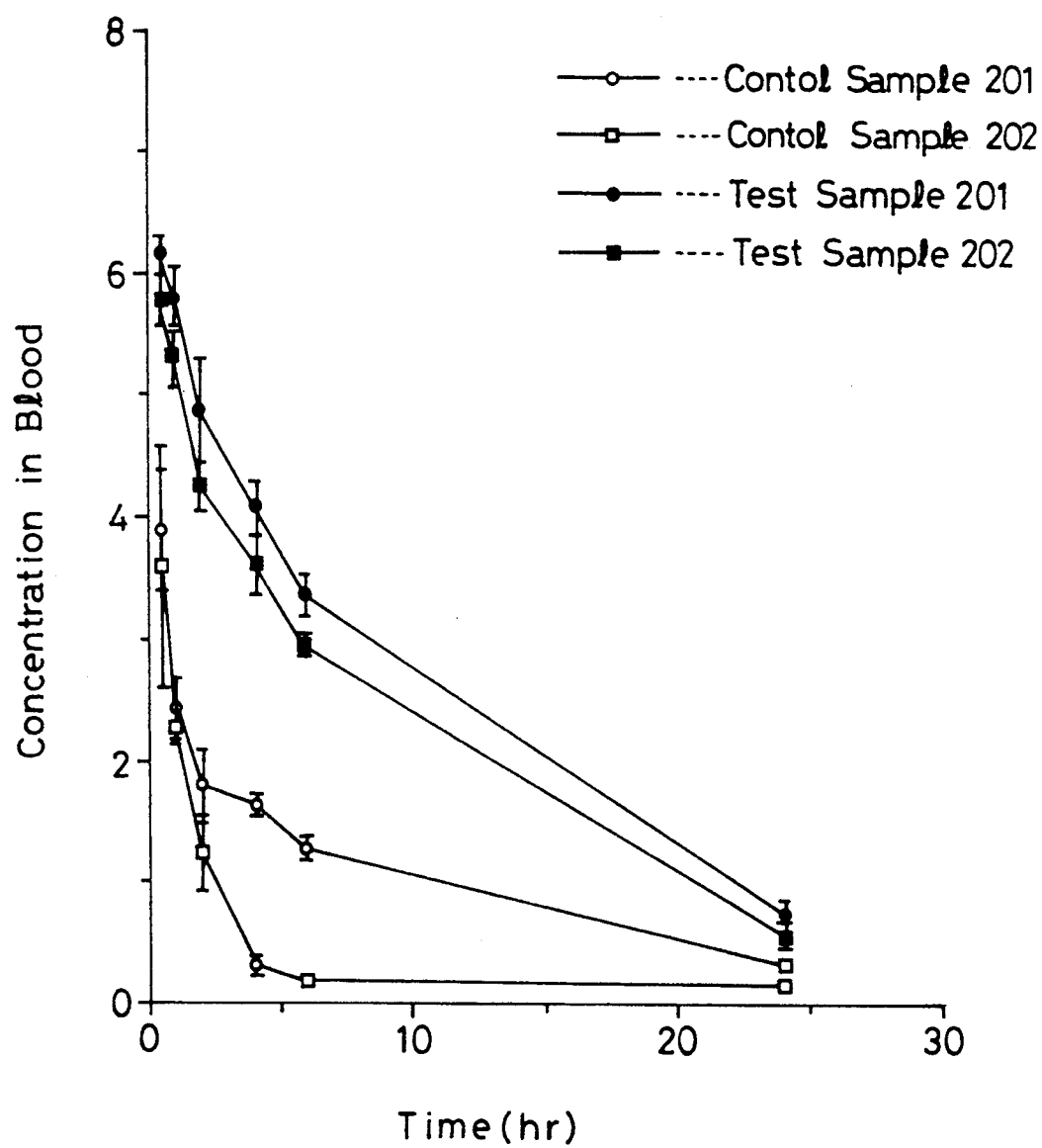
FIG. 2 illustrates the hourly change in blood concentration of inulin in Test example 201, and FIG. 3 plots Kp values for individual organs in the same test.

The results are illustrated in FIGS. 2 and 3.

FIG. 2 plots the hourly change of the inulin concentration in blood. The lines through ○ (open circles), □ (open squares), ● (closed circles) and ■ (closed squares) represent the results concerning Control Samples 201 and 202, and Test Samples 201 and 202, respectively.

FIG. 3 plots $K_p$'s for individual organs. The columns filled with vertical and slant lines (▦ and ▨) represent the results concerning Control Samples 201 and 202, respectively. The shaded and solid columns and represent the results concerning Test Samples 201 and 202.

It is obvious from both figures that the liposomes of this invention can maintain a higher concentration in blood than the control liposomes and GM$_1$-containing liposomes. Further, from the $K_p$'s for the liver, spleen and bone marrow being significantly lower it is obvious that the liposomes of this invention are resistant to capture by the reticuloendothelial system.

Reference Example 301
2-Benzyloxycarbonyl-2-palmitoylaminoethanol
(Compound 301)

L-Serine benzyl ester tosylate (15.69 g, 42.6 mmol) was dissolved in CH$_2$Cl$_2$(250 ml). To the solution were added dropwise triethylamine (8.64 g, 85.4 mmol) and palmitoyl chloride (10.56 g, 38.4 mmol) with stirring under ice cooling. Thereafter, the mixture was stirred at room temperature for 5 hours.

The reaction solution was washed with water, dried with MgSO$_4$, and concentrated under reduced pressure. The crystals thus obtained were washed with IPE (isopropyl ether), to produce the compound (Compound 301) as colorless crystals (8.76 g, 53%).

mp 84°–85° C.

IR(KBr)cm$^{-1}$:3302, 1742, 1634, 1551, 1472.

$^1$H-NMR(CDCl$_3$)δ:0.88(t, 3H), 1.2–1.4(m, 24H), 1.64(quintet, 2H), 2.26(t, 2H), 3.94(dd, 1H), 4.00(dd, 1H), 4.73(ddd, 1H), 5.22 and 5.23(ABq, 2H), 6.38(d, 1H), 7.3–7.4(m, 5H).

$[\alpha]_D$ +7.9° (c 1.07, CHCl$_3$).

Elemental analysis:

Calcd. for C$_{26}$H$_{43}$NO$_4$: C, 72.01; H, 10.00; N, 3.23,

Found: C, 72.20; H, 10.32; N, 3.45.

Reference Example 302 2-Palmitoylaminoethanol
(Compound 302)

2-Aminoethanol (13.76 g, 225.3 mmol) was dissolved in CHCl$_3$ (750 ml). To the solution was added dropwise palmitoyl chloride (15.48 g, 56.3 mmol) with stirring under ice cooling. Thereafter, the mixture was stirred at room temperature for 19 hours.

The resultant reaction solution was washed with 10% aqueous citric acid solution, and the insoluble matter was filtered out. The organic layer was, after separated, washed with water, dried with MgSO$_4$, and concentrated under reduced pressure. The crystals thus obtained were washed with IPE, to produce the compound (Compound 302) as colorless crystals (13.50 g, 80%).

mp 98°–99° C.

IR(KBr)cm$^{-1}$:3362, 1641, 1555, 1474, 1462, 1441, 1059.

$^1$H-NMR(CDCl$_3$)δ:0.88(t, 3H), 1.2–1.4(m, 24H), 1.64(quintet, 2H), 2.21(t, 2H), 3.43(q, 2H), 3.74(t, 2H), 5.96(br s, 1H).

Reference Example 303
2-Benzyloxycarbonylaminoethanol (Compound 303)

2-Aminoethanol (6.74 g, 110.3 mmol) and triethylamine (11.17 g, 110.3 mmol) were dissolved in CHCl$_3$ (400 ml). To the solution was added dropwise N-carbobenzoxyoxysuccinimide (25.00 g, 100.3 mmol) with stirring under ice cooling. Thereafter, the mixture was stirred at room temperature for 3 hours.

The resultant reaction solution was washed with water, 5% aqueous NaHCO$_3$ solution, water, 10% aqueous citric acid solution, and water in that order, and dried with MgSO$_4$. The solvent was removed by distillation under reduced pressure. The crystals thus formed were washed with n-hexane to produce the compound (Compound 303) as colorless crystals (17.40 g, 89%).

mp 56°–59° C.

IR(KBr)cm$^{-1}$:1639, 1547, 1277, 1213, 1151, 1036.

1H-NMR(CDCl$_3$)δ:3.36(m, 2H), 3.72(t, 2H), 5.11(s, 2H), 7.2–7.4(m, 5H).

Example 301 Methyl
[2-(2-benzyloxycarbonyl-2-palmitoylamino)ethyl-5 acetamido-4,7,8,9-tetra-0-acetyl-
3,5-dideoxy-D-glycero-α-and-β-D-galacto-2-nonulopyranosid]onate (Compounds 305A and 305B)

A mixture of powdered Molecular sieves 4A (400 mg, made by Nacalai Tesque Co.) and zinc bromide (110 mg, 0.49 mmol) was stirred in CH$_3$Cl$_2$ (5 ml) at room temperature for 3,5 hours. Concurrently, a mixture of methyl 5-acetamido-4,7,8,9-tetra-0-acetyl-2-chloro-2,3,5-trideoxy-D-glycero-β-D-galacto-2-nonulopyranosonate (Compound 304) (250 mg, 0.49 mmol), Compound 301 (425 mg, 0.98 mmol) and Molecular sieves 4A (150 mg, made by Nacalai Tesque Co.) was stirred in CH$_2$Cl$_2$ (5 ml) at room temperature for 3.5 hours. The last-mentioned mixture was poured dropwise to the first-mentioned mixture, and the resultant mixture was stirred at room temperature for 20 hours.

Aqueous NaHCO$_3$ solution was added to the reaction mixture under ice cooling, and the insoluble matter was filtered out by celite filtration. The organic layer was, after separated, washed with water, dried (MgSO$_4$) and the solvent was removed by distillation under reduced pressure.

The residue was subjected to column-chromatography with silica gel (50 g) where elution with CHCl$_3$ and then CHCl$_3$-EtOH (100:1) was carried out. Repeating this procedure several times produced the β-isomer (Compound 305B) and the α-isomer (Compound 305A) separately in the descending order of R$_F$. Their yields and percent yields of the two compounds were 51 mg and 12%, and 192 mg and 43%, respectively.

Compound 305A (α-isomer):
Colorless foamy substance.

$^1$H-NMR(CDCl$_3$)δ:0.88(t, 3H), 1.2–1.4(m, 24H), 1.6–1.7(m, 2H), 1.89(dd, 1H), 1.89, 2.03, 2.04, 2.13, 2.14(5s, 15H), 2.27(m, 2H), 2.52(dd, 1H), 3.71(s, 3H), 3.84(dd, 1H), 4.01(dd, 1H), 4.08(dd, 1H), 4.09(ddd, 1H), 4.11(dd, 1H), 4.25(dd, 1H), 4.79(ddd, 1H), 4.86(ddd, 1H), 5.12(d, 1H), 5.18 and 5.19(ABq, 2H), 5.33(dd, 1H), 5.36(ddd, 1H), 6.26(d, 1H), 7.3–7.4(m, 5H).

[α]$_D$ −14.1° (c 0.78, CHCl$_3$).

Elemental analysis:
Calcd. for C$_{46}$H$_{70}$N$_2$O$_{16}$: C, 60.91; H, 7.78; N, 3.09, Found: C, 61.03; H, 7.94; N, 2.84.

Compound 305B (β-isomer):
mp 85°–87° C.

IR(KBr)cm$^{-1}$:2932, 2860, 1748, 1650, 1538, 1464, 1374, 1228, 1122.

1H-NMR(CDCl$_3$)δ:0.88(t, 3H), 1.2–1.4(m, 24H), 1.64(m, 2H), 1.84(dd, 1H), 1.84, 1.99, 2.04, 2.10, 2.12(5s, 15H0, 2.27(t, 2H), 2.36(dd, 1H), 3.56(dd, 1H), 3.65(dd, 1H), 3.79(s, 3H), 3.99(dd, 1H), 4.03(ddd, 1H), 4.03(dd, 1H), 4.72(dd, 1H), 4.77(d, 1H), 4.86(ddd, 1H), 4.87(ddd, 1H), 5.16(d, 1H), 5.18(ddd, 1H), 5.24(dd, 1H), 5.46(d, 1H), 6.57(d, 1H), 7.3–7.5(m, 5H).

[α]$_D$ −17.8° (c 0.96, CHCl$_3$).

Elemental analysis:
Calcd. for C$_{46}$H$_{70}$N$_2$O$_{16}$: C, 60.91; H, 7.78; N, 3.09,
Found: C, 61.05; H, 7.90; N, 3.22.

Example 302 Methyl
[2-(2-benzyloxycarbonyl-2-palmitoylamino)ethyl-5-acetamido-4,7,8,9-tetra-0-acetyl-3,5-dideoxy-D-glycero-α-and-β-galacto-2-nonulopyranosid]onate
(Compounds 305A and 305B)

A mixture of powdered Molecular sieves 4A (315 mg), zinc bromide (221 mg, 0.98 mmol) and trityl bromide (634 mg, 1.96 mmol) was stirred in CH$_2$Cl$_2$ (10 ml) at room temperature for 4 hours. On the other hand, a mixture of Compound 304 (500 mg, 0.98 mmol), Compound 301 (850 mg, 1.96 mmol) and Molecular sieves 4A (260 mg) was stirred in CH$_2$Cl$_2$ (6 ml) at room temperature for 5.5 hours. The resultant solution was poured dropwise to the first-mentioned mixture, and the resultant mixture was stirred at room temperature for 20 hours.

Aqueous NaHCO$_3$ solution was added to the reaction mixture under ice cooling, and the insoluble matter was filtered out by celite filtration. The organic layer was, after separated, washed with water and dried (MgSO$_4$) and the solvent was removed by distillation under reduced pressure.

The residue was subjected to column-chromatography with silica gel (50 g) where elution with CHCl$_3$ and then CHCl$_3$-EtOH (200:1). Repeating this chromatography several times produced the β-isomer (Compound 305B) and the α-isomer (Compound 305B) separately in the descending order of R$_F$. Their yields and percent yields of the two compounds were 67 mg and 8%, and 369 mg and 42%, respectively.

EXAMPLE 303

Subjecting Compound 304 (250 mg, 0.49 mmol), Compound 301 (425 mg, 0.98 mmol) and zinc chloride (70 mg, 0.51 mmol) to the same treatment as in Example 301 produced Compounds 305A and 305B. Their yields and percent yields were 195 mg and 44%, and 58 mg and 13%, respectively.

EXAMPLE 304

Subjecting Compound 304 (250 mg, 0.49 mmol), Compound 301 (425 mg, 0.98 mmol) and tin dichloride (102 mg, 0.54 mmol) to the same treatment as in Example 301 produced Compounds 305A and 305B. Their yields and percent yields were 125 mg and 28%, and 130 mg and 29%, respectively.

EXAMPLE 305

Subjecting Compound 304 (250 mg, 0.49 mmol), Compound 301 (425 mg, 0.98 mmol) and copper (II) chloride (70 mg, 0.52 mmol) to the same treatment as in Example 301 produced Compounds 305A and 305B. Their yields and percent yields were 114 mg and 25%, and 79 mg and 18%, respectively.

EXAMPLE 306

Subjecting Compound 304 (250 mg, 0.49 mmol), Compound 301 (425 mg, 0.98 mmol) and tin trifluoromethanesulfonate (208 mg, 0.50 mmol) to the same treatment as in Example 301 produced Compounds 305A and 305B. Their yields and percent yields were 53 mg and 12%, and 145 mg and 32%, respectively.

EXAMPLE 307

Subjecting Compound 304 (250 mg, 0.49 mmol), Compound 301 (425 mg, 0.98 mmol) and zinc iodide (160 mg, 0.50 mmol) to the same treatment as in Example 301 produced Compounds 305A and 305B. Their yields and percent yields were 175 mg and 40%, and 46 mg and 10%, respectively.

EXAMPLE 308

Subjecting Compound 304 (250 mg, 0.49 mmol), Compound 301 (425 mg, 0.98 mmol) and zinc trifluoromethanesulfonate (182 mg, 0.50 mmol) to the same treatment as in Example 301 produced Compounds 305A and 305B. Their yields and percent yields were 150 mg and 34%, and 105 mg and 23%, respectively.

EXAMPLE 309

Subjecting Compound 304 (500 mg, 0.98 mmol), Compound 301 (850 mg, 1.96 mmol), zinc chloride (140 mg, 1.03 mmol) and trityl chloride (547 mg, 1.96 mmol) to the same treatment as in Example 302 produced Compounds 305A and 305B. Their yields and percent yields were 328 mg and 37%, and 116 mg and 13%, respectively.

EXAMPLE 310

Subjecting Compound 304 (500 mg, 0.98 mmol), Compound 301 (850 mg, 1.96 mmol), tin dichloride (204 mg, 1.08 mmol) and trityl chloride (547 mg, 1.96 mmol) to the same treatment as in Example 302 produced Compounds 305A and 305B. Their yields and percent yields were 173 mg and 20%, and 208 mg and 23%, respectively.

EXAMPLE 311

Subjecting Compound 304 (500 mg, 0.98 mmol), Compound 301 (850 mg, 1.96 mmol), tin dibromide (273 mg, 0.98 mmol) and trityl bromide (634 mg, 1.96 mmol) to the same treatment as in Example 302 produced Compounds 305A and 305B. Their yields and percent yields were 154 mg and 17%, and 128 mg and 14%, respectively.

Example 312 Methyl [2-(8-azidooctyl)-5-acetamido-4,7,8,9-tetra 0-acetyl-3,5-dideoxy-D-glycero-α-and-β-D-galacto-2-nonulopyranosid]onate (Compounds 306A, and 306B)

Subjecting Compound 304 (250 mg, 0.49 mmol), 8-azidooctanol (170 mg, 0.99 mmol) and zinc bromide (123 mg, 0.55 mmol) to the same treatment as in Example 301 produced the α- and the β-glycoside derivatives (Compounds 306A and 306B). Their yields and percent yields were 121 mg and 38%, and 95 mg and 29%, respectively.

Compound 306A (α-isomer):
$^1$H-NMR(CDCl$_3$)δ:1.27–1.40(m, 8H), 1.50–1.64(m, 4H), 1.88(s, 3H), 1.95(dd, 1H), 2.03, 2.05, 2.14, 2.15(4s, 12H), 2.58(dd, 1H), 3.21(dt, 1H), 3.36(t, 2H), 3.75(dt, 1H), 3.80(s, 3H), 4.06(ddd, 1H), 4.08(dd, 1H), 4.10(dd, 1H), 4.31(dd, 1H), 4.84(ddd, 1H), 5.11(d, 1H), 5.33(dd, 1H), 5.40(ddd, 1H).
$[α]_D$ −16.2° (c 1.00, CHCl$_3$).

Compound 306B (β-isomer):
$^1$H-NMR(CDCl$_3$)δ:1.26–1.42(m, 8H), 1.51–1.65(m, 4H), 1.86(dd, 1H), 1.88(s, 3H), 2.02, 2.03, 2.07, 2.14(4s, 12H), 2.46(dd, 1H), 3.27(t, 2H), 3.31(dt, 1H), 3.47(dt, 1H), 3.80(s, 3H), 3.92(dd, 1H), 4.11(ddd, 1H), 4.12(dd, 1H), 4.80(dd, 1H), 5.19(ddd, 1H), 5.23(d, 1H), 5.25(ddd, 1H), 5.39(dd, 1H).
$[α]_D$ −11.5° (c 1.01, CHCl$_3$).

EXAMPLE 313

Subjecting Compound 304 (250 mg, 0.49 mmol), 8-azidooctanol (170 mg, 0.99 mmol) and zinc bromide (123 mg, 0.55 mmol) in acetonitrile to the same treatment as in Example 301 produced Compounds 306A and 306B. Their yields and percent yields were 141 mg and 43%, and 61 mg and 19%, respectively.

EXAMPLE 314

Subjecting Compound 304 (250 mg, 0.49 mmol), 8-azidooctanol (170 mg, 0.99 mmol) and zinc bromide (123 mg, 0.55 mmol) and trityl bromide (353 mg, 1.09 mmol) to the same treatment as in Example 302 produced Compounds 306A and 306B. Their yields and percent yields were 83 mg and 25%, and 86 mg and 27%, respectively.

Example 315 Methyl [2-(2-benzyloxycarbonylamino)ethyl-5-acetamido-4,7,8,9-tetra-0-acetyl-3,5-dideoxy-D-glycero-α-and-β-D-galacto-2-nonulopyranosid]onate (Compounds 307A an 307B)

Subjecting Compound 304 (500 mg, 0.98 mmol), Compound 303 (383 mg, 1.96 mmol), zinc bromide (221 mg, 0.98 mmol) and trityl bromide (634 mg, 1.96 mmol) to the same treatment as in Example 302 produced the α- and the β-glycoside derivatives (Compounds 307A and 307B). Their yields and percent yields were 255 mg and 39%, and 26 mg and 4%, respectively.

Compound 307A (α-isomer):
$^1$H-NMR(CDCl$_3$)δ:1.87, 2.01, 2.02, 2.05, 2.12(5s, 15H), 1.92(dd, 1H), 2.54(dd, 1H), 3.4–3.5(m, 3H), 3.75(s, 3H), 3.78(m, 1H), 4.02(ddd, 1H), 4.04(dd, 1H), 4.14(dd, 1H), 4.26(dd, 1H), 4.84(ddd, 1H), 5.09(br s, 2H), 5.14(d, 1H), 5.9(br s, 1H), 5.28(dd, 1H), 5.38(ddd, 1H), 7.3–7.4(m, 5H).

Compound 307B (β-isomer):
$^1$H-NMR(CDCl$_3$)δ:2.42(dd, 1H).

Example 316 Methyl 5-acetamido-4,7,8,9-tetra-0-acetyl-2-(5-cholesten-3β-yl)-3,5-dideoxy-D-glycero-α-and-β-D-galactononulopyranosonate (Compounds 308A and 308B)

Subjecting Compound 304 (250 mg, 0.49 mmol), cholesterol (387 mg, 1.0 mmol) and zinc bromide (169 mg, 0.75 mmol) to the same treatment as in Example 301 produced the α- and the β-glycoside derivatives (Compounds 308A and 308B). Their yields and percent yields were 84 mg and 20%, and 63 mg and 15%, respectively.

Compound 308A (α-isomer)

$^1$H-NMR(CDCl$_3$)δ:1.88, 2.02, 2.03, 2.13, 2.15(5s, 15H), 2.60(dd, 1H), 3.79(s, 3H), 4.85(ddd, 1H).

Compound 308B (β-isomer):

$^1$H-NMR(CDCl$_3$)δ:1.87, 2.08, 2.13(3s, 9H), 2.02(s, 6H), 2.53(dd, 1H), 3.80(s, 3H), 5.24(m, 1H).

Example 317 3-0-(Methyl 5-acetamido-4,7,8,9-tetra-0-acetyl-3,5-dideoxy-D-glycero-α-and-β-D-galacto-2-nonulopyranosylonate)-1,2-di-0-tetradecyl-sn-glycerol (Compounds 309A and 309B)

Subjecting Compound 304 (250 mg, 0.49 mmol), 1,2-di-0-tetradecyl-sn-glycerol (485 mg, 1.0 mmol) and zinc bromide (169 mg, 0.75 mmol) to the same treatment as in Example 301 produced the α- and the β-glycoside derivatives (Compounds 309A and 309B). Their yields and percent yields were 155 mg and 33%, and 99 mg and 21%, respectively.

Compound 309A (α-isomer):

$^1$H-NMR(CDCl$_3$)δ:1.97(t, 1H), 2.60(dd, 1H), 4.85(m, 1H).

Compound 309B (β-isomer):

$^1$H-NMR(CDCl$_3$)δ:1.90(t, 1H), 2.45(dd, 1H), 5.23(m, 1H).

Example 318 2',3'-Di-0-acetyl-5'-0-(4-N-acetamido-2,4-dideoxy-3,6,7,8-tetra-0-acetyl-1-methoxycarbonyl-D-glycero-α-and-β-D-galactooctapyranosyl)inosine (Compounds 310A and 310B)

Subjecting Compound 304 (250 mg, 0.49 mmol), 2',3'-di-0-acetylinosine (352 mg, 1.0 mmol) and zinc bromide (169 mg, 0.75 mmol) to the same treatment as in Example 301 produced the α- and the β-glycoside derivatives (Compounds 310A and 310B). Their yields and percent yields were 46 mg and 11%, and 53 mg and 13%, respectively.

Compound 310A (α-isomer):

$^1$H-NMR(CDCl$_3$)δ:2.00(dd, 1H), 2.71(dd, 1H), 3.77(s, 3H), 4.97(ddd, 1H), 6.26(d, 1H).

Compound 310B (β-isomer):

$^1$H-NMR(CDCl$_3$)δ:1.85(dd, 1H), 2.54(dd, 1H), 3.80(s, 3H), 4.86(ddd, 1H), 6.24(d, 1H).

Example 319 [2(S),3(R),4E]-3-0-Benzoyl-1-0-(methyl 5-acetamido-4,7,8,9-tetra-0-acetyl-3,5-dideoxy-D-glycero-α-and-β-D-galacto-2-nonulopyranosylonate)-2-octadecanamido-4-octadecene-1,3-diol (Compounds 311A and 311B)

Subjecting Compound 304 (250 mg, 0.49 mmol), [2(S),3(R),4E]-3-0-benzoyl-2-octadecanamido-4-octadecene-1,3-diol (670 mg, 1.0 mmol) and zinc bromide (169 mg, 0.75 mmol) to the same treatment as in Example 301 produced the α- and the β-glycoside derivatives (Compounds 311A and 311B). Their yields and percent yields were 128 mg and 23%, and 157 mg and 28%, respectively.

Compound 311A (α-isomer):

$^1$H-NMR(CDCl$_3$)δ:1.87, 2.07, 2.12(3s, 9H), 2.03(s, 6H), 2.59(dd, 1H), 3.57(s, 3H), 4.86(m, 1H).

Compound 311B (β-isomer):

$^1$H-NMR(CDCl$_3$)δ:1.85, 1.88, 1.96, 2.02, 2.11(5s, 15H), 2.46(dd, 1H), 3.77(s, 3H), 5.22(m, 1H).

Example 320 Methyl 3-0-benzoyl-6-0-(methyl 5-acetamido-4,7,8,9-tetra-0-acetyl-3,5-dideoxy-α-and-β-D-glycero-D-galacto-2-nonulopyranosylonate)-β-D-galactopyranoside (Compounds 312A and 312B)

Subjecting Compound 304 (250 mg, 0.49 mmol), methyl 3-0-benzoyl-β-D-galactopyranoside (298 mg, 1.0 mmol) and zinc bromide (225 mg, 1.0 mmol) to the same treatment as in Example 301 produced the α- and the β-glycoside derivatives (Compounds 312A and 312B). Their yields and percent yields were 169 mg and 45%, and 80 mg and 21%, respectively.

Compound 312A (α-isomer):

[α]$_D$ −7.6° (c 0.75, MeOH).

$^1$H-NMR(CD3OD)δ:2.64(dd, 1H), 3.57(s, 3H), 3.70(dd, 1H), 3.78(dd, 1H), 3.83(s, 3H), 3.86(ddd, 1H), 3.88(dd, 1H), 3.96(t, 1H), 4.12(dd, 1H), 4.18(dd, 1H), 4.21(dd, 1H), 4.35(dd, 1H), 4.38(d, 1H), 5.00(dd, 1H), 5.33(dd, 1H), 5.34(ddd, 1H).

Compound 312B (β-isomer):

[α]$_D$ −2.4° (c 0.70, MeOH).

$^1$H-NMR(CD3OD)δ:2.47(dd, 1H), 3.56(s, 3H), 3.59(dd, 1H), 3.72(dd, 1H), 3.83(s, 3H), 3.85(ddd, 1H), 3.89(dd, 1H), 3.96(t, 1H), 4.11(dd, 1H), 4.16(dd, 1H), 4.20(dd, 1H), 4.32(dd, 1H), 4.70(dd, 1H), 5.04(dd, 1H), 5.17(ddd, 1H), 5.29(ddd, 1H), 5.40(dd, 1H).

Example 321 Benzyl 2,6-di-0-benzyl-3-0-(methyl 5-acetamido-4,7,8,9-tetra-0-acetyl-3,5-dideoxy-α-and-β-D-glycero-D-galacto-2-nonulopyranosylonate)-β-D-galactopyranoside (Compounds 313A and 313B)

Subjecting Compound 304 (250 mg, 0.49 mmol), benzyl 2,6-di-0-benzyl-β-D-galactopyranoside (450 mg, 1.0 mmol) and zinc bromide (225 mg, 1.0 mmol) to the same treatment as in Example 301 produced the α- and the β-glycoside derivatives (Compounds 313A and 313B). Their yields and percent yields were 32 mg and 6%, and 36 mg and 8%, respectively.

Compound 313A (α-isomer):

$^1$H-NMR(CDCl$_3$)δ:1.86, 1.95, 1.98, 2.00, 2.09(5s, 15H), 2.53(dd, 1H), 3.77(s, 3H), 4.55(d, 1H), 4.60(s, 2H), 4.72(d, 1H), 4.84(d, 1H), 4.86(m, 1H), 4.96(d, 1H), 5.31(dd, 1H), 5.38(d, 1H), 5.38(dt, 1H), 7.20–7.40(m, 15H).

Compound 313B (β-isomer), $^1$H-NMR(CDCl$_3$)δ:1.71, 1.99, 2.04, 2.09, 2.13(5s, 15H), 2.55(dd, 1H), 3.59(s, 3H), 4.58(d, 1H), 4.60(d, 1H), 4.61(s, 2H), 4.66(d, 1H), 4.67(d, 1H), 4.74(dd, 1H), 4.98(d, 1H), 5.02(d, 1H), 5.11(dt, 1H), 5.21(ddd, 1H), 5.28(dd, 1H), 7.20–7.40(m, 15H).

Example 322 Methyl [2(2-palmitoylamido)ethyl-5-acetamido-4,7,8,9-tetra-0-acetyl-3,5-dideoxy-D-glycero-α-and-β-D-galacto-2-nonulopyranosid]onate) (Compounds 314A nd 314B)

Subjecting Compound 304 (500 mg, 0.98 mmol), Compound 302 (632 mg, 2.11 mmol) and zinc bromide (331 mg, 1.47 mmol) to the same treatment as in Example 301 produced the α- and the β-glycoside derivatives (Compounds 314A and 314B). Their yields and percent yields were 238 mg and 31%, and 115 mg and 15%, respectively.

Compound 314A (α-isomer):
Colorless oily substance.
$^1$H-NMR(CDCl$_3$)δ:0.88(t, 3H), 1.2–1.4(m, 24H), 1.6(m, 2H), 1.89, 2.04, 2.05, 2.14, 2.15(5s, 15H), 1.97(dd, 1H), 2.18(t, 2H), 2.58(dd, 1H), 3.4–3.5(m, 3H), 3.78(m, 1H), 3.81(s, 3H), 4.06(dd, 1H), 4.08(ddd, 1H), 4.15(dd, 1H), 4.31(dd, 1H), 4.86(ddd, 1H), 5.14(d, 1H), 5.33(dd, 1H), 5.38(ddd, 1H), 5.93(m, 1H).

Compound 314B (β-isomer):
Colorless oily substance.
$^1$H-NMR(CDCl$_3$)δ:0.88(t, 3H), 1.2–1.4(m, 24H), 1.6–1.7(m, 2H), 1.85(dd, 1H), 1.91, 2.02, 2.04, 2.07, 2.16(5s, 15H), 2.24(t, 2H), 2.45(dd, 1H), 3.4–3.5(m, 3H), 3.55–3.60(m, 1H), 3.81(s, 3H), 3.90(ddd, 1H), 4.08(dd, 1H), 4.13(dd, 1H), 4.73(dd, 1H), 5.19(ddd, 1H), 5.39(ddd, 1H), 5.39(dd, 1H), 5.61(d, 1H), 6.34(br s, 1H).

Example 323 Methyl [2-(trimethylsilyl)ethyl-5-acetamido-4,7,8,9-tetra-0-acetyl-3,5-dideoxy-D-glycero-α-and-β-D-galacto-2-nonulopyranosid]onate (Compounds 315A and 315B)

Subjecting Compound 304 (250 mg, 0.49 mmol), 2-(trimethylsilyl) ethanol (118 mg, 1.0 mmol) and zinc bromide (225 mg, 1.0 mmol) to the same treatment as in Example 301 produced the α- and the β-glycoside derivatives (Compounds 315A and 315B). Their yields and percent yields were 62 mg and 21%, and 49 mg and 17%, respectively.

Compound 315A (α-isomer):
$^1$H-NMR(CDCl$_3$)δ:0.88(m, 2H), 2.57(dd, 1H), 3.79(s, 3H).

Compound 315B (β-isomer):
$^1$H-NMR(CDCl$_3$)δ:0.88(m, 2H), 2.44(dd, 1H), 3.80(s, 3H).

EXAMPLE 401

(1) 2-Palmitoylamidoethanethiol (Compound 403)

2-aminoethanethiol hydrochloride (Compound 401) (1.20 g, 10.6 mmol) and N-palmitoyloxysuccinimide (Compound 402) (3.73 g, 10.6 mmol) were added to methylene chloride (100 ml), to which was further added dimethylaminopyridine (1.94 g, 15.8 mmol), and the mixture was stirred at room temperature for 19 hours.

The resulting mixture was washed with water, and dried and the solvent was removed by distillation under reduced pressure. The residue was purified by column-chromatography with silica-gel (50 g) and chloroform, and the object compound was obtained as colorless powder (2.01 g, 60%).

$^1$H-NMR(CDCl$_3$)δ:0.87(3H, 5), 1.2–1.4(24H, m), 1.5–1.7(2H, m), 2.18(2H, t), 2.66(2H, m), 3.42(2H, q), 5.83(1H, s).

(2) Methyl [2-(2-palmitoylamido-1-ethyl)-5-acetamido-4,7,8,9-tetra-0-acetyl-3,5-dideoxy-2-thio-D-glycero-α-and-β-D-galacto-2-nonulopyranosidonate (Compounds 405α and 405β)

A mixture of powdered Molecular sieves 4A (600 mg) and zinc bromide (353 mg, 1.57 mmol) was stirred in methylene chloride (4 ml) at room temperature for 3 hours. On the other hand, a mixture of Compound 404 (400 mg, 0.78 mmol), Compound 403 (495 mg, 1.57 mmol) and molecular sieves (300 mg) was stirred in methylene chloride (10 ml) at room temperature for 3 hours. The resulting solution was poured dropwise to the first-mentioned mixture, and the resultant mixture was stirred at room temperature for 2 days.

To the resultant reaction mixture was added aqueous NaHCO$_3$ solution with stirring under ice cooling, and the insoluble matter was filtered out by celite filtration. The organic layer was, after separated, washed with water and dried, and the solvent was removed by distillation under reduced pressure. The residue was purified by column chromatography with silica-gel (60 g) and (chloroform→chloroform-methanol 100:1). The crude product was again subjected to column-chromatography with silica-gel (60 g) and (hexane-acetone 2:1) to produce a mixture of Compounds 405α and 405β in a ratio of about 1:1 (388 g, 63%).

$^1$H-NMR(CDCl$_3$)δ:0.88(3H, t), 1.2–1.4(24H, m), 1.88(1.5H, s), 1.89(1.5H, s), 2.02(1.5H, s), 2.03(1.5H, s), 2.04(1.5H, s), 2.05(1.5H, s), 2.08(1.5H, s), 2.15(1.5H, s), 2.16(1.5H, s), 2.21(1.5H, s), 3.80(1.5H, s), 3.81(1.5H, s).

(3) Methyl [2-(2-palmitoylamido-1-ethyl)-5-acetamido-3,5-dideoxy-2-thio-D-glycero-α-and-β-galacto-2-nonulopyranosidonate (Compounds 406α and 406β)

A mixture of Compounds 405α and 405β (380 mg, 0.48 mmol) was dissolved in methanol (3 ml). To the solution was added 28% sodium methoxide (15 μl), and the mixture was stirred at room temperature for 2 hours.

To the resulting reaction solution was added acetic acid (100 μl), and the mixture was concentrated under reduced pressure. The residue was purified by column-chromatography with silica-gel (20 g) and (chloroform-methanol 15:1), to produce a mixture of Compounds 406α and 406β as colorless foamy substance (155 mg, 52%).

$^1$H-NMR(CD$_3$OD)δ:0.90(3H, t), 1.21–1.5(24H, m), 2.00(1.5H, s), 2.01(1.5H, s), 3.79(1.5H, s), 3.84(1.5H, s).

(4) Sodium [2-(2-palmitoylamido-1-ethyl)-5-acetamido-3,5-dideoxy-2-thio-D-glycero-α-and-β-D-galacto-2-nonulopyranosid]onate (Compounds 407α and 407β)

A mixture of the methyl ester derivatives 406α and 406β (139 mg, 0.22 mmol) was dissolved in methanol (2 ml) and added with 0.1N aqueous NaOH solution (4.4 ml), and the mixture was stirred at room temperature for 10 days.

The reaction solution was neutralized with "Amberlite IRC-50", the insoluble matter was removed by filtration, and the filtrate was concentrated under reduced pressure, to produce a mixture of Compounds 407α and 407β as colorless powder (134 mg, 95%).

$^1$H-NMR(CD$_3$OD)δ:0.90(3H, t), 1.2–1.4(24H, m), 1.55–1.62(2H, m), 1.65(0.5H, dd), 1.85(0.5H, dd), 1.98(1.5H, s, CH$_3$CO), 2.00(1.5H, s, CH$_3$CO), 2.54(0.5H, dd).

For the sake of convenience the diagram illustrating the synthesis process of Example 401 is given below.

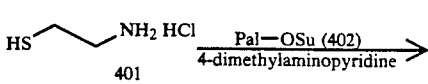

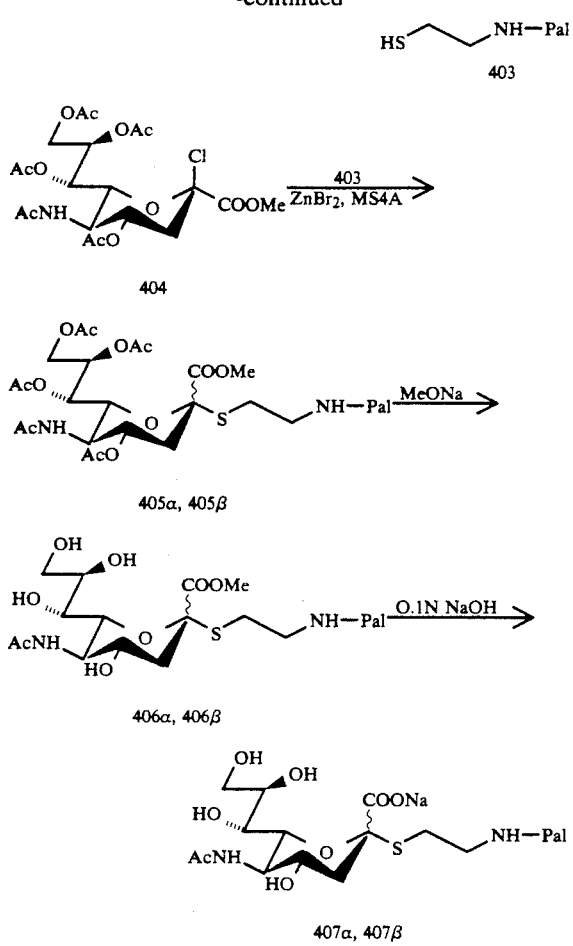

EXAMPLE 402

(1) Synthesis of cis-11-hexadecenyl thiobenzoate (Compound 424)

A solution of 10.36 g of triphenylphosphine and 7.99 g of diisopropyl azodicarboxylate dissolved in THF (100 ml) was stirred under ice cooling for 30 minutes, added dropwise with a solution of 5.00 g of cis-11-hexadecene-1-ol and 4.10 g of thiobenzoic acid dissolved in THF (50 ml), stirred for 1 hour, and further stirred at room temperature for 1 hour.

After completion of the reaction, the solvent was removed by distillation under reduced pressure, and purified by silica-gel column-chromatography (Nacalai, hexane:toluene=3:1), to produce 5.26 g of the thio ester (pale pink oil) (Compound 424). The yield was 74%.

$R_F$=0.58 (hexane:toluene 3:1).

$^1$H-NMR(CDCl$_3$)δppm:0.84–0.91(m, 3H), 1.20–1.36(m, 16H), 1.36–1.44(m, 2H), 1.62–1.69(m, 2H), 1.92–2.04(m, 4H), 3.05(t, 3H), 5.32–5.38(m, 2H), 7.39–7.45(m, 2H), 7.51–7.56(m, 1H), 7.93–7.98(m, 2H).

(2) Synthesis of cis-11-hexadecene-1-thiol (Compound 425)

To a solution of 5.25 g of the thio ester (Compound 424) dissolved in MeOH-THF (15 ml–6 ml) was added 2.5 ml of 28% NaOMe (in MeOH). The mixture was stirred at room temperature for 5 hour, and then added with 835 μl of AcOH (1 eq.). The solvent was removed by distillation under reduced pressure, and the residue was coarsely purified by silica-gel column-chromatography (Nakarai, CHCl$_3$), to produce 3.53 g of cis-11-hexadecene-1-thiol (Compound 425). The ratio was 83:17 (disulfide) based on NMR.

(3) Synthesis of methyl (cis-11-hexadecenyl-5-acetamido-4,7,8,9-tetra-0-acetyl-3,5-dideoxy-2-thio-D-glycero-α-and-β-D-galacto-2-nonulopyranosid)onate (Compounds 427α and 427β)

a) A solution of 0.5 g of Molecular sieves AW-300, 412 mg of cis-11-hexadecene-1-thiol (Compound 425) and 200 mg of the 2-acetoxy derivative of sialic acid (Compound 426a) dissolved in dichloromethane (10 ml) was added with 56 μl of tin tetrachloride, and the mixture was stirred under argon atmosphere at room temperature for 4 hours.

After completion of the reaction, the solution was filtered with celite, neutralized with sodium hydrogencarbonate, and subjected to extraction. Removal of the solvent by distillation under reduced pressure, followed by purification by silica-gel column-chromatography (CHCl$_3$:MeOH=150:1) gave separately 217.5 mg of the β-form (Compound 427β) and 17.4 mg of the α-form (Compound 427α). The percent yields were 80% and 6%, respectively.

b) A solution of 0.5 g of Molecular sieves 4A, 287 mg of cis-11-hexadecene-1-thiol (Compound 425) and 200 mg of the 2-chloro derivative of sialic acid (Compound 426b) dissolved in dichloromethane (10 ml) was added with 177 mg of zinc bromide, and the mixture was stirred under argon atmosphere at room temperature for 24 hours.

After completion of the reaction, the solution was filtered with celite, neutralized with sodium hydrogencarbonate, and subjected to extraction. Removal of the solvent by distillation under reduced pressure, followed by purification by silica-gel column-chromatography (CHCl$_3$:MeOH=150:1) gave separately 68.9 mg of the β-form (Compound 427β) and 42.1 mg of the α-form (Compound 427α). The percent yields were 24% and 15%, respectively.

α-form (Compound 427α):

$R_F$=0.42 (CHCl$_3$-MeOH 25:1).

$[α]_D^{25}$ +3.15° (c 0.89, CHCl$_3$).

$^1$H-NMR(CDCl$_3$):δppm:0.86–0.92(m, 3H), 1.23–1.38(m, 20H), 1.46–1.55(m, 2H), 1.87(s, 3H, NHAc), 1.98(dd, 1H), 1 96–2.06(m, 2H), 2.03(s, 3H), 2.04(s, 3H), 2.14(s, 3H), 2.16(s, 3H), 2.52(ddd, 1H), 2.72(dd, 1H), 3.74(ddd, 1H), 3.80(s, 3H), 3.83(dd, 1H), 4.05(ddd, 1H), 4.12(dd, 1H), 4.32(dd, 1H), 4.86(ddd, 1H), 5.13(d, 1H), 5.32(dd, 1H), 5.36(ddd, 1H), 5.34–5.40(m, 2H).

IR(Neat)cm$^{-1}$:1744, 1663, 1541, 1437, 1369, 1227(br.), 1038.

β-form (Compound 427β):

$R_F$=0.47 (CHCl$_3$-MeOH 25:1).

$[α]_D^{26}$ −59.4° (c 1.03, CHCl$_3$).

$^1$H-NMR(CDCl$_3$):δppm:0.86–0.91(m, 3H), 1.20–1.37(m, 20H), 1.48–1.55(m, 2H), 1.88(s, 3H), 1.94–1.99(m, 2H), 2.02(s, 3H), 2.04(s, 3H), 2.08(s, 3H), 2.13(s, 3H), 2.13(dd, 1H), 2.46(dt, 1H), 2.51(dd, 1H), 2.56(dt, 3H), 3.81(s, 3H), 4.08(ddd, 1H), 4.18(dd, 1H), 4.33(dd, 1H), 4.81(dd, 1H), 5.11(ddd, 1H), 5.26(m, 2H), 5.33–5.40(m, 2H), 5.43(dd, 1H).

IR(Neat)cm$^{-1}$:1720, 1690, 1662, 1548, 1436, 1371, 1240(br.), 1039.

(4) Synthesis of methyl (cis-11-hexadecenyl-5-acetamido-3,5-dideoxy-2-thio-D-glycero-α-D-galacto-2-nonulopyranosid)onate (Compound 428α)

A solution of 89.7 mg of the α form (Compound 427α) dissolved in methanol (3 ml) was added with 10 μl of sodium methoxide (23% NaOMe in MeOH), and the mixture was stirred at room temperature for 1.5 hours.

Concentration under reduced pressure, followed by purification by silica-gel column chromatography (CHCl$_3$:MeOH=25:1) gave 52.3 mg of the deacetylated derivative (Compound 428α). The yield was 76%.

$R_F$=0.52 (CHCl$_3$-MeOH 6:1).
$[\alpha]_D^{27}$ −37.3° (c 0.96, MeOH).
$^1$H-NMR(CD$_3$OD):δppm:0.87~0.93(m, 3H), 1.25–1.40(m, 20H), 1.47–1.60(m, 2H), 1.78(dd, 1H), 1.99(s, 3H), 2.00–2.06(m, 2H), 2.60(dt, 1H), 2.75(dd, 1H), 2.76(dt, 1H), 3.40(dd, 1H), 3.50(dd, 1H), 3.60–3.66(m, 2H), 3.77(dd, 1H), 3.83(s, 3H), 3.79–3.85(m, 2H), 3.79–3.85(m, 2H), 5.32~5.39(m, 2H).

(5) Synthesis of methyl (cis-11-hexadecenyl-5-acetamido-3,5-dideoxy-2-thio-D-glycero-β-D-galacto-2-nonulopyranosid)onate (Compound 428β)

To a solution of 207.3 mg of the β form (Compound 427β) dissolved in methanol (4 ml) was added 20 μl of sodium methoxide (23% NaOMe in MeOH), and the mixture was stirred at room temperature for 1.5 hours.

The solution was concentrated under reduced pressure, and purification by silica-gel column-chromatography (CHCl$_3$:MeOH=10:1), gave 124.3 mg of the deacetylated derivative (Compound 428β). The yield was 78%.

$R_F$=0.50 (CHCl$_3$-MeOH 6:1).
$[\alpha]_D^{25}$ −89.1° (c 1.17, MeOH).
$^1$H-NMR(CD3OD):δppm:0.87~0.93(m, 3H), 1.22–1.39(m, 20H), 1.44–1.55(m, 2H), 1.91(dd, 1H), 2.71(dt, 1H), 2.00–2.08(m, 2H), 2.45(dd, 1H), 2.55(dt, 1H), 2.71(dt, 1H), 3.52(dd, 1H), 3.66(dd, 1H), 3.77(s, 3H), 3.76–3.84(m, 3H), 4.09(ddd, 1H), 4.14(dd, 1H), 5.32–5.39(m, 2H).

(6) Synthesis of sodium (cis-11-hexadecyl-5-acetamido-3,5-dideoxy-2-thio-D-glycero-α-D-galacto-2-nonulopyranosid)onate (Compound 429α)

To a solution of 29.5 mg of the methyl ester derivative (Compound 428α) dissolved in 2 ml of methanol was added 1.93 ml of 0.1N NaOH, and the mixture was stirred at room temperature for 7 days. The mixture was further added with 1 ml of 0.1N NaOH, and heated at 60° C. for 4 hours, followed by removal of the solvent by distillation under reduced pressure. The residue was subjected to gel filtration (LH-20, 6φ×300 mm, CHCl$_3$:MeOH 1:1) for purification, to produce white powder (Compound 429α) in a stoichiometric amount. The yield was 99%.

$R_F$=0.67 (BuOH-AcOH-H$_2$O 2:1:1).
$[\alpha]_D^{25}$ +22.9° (c 0.91, MeOH).
$^1$H-NMR(CD3OD):δppm:0.98–0.93(m, 3H), 1.24–1.39(m, 20H), 1.51–1.65(m, 2H), 1.63(dd, 1H), 1.99–2.06(m, 2H), 2.00(s, 3H), 2.67(dt, 1H), 2.86(dt, 1H), 2.87(dd, 1H), 3.48(dd, 1H), 3.50(dd, 1H), 3.62(dd, 1H), 3.67(dd, 1H), 3.71(ddd, 1H), 3.81(dd, 1H), 3.85(ddd, 1H), 5.32–5.40(m, 2H).

IR(KBr)cm$^{-1}$:3404, 3007, 1603(br), 1377, 1124, 1032.

(7) Synthesis of sodium (cis-11-hexadecenyl-5-acetamido-3,5-dideoxy 2-thio-D-glycero-β-D-galacto-2-nonulopyranosid)onate (Compound 429β)

To a solution of 110.3 mg of the methyl ester derivative (Compound 428β) dissolved in 4 ml of methanol was added an equivalent amount of 0.1N NaOH, and the mixture was stirred at room temperature for 3 days. The solvent was removed by distillation under reduced pressure, to produce white powder (Compound 429β) in a stoichiometric amount. The yield was 100%.

$R_F$=0.74 (BuOH-AcOH-H$_2$O 2:1:1).
$[\alpha]_D^{27}$ −81.6° (c 0.98, MeOH).
$^1$H-NMR(CD$^3$OD):δppm:0.87~0.95(m, 3H), 1.28–1.43(m, 20H), 1.51~1.59(m, 2H), 1.81(dd, 1H), 1.98(s, 3H), 2.01–2.06(m, 2H), 2.54(dd, 1H), 2.55–2.63(m, 2H), 3.47(d, 1H), 3.66(dd, 1H), 3.74–3.79(m, 2H), 3.86(dd, 1H), 3.96(ddd, 1H), 4.20(d, 1H), 5.31~5.40(m, 2H).

IR(KBr)cm$^{-1}$:3400, 1612(br), 1377, 1126, 1088, 1030.

For the sake of convenience the diagram illustrating the synthesis process of Example 402 is given below.

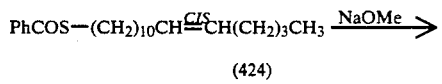

(424)

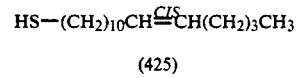

(425)

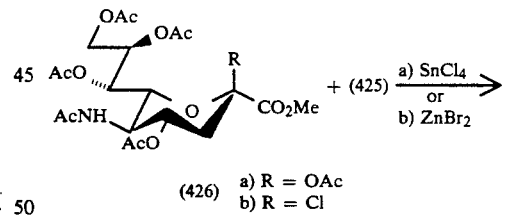

(426) a) R = OAc
      b) R = Cl

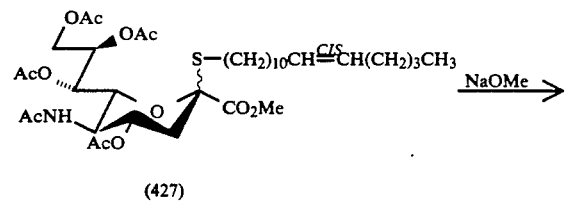

(427)

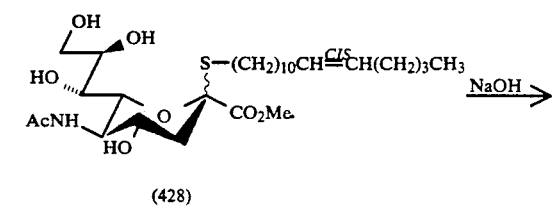

(428)

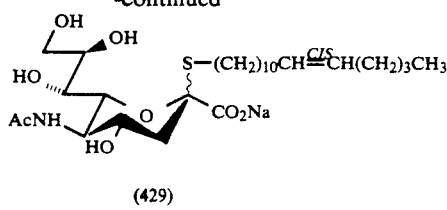

(429)

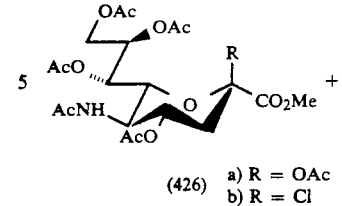

(426) a) R = OAc
b) R = Cl

Example 403 Synthesis of methyl {2-p-nitrobenzyloxycarbonylamino)ethyl-5-acetamido-4,7,8,9-tetra-0-acetyl-3,5-dideoxy-2-thio-D-glycero-α-and β-D-galacto-2-nonulopyranosid}onate (Compound 431α and 431β)

a) To a solution of 0.05 g of Molecular sieves AW-300, 288 mg of 2-(p-nitrobenzyloxycarbonylamino) ethanethiol (Compound 430) and 200 mg of the 2-acetoxy derivative of sialic acid (Compound 426a) dissolved in dichloromethane (10 ml) was added 56 μl of tin tetrachloride, and the mixture was stirred under argon atmosphere at room temperature for 50 hours.

After completion of the reaction, the mixture was filtered with celite, neutralized with sodium hydrogencarbonate, and subjected to extraction. Removal of the solvent by distillation under reduced pressure, followed by purification by silica-gel column-chromatography (CHCl$_3$:MeOH=50:1), to produce 167 mg of a mixture (compound 431) of the α- and the β-forms (the yield being 61% with α:β=8:92).

For the synthesis of Compound 430, refer to "Synthesis", 11, 924–926(1980).

b) To a solution of 0.5 g of Molecular sieves 4A, 201 mg of 2-(p-nitrobenzyloxycarbonylamino) ethanethiol (Compound 430) and 200 mg of the 2-chloro derivative of sialic acid (Compound 426b) dissolved in dichloromethane (10 ml) was added 177 mg of zinc bromide, and the mixture was stirred under argon atmosphere at room temperature for 19 hours.

After completion of the reaction, the solution was filtered with celite, neutralized with sodium hydrogencarbonate, and subjected to extraction. Removal of the solvent by distillation under reduced pressure, followed by purification by silica-gel column-chromatography ((1) CHCl$_3$:MeOH=50:1, (2) hexane:acetone=2:1) gave 81.7 mg of a mixture (Compound 431) of the α- and the β-forms (the percent yield being with α:β=24:76).

α, β(Compound 431):
R$_F$=0.38 (CHCl$_3$-MeOH 25:1).
$^1$H-NMR(CDCl$_3$):δppm

For the β form (Compound 431β); 1.88(s, 3H), 2.02(s, 3H), 2.08(s, 3H), 2.15(s, 3H), 2.18(s, 3H), 2.18(dd, 1H), 2.52(dd, 1H), 2.72(m, 1H), 2.86(m, 1H), 3.35(m, 2H), 3.80(s, 3H), 4.04(dd, 1H), 4.08(dd, 1H), 4.30(dd, 1H), 5.01(dd, 1H), 5.18(ddd, 1H), 5.20(s, 2H), 5.28(ddd, 1H), 5.43(d, 1H), 5.44(m, 1H), 5.64(m, 1H), 7.52(d, 2H), 8.22(d, 2H).

For the α form (Compound 431α);
2.71(dd, 1H), 4.88(ddd, 1H), 5.37(ddd, 1H), 5.86(m, 1H).

IR(KBr)cm$^{-1}$:1744, 1668, 1526, 1440, 1371, 1350, 1232, 1037.

For the sake of convenience the diagram illustrating the synthesis process of Example 403 is given below.

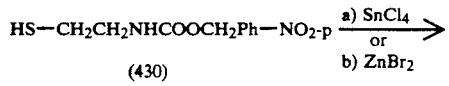

(430)

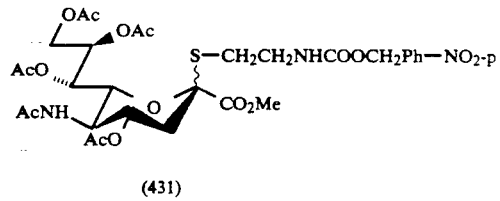

(431)

Industrial Applicability

The particulate carrier containing as its constituent a compound of this invention is resistant to capture by the reticuloendothelial system, capable of maintaining microcirculation in blood, can hold a higher drug concentration in blood, and allows reproducible production. Moreover, as stated above, the particulate carrier containing a compound of this invention is capable of maintaining microcirculation when injected systemically, suggesting its stableness in body fluids. Depending on this property this carrier can be utilized as an agent capable of gradual release of active ingredients when administered locally. Needless to say, such particulate carrier is useful not only to human beings but also to other warm-blooded animals such as livestock and fowls.

We claim:

1. A sialic acid-containing glycolipid derivative of the formula (I):

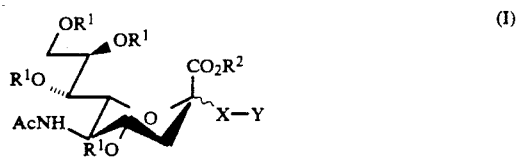

(I)

where ~ represents an α or a β linkage;

R$^1$ is a hydrogen atom or an acetyl group;

R$^2$ is a hydrogen atom, a lower alkyl group having 1–4 carbon atoms, an alkali metal ion, an alkali earth metal ion or an ammonium ion;

X is an oxygen atom, sulfur atom or a residue of the formula (II):

(II)

where m is an integer of from 1 to 10;

Y is represented by the formula (IV):

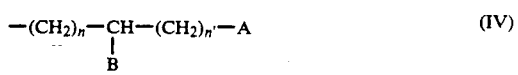

(IV)

where A is a hydrogen atom, a linear or branched chain acylamino, alkyl, alkenyl, alkoxy, alkenyloxy, alkylthio or alkenythio group having 10–40 carbon atoms;

B is a hydrogen atom, a carboxyl group, or carbamoyl group, an N-alkyl-substituted carbamoyl group, an alkyl, alkenyl, alkoxy, alkenyloxy or acylamino group having 10–30 carbon atoms, or a residue represented by the formula (V):

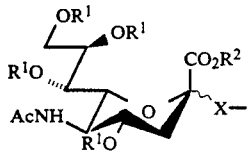
(V)

in which $R^1$, $R^2$ and X have the same meanings as above, n and n′ each represent an integer of 0 to 3;

excluding those derivatives (a) of formula (I) where X is an oxygen or sulfur atom, and one of A and B is formula (IV) is a hydrogen atom and the other is an alkyl or alkenyl group; (b) of formula (I) where X is an oxygen or sulfur atom, ad A and B in formula (IV), which may be the same or different, is an alkyl or alkenyl group; and (c) of formula (I) where X is an oxygen atom or a sulfur atom and A and B in formula (IV) are both alkyloxy groups.

2. A sialic acid-containing glycolipid derivative of formula (VI):

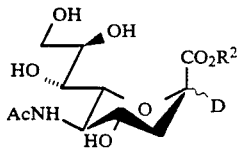
(VI)

where ∼ and $R^2$ has the same meaning as in formula (I); and

D is a linear or braced chain alkyloxy or alkenyloxy group having 14–40 carbon atoms.

3. A sialic acid derivative represented by the formula (XIII):

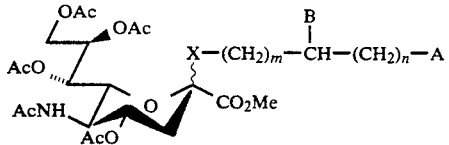
(XIII)

where X is an oxygen or sulfur atom;

m and n are integers 0 to 10;

A is a hydrogen atom, a linear or branched chain acylamino, alkyl, alkenyl, alkoxy, alkenyloxy or azido group having 10–40 carbon atoms, or an amino group protected by a protective group; and B is a hydrogen atom, a linear or branched chain alkyl or alkenyl group having 10–30 carbon atoms, a lower alkoxycarbonyl group having 2 or 3 carbon atoms in total, or a substituted or unsubstituted benzyloxy carbonyl group, excluding those derivatives (a) of formula (XIII) where X is an oxygen atom, m=1, n=0, A is a benzyloxycarbonylamino group, and B is a hydrogen atom and in the α-form; (b) of formula (XIII) where X is an oxygen or a sulfur atom, and A and B are both hydrogen atoms or an alkyl, alkenyl, alkoxy or alkenyloxy group;

(c) and of formula (XIII) where both A and B are hydrogen atoms, or an alkyl or alkenyl group when X is a sulfur atom.

4. A sialic acid derivative of formula (XIIIa):

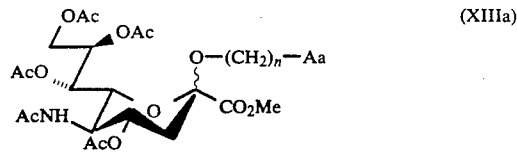
(XIIIa)

where ∼ represents an α or a β-linkage; n is an integer of 1 to 20; and Aa is an azido group or an amino group protected with a protecting group;

excluding those derivatives of formula (XIIIa) where n=2 and Aa is a benxyloxycarbonylamino group and in the α form.

5. A sialic acid derivative represented by the formula (XXI):

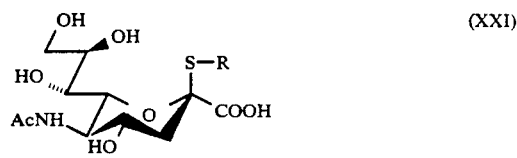
(XXI)

where R is a linear or branched chain alkyl or alkenyl group or the salts thereof.

6. A sialic acid derivative claimed in claim 5 where R is $(CH_2)_n CH_3$ where n represents an integer of 13–29 or the salts thereof.

7. A particulate drug carrier comprising at least one compound as claimed in claim 1.

8. A particulate drug carrier comprising at least one compound as claimed in claim 2.

9. A particulate drug carrier comprising at least one compound as claimed in claim 3.

10. A particulate carrier comprising at least one compound of formula (XXIa):

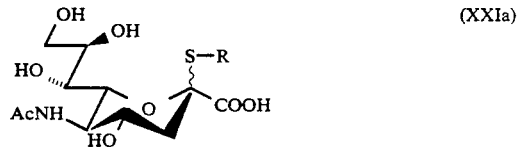
(XXIa)

where R is a linear or branched chain alkyl or alkenyl group, and ∼ represents α- or a β-linkage, or the salts thereof.

11. A liposome membrane having incorporated therein a glycolipid derivative of claim 1.

12. A liposome membrane having incorporated therein a glycolipid derivative of claim 2.

13. A liposome membrane having incorporated therein a glycolipid derivative of claim 3.

14. A liposome membrane having incorporated therein a glycolipid derivative of claim 4.

15. Sodium [2-(8-palmitoylamido-1-octyl)-5-acetamido-3,5-dideoxy-D-glycero-β-D-galacto-2-nonulopyrnosid]onate.

16. Sodium [2-(2-palmitoylamido-1-ethyl)-5-acetoamido-3,5-dideoxy-D-glycero-β-D-galacto-2-nonulopyranosid]onate.

17. Sodium [2-hexadecyl-5-acetamido-3,5-dideoxy-D-glycero-β-D-galacto-2-nonulopyranosid]onate.

* * * * *